(12) United States Patent
Cai

(10) Patent No.: US 8,802,078 B2
(45) Date of Patent: Aug. 12, 2014

(54) COMPOSITIONS AND METHODS FOR MODIFYING A SILICONE SURFACE FOR PROLONGED INTERFERENCE AGAINST PATHOGEN COLONIZATION

(75) Inventor: Chengzhi Cai, Houston, TX (US)

(73) Assignee: University of Houston, Houston, TX (US)

( * ) Notice: Subject to any disclaimer, the term of this patent is extended or adjusted under 35 U.S.C. 154(b) by 31 days.

(21) Appl. No.: 13/418,131

(22) Filed: Mar. 12, 2012

(65) Prior Publication Data

US 2012/0231518 A1    Sep. 13, 2012

Related U.S. Application Data

(60) Provisional application No. 61/451,866, filed on Mar. 11, 2011.

(51) Int. Cl.
*B05D 3/00* (2006.01)
*A61K 45/00* (2006.01)

(52) U.S. Cl.
CPC ..................................... *A61K 45/00* (2013.01)
USPC ...................................... 424/93.45; 427/2.24

(58) Field of Classification Search
None
See application file for complete search history.

(56) References Cited

PUBLICATIONS

Trautner BW, Darouiche RO. Catheter-associated infections—pathogenesis affects prevention. Arch Intern Med (2004) 164:842-850.*

* cited by examiner

*Primary Examiner* — Jean Witz
*Assistant Examiner* — Mindy Newman
(74) *Attorney, Agent, or Firm* — Winstead PC

(57) ABSTRACT

According to some embodiments, the present invention provides a modified silicone surface for interference to pathogen colonization comprising: an activated silicone layer; a plurality of cross-linking dendrimers adsorbed onto to the activated silicone layer; a plurality of ligand derivatives, each bound to at least one of the plurality of cross-linking dendrimers; and a benign biofilm adhered to the plurality of ligand derivatives. According to some embodiments, the present invention provides a method for making a modified silicone surface for interference to pathogen colonization comprising activating a silicone surface; adsorbing a plurality of cross-linking dendrimers to the silicone surface; binding a plurality of ligand derivatives to the plurality of cross-linking dendrimers; and adhering a benign biofilm to the plurality of ligand derivatives.

37 Claims, 25 Drawing Sheets

_COMPOSITIONS AND METHODS FOR MODIFYING A SILICONE SURFACE FOR PROLONGED INTERFERENCE AGAINST PATHOGEN COLONIZATION_

CROSS-REFERENCE TO RELATED APPLICATION

This application claims priority to U.S. Provisional Application No. 61/451,866, to Chengzhi Cai, entitled "Biofunctionalization of silicone polymers using poly(amido amine) dendrimers and a mannose derivative for prolonged interference against pathogen colonization", hereby incorporated herein by reference.

STATEMENT OF FEDERAL GOVERNMENT SPONSORSHIP

The present invention was made with government support under Grant No. 1R21 HD058985-02, awarded by the National Institutes of Health through the National Institute of Child Health & Human Development; and Grant No. DMR-0706627, awarded by the National Science Foundation. The Government has certain rights in this invention.

FIELD OF THE INVENTION

The present invention related to compositions and methods for anti-microbial silicone surfaces.

BACKGROUND

Catheter-associated urinary tract infection (CAUTI) is the most common type of hospital-acquired infection accounting to about 30% of the infections reported by acute care hospitals in the United States and affecting millions of patients worldwide annually [1-4]. Like other nosocomial infections on medical implants, CAUTI involves the formation of pathogenic biofilms on the surface of urinary catheters. Pathogenic bacteria in the biofilms are embedded in a self-produced polymer matrix, which protect themselves against antimicrobial agents, and facilitate the development of resistance to antibiotics [1, 5-8]. To inhibit biofilm formation, one of the most studied strategies includes the incorporation of antimicrobial agents to urinary catheters, which are mostly made of silicone polymers [9-13]. While some of the results encouraged further development, many appeared not promising, especially those relevant to long-term catheter use [2, 3, 14]. A great challenge to overcome is to completely prevent biofouling on the catheters, which blocks the antimicrobial agents and provides a new platform for growing biofilms [2]. While recent studies on antifouling coatings against bacterial adhesion has made impressive progress [9, 15-17], the rapidly increasing pressure of antibiotic resistance and cost for treatment of CAUTI has called to speed up the development of alternative strategies [7, 18].

One alternative strategy is based on bacterial interference using benign biofilms of probiotic bacteria to protect against the attachment and colonization of pathogens [19-24]. An example of probiotic bacteria, also called "friendly bacteria" or "good bacteria", is the beneficial bacteria found in the human gut [25]. Despite some of the potential safety concerns, such as gene transfer and pathogenicity, it has been proven that probiotics are vital to proper health maintenance [26, 27]. They have been used as dietary supplements and drug against various bowel disease [25, 26], and investigated for preventing CAUTI and bacterial vaginosis [28-33]. In clinical trials, probiotic _E. coli_ 83972 have successfully colonized bladders leading to a significant decrease in the frequency of urinary tract infection without notable side effects [22-24, 34, 35]. As compared to antimicrobial coatings that are prone to leaching and fouling [21, 30, 32, 36], the living biofilms of probiotic bacteria grown on catheters actively produce molecules to outcompete a wide range of aggressive pathogens. This unique feature has rendered bacterial interference one of the most promising approaches for preventing CAUTI.

Despite of its great potentials, the effectiveness of the bacterial interference approach relies greatly on the establishment of a high coverage, stable pre-formed benign biofilms on the surface. Pre-inoculation of urinary catheters with _E. coli_ 83972 was used to introduce the benign bacteria to the bladder. However, it has been shown that _E. coli_ 83972 and several other benign bacteria adhered less and formed biofilms more slowly on silicone surfaces than common uropathogens [37]. Interestingly, the results were the opposite on solid substrates (glass and polystyrene tissue culture plates) [37]. Thus, the utility of the benign biofilms on silicone catheter to outcompete challenge pathogens had been limited to relatively short bacterial interference time (30 min) [38, 39], while prolonged exposure led to detachment and significant decrease in coverage of the benign _E. coli_ on the silicone catheter surface [40].

Biofilm formation is enhanced by the presence of adhesins including type 1 fimbriae present on most _E. coli_ strains [41]. However, the wild-type _E. coli_ 83972 does not express the common type 1 fimbriae because of its incomplete fim operon [42]. A transformed _E. coli_ 83972 strain expressing type 1 fimbriae (fim+_E. coli_ 83972) improved the biofilm formation on urinary catheters [43]. Since type 1 fimbriae binds mannose ligands [44], many _E. coli_ strains expressing type 1 fimbriae have a high affinity to mannose-presenting surfaces [45-49]. It has also been demonstrated that the adherence of uropathogens is significantly reduced if a biofilm of fim+_E. coli_ is pre-coated on the substrates [38, 39], including the mannose-modified single crystal silicon substrates. Therefore, we anticipated that covalent modification of silicone catheters would increase the coverage and stability of the biofilms of fim+_E. coli_ 83972 and improve the efficiency for bacterial interference.

SUMMARY

According to some embodiments, the present invention provides a modified silicone surface for interference to pathogen colonization comprising: an activated silicone layer; a plurality of cross-linking dendrimers adsorbed onto to the activated silicone layer; a plurality of ligand derivatives, each bound to at least one of the plurality of cross-linking dendrimers; and a benign biofilm adhered to the plurality of ligand derivatives.

The activated silicone layer may comprise an oxidized silicone layer. The oxidized silicone layer may comprise oxidized carbon species. The silicone layer may comprise poly (dimethylsiloxane).

The cross-linking dendrimers may each comprise an amidation product of the amino-terminus of an amino-terminated cross-linking dendrimer. The amino-terminated cross-linking dendrimers may comprise a dendrimeric moiety selected from the group consisting of poly(amido amine)polylysine, poly(amino acid), polyallylamine, polyamines, poly(propylene imine), and combinations thereof. The amino-terminated cross-linking dendrimers may each comprise a generation 5 amino-terminated poly(amido amine) dendrimer.

The ligand derivatives may each comprise an amidation product of a carboxylic acid terminal group. The ligand may comprise mannose. The ligand derivatives may each comprise a linker. The linker may comprise oligo(ethylene)glycol. When the ligand comprises mannose and an oligo(ethylene)glycol linker, the ligand derivatives may each comprise a glycosidic linkage to one of the oligo(ethylene)glycol linker and a moiety bonded to the oligo(ethylene) glycol linker. The moiety may be selected from the group consisting of phenyl, alkylphenyl, biphenyl, fluorinated biphenyl, hydroxylated biphenyl, and triazolylalkyl.

The benign biofilm may be stable. The benign biofilm may be dense. The benign biofilm may comprise a plurality of bacteria. The bacteria may comprise bacteria oriented vertically. The bacteria may comprise E. coli 83972. The bacteria may comprise E. coli Nissle 1917.

It will be understood that the above-described composition variations may be used singly or in combination. For example, according to some embodiments, the activated silicone layer comprises poly(dimethyl siloxane) and oxidized carbon species; the cross-linking dendrimers each comprise an amidation product of generation 5 amino-terminated poly(amido amine) dendrimer; the mannose derivatives each comprise the amindation product of a carboxy terminus, an oligo(ethylene)glycol linker, and a glycosidic linkage to one of the oligo(ethylene) glycol linker and a moiety bonded to the oligo(ethylene)glycol linker, wherein the moiety is selected from the group consisting of phenyl, alkylphenyl, biphenyl, fluorinated biphenyl, hydroxylated biphenyl, and triazolylalkyl; and the benign biofilm comprises a plurality of vertically oriented bacteria selected from the group consisting of E. coli 83972 and E. coli Nissle 1917.

According to some embodiments, the present invention provides a method for making a modified silicone surface for interference to pathogen colonization comprising activating a silicone surface; adsorbing a plurality of cross-linking dendrimers to the silicone surface; binding a plurality of ligand derivatives to the plurality of cross-linking dendrimers; and adhering a benign biofilm to the plurality of mannose derivatives.

The activating may comprise oxidizing. The oxidizing may comprise treating with a plasma. The treating may comprise optimized conditions. The optimized conditions may comprise low power. The power may be between about 1 W and about 10 W.

The benign biofilm may comprises a plurality of bacteria and the optimized conditions may comprise a plasma exposure time large enough to generate dense coverage of the bacteria and small enough to minimize degradation of the oxidized silicone layer. The optimized conditions may comprise a plasma exposure time between about 30 seconds and about 60 seconds.

The adsorbing may comprise immersing the activated silicone surface in a solution of the plurality of cross-linking dendrimers.

The binding may comprise amidation. The cross-linking dendrimers may be amino-terminated. The ligand derivatives may be carboxy-terminated. The binding may comprise providing the ligand derivatives. The ligand may comprise a mannose derivative. The ligand derivatives may each comprise a linker. The linker may comprise an oligo(ethylene) glycol linker. The providing may comprise forming a glycosidic linkage to one of the oligo(ethylene) glycol linker and a moiety bonded to the oligo(ethylene)glycol linker, wherein the moiety is selected from the group consisting of phenyl, alkylphenyl, biphenyl, fluorinated biphenyl, hydroxylated biphenyl, and triazolylalkyl. The adsorbing may precede the binding. Alternatively, the binding may precede the adsorbing.

The adhering comprise may incubation in a bacterial culture.

It will be understood that the above-described method variations may be used singly or in combination.

BRIEF DESCRIPTION OF DRAWINGS

The foregoing summary as well as the following detailed description will be better understood when read in conjunction with the appended drawings. It should be understood, however, that the present invention is not limited to the precise arrangements and instrumentalities shown herein. The components in the drawings are not necessarily to scale, emphasis instead being placed upon clearly illustrating the principles of the present invention. Moreover, in the drawings, like reference numerals designate corresponding parts throughout the several views.

The invention may take physical form in certain parts and arrangement of parts. For a more complete understanding of the present invention, and the advantages thereof, reference is now made to the following descriptions taken in conjunction with the accompanying drawings, in which.

Figure 1A:
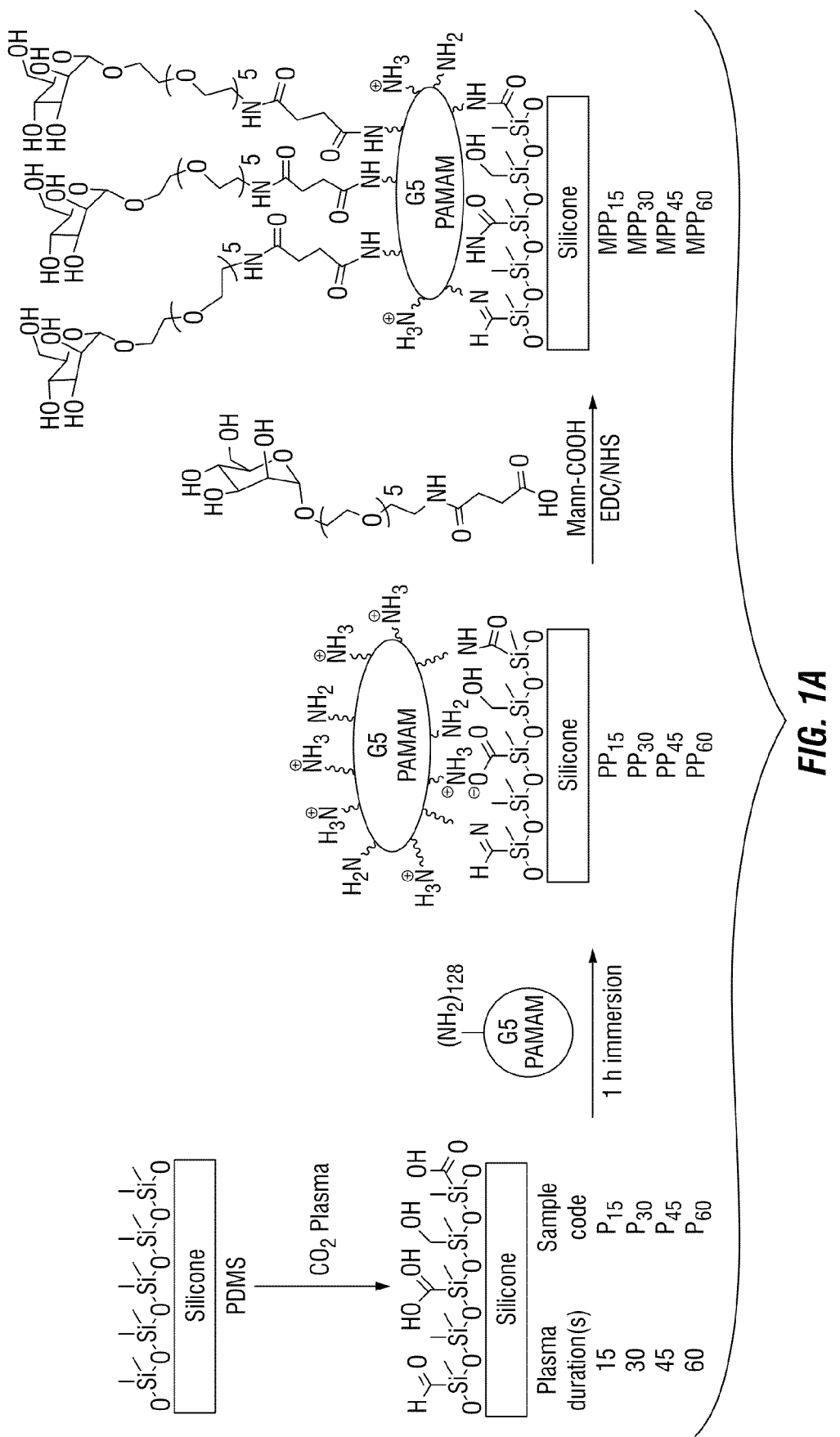
FIG. 1 depicts an outline of an embodiment of this invention: (A) Preparation of mannose-presenting silicone (PDMS) surfaces by $CO_2$ plasma treatment for 15, 30, 45, 60 s to provide the activated surfaces $P_n$, respectively (n=plasma treatment time, and n is varied from 15 to 60 s), followed by immersion in a solution of G5 PAMAM dendrimers containing about 128 $NH_2$ groups, leading to the corresponding amino-terminated PAMAM surfaces $PP_n$ (where 15<s<60), and followed by the attachment of Mann-COOH to afford the corresponding mannose-modified silicone surfaces $MPP_n$ (where 15<n<60), (B) Preparation of benign biofilms of E. coli 83972 and demonstration of bacterial interference, i.e., by exclusion of pathogens from the benign biofilm, using E. faecalis as a model.
Figure 1B:
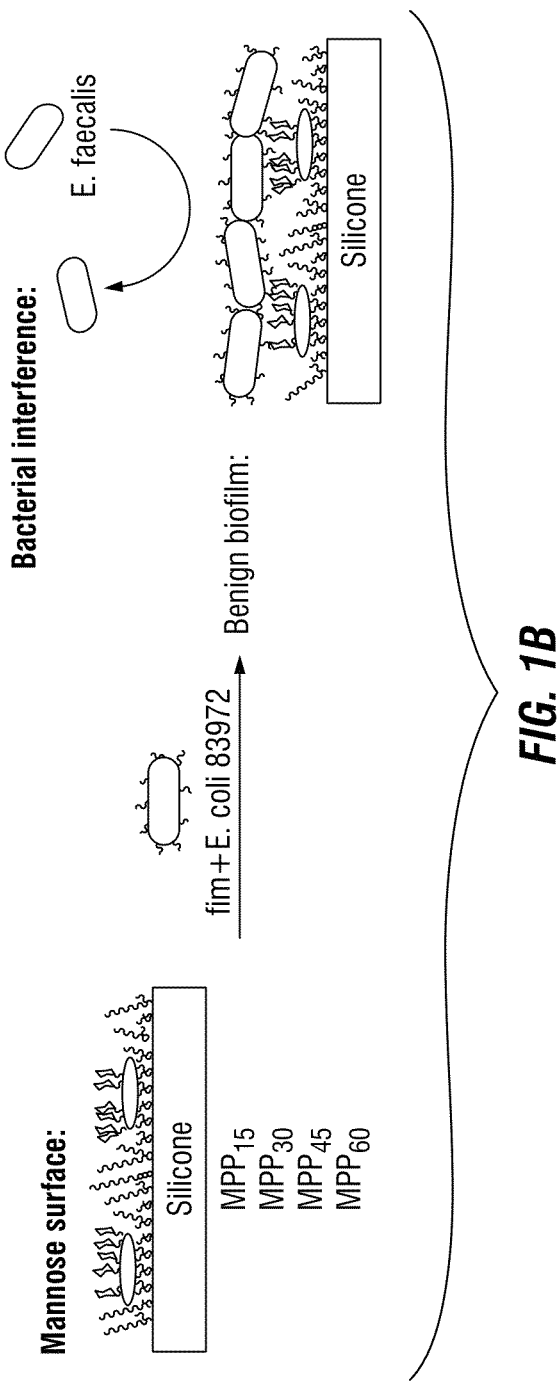
Figure 8A:
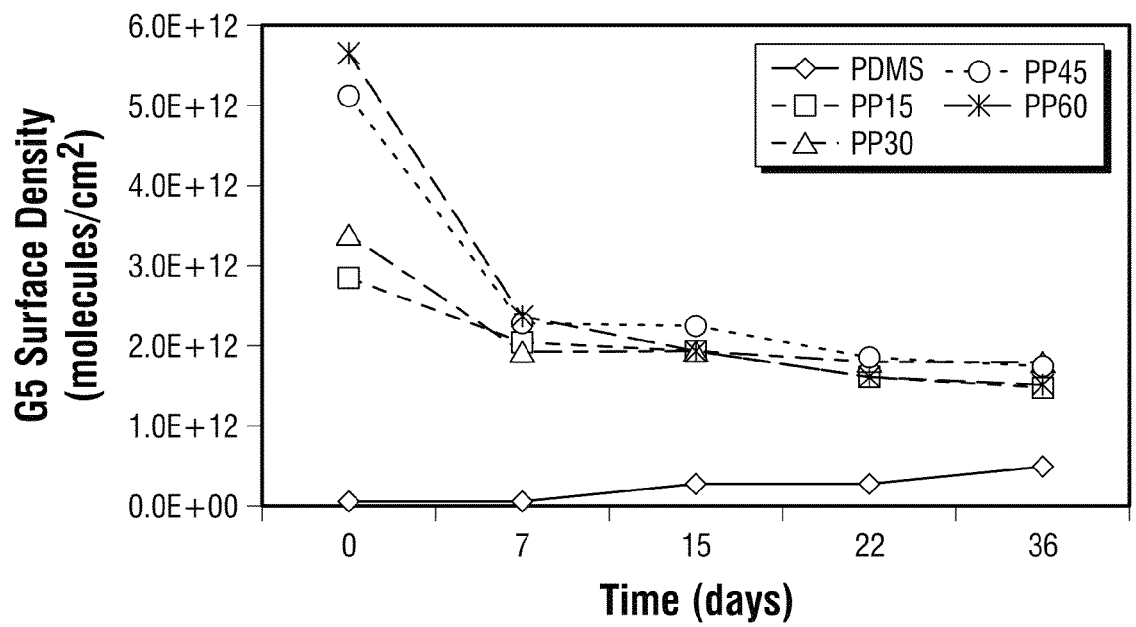
Figure 8B:
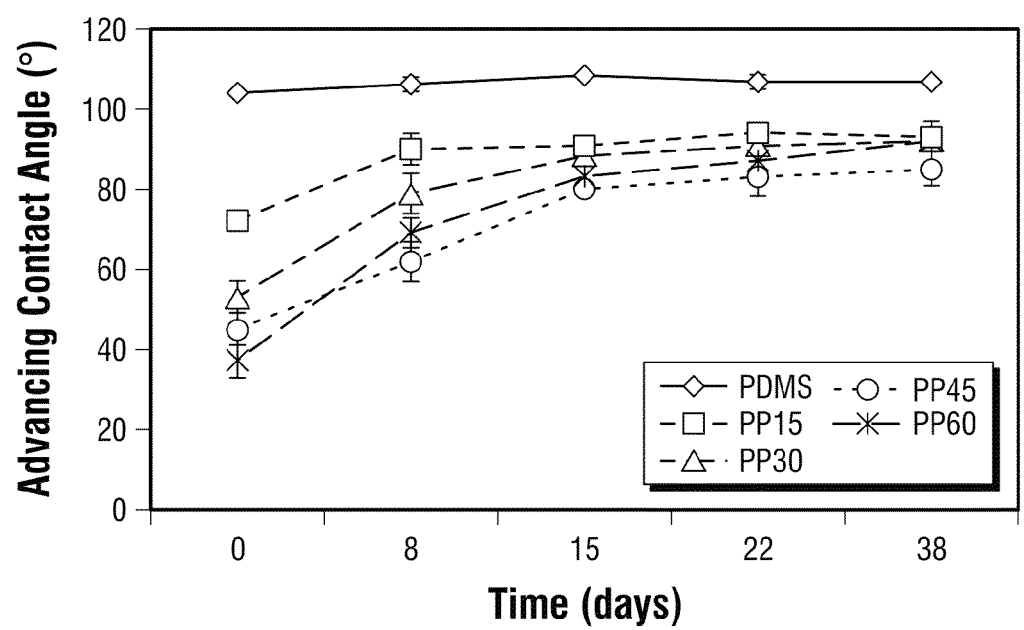
Figure 9A:
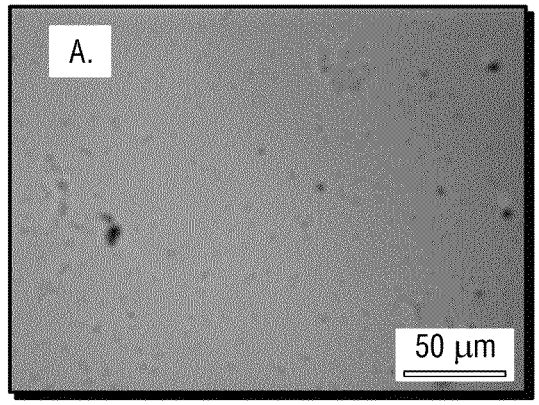
Figure 9B:
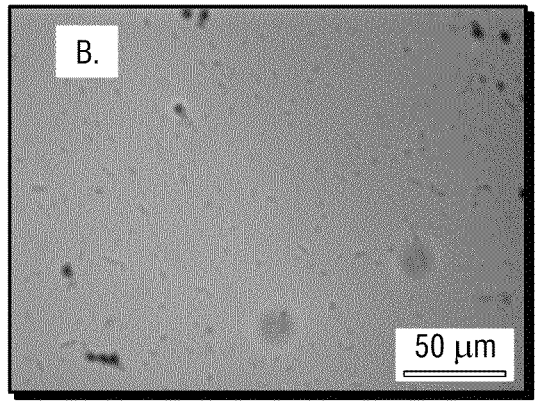
Figure 9C:
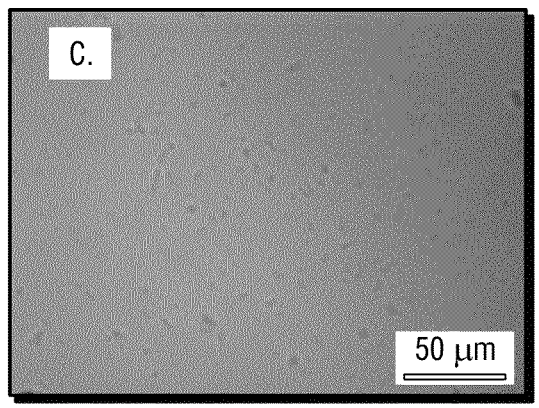
Figure 9D:
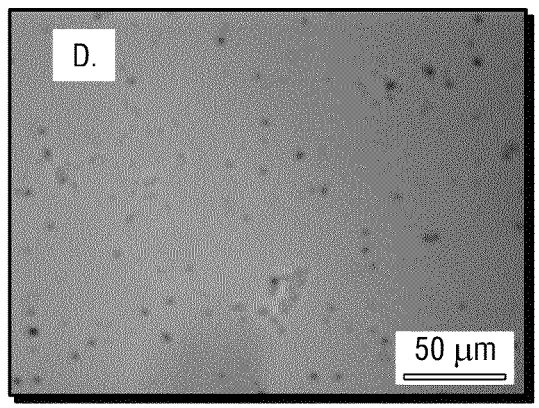
Figure 9F:
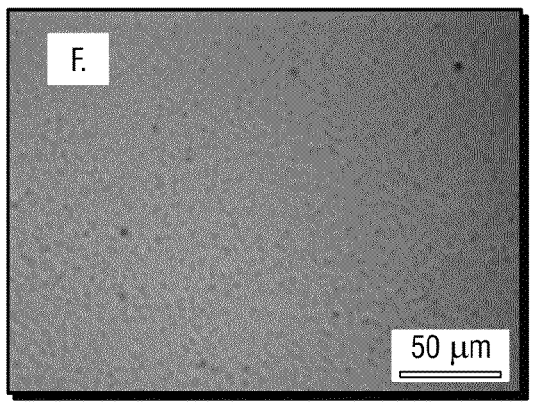
Figure 9G:
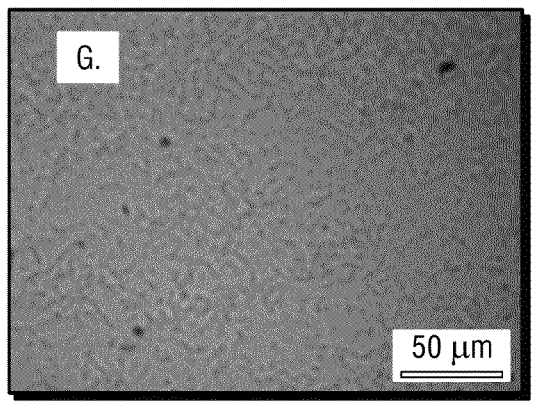
Figure 9H:
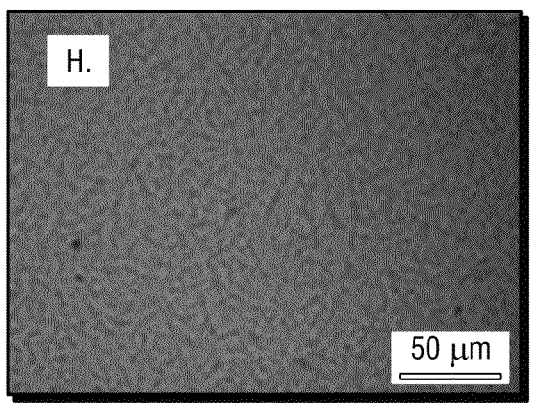
Figure 9I:
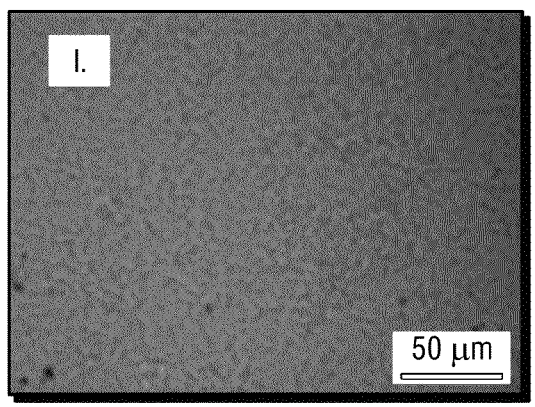
Figure 10:
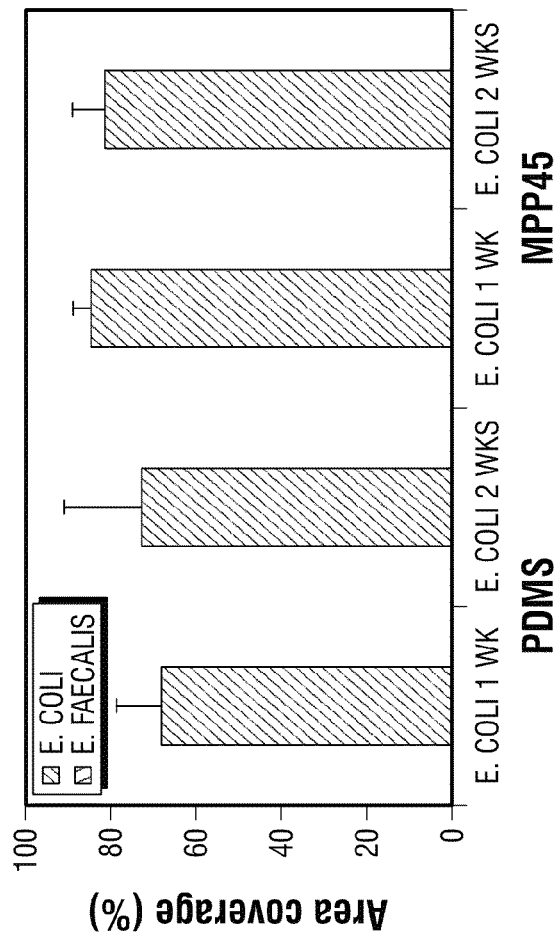
Figure 11:
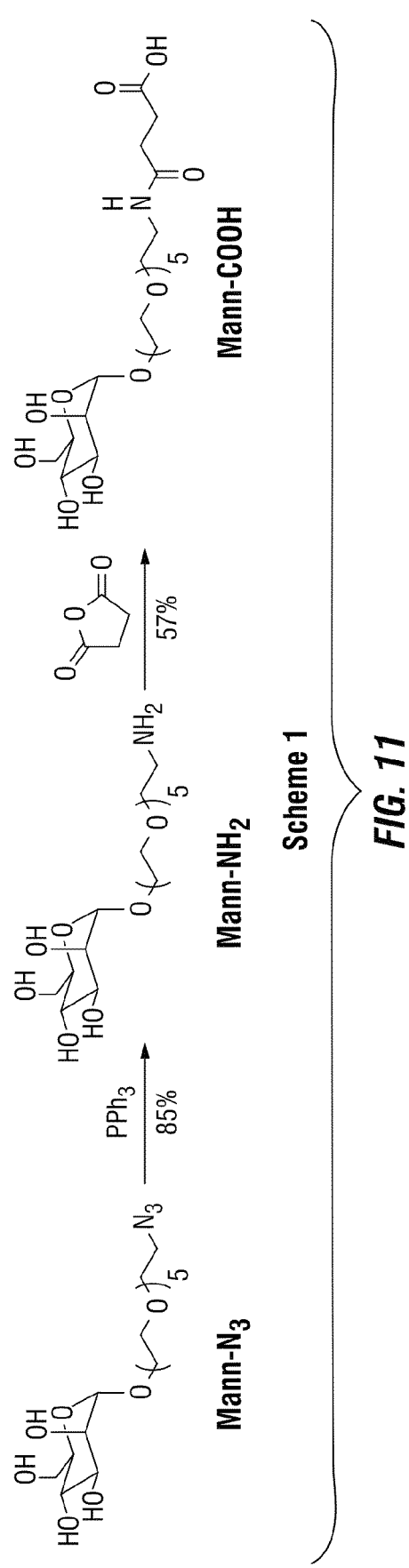
Figure 12A:
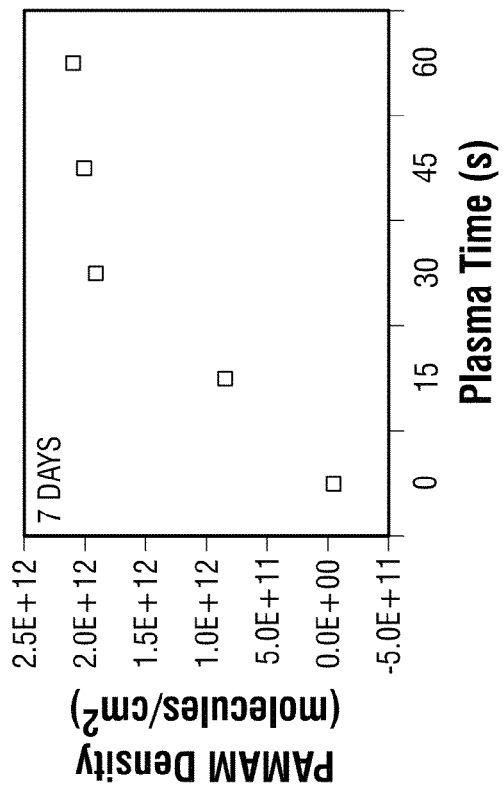
Figure 12B:
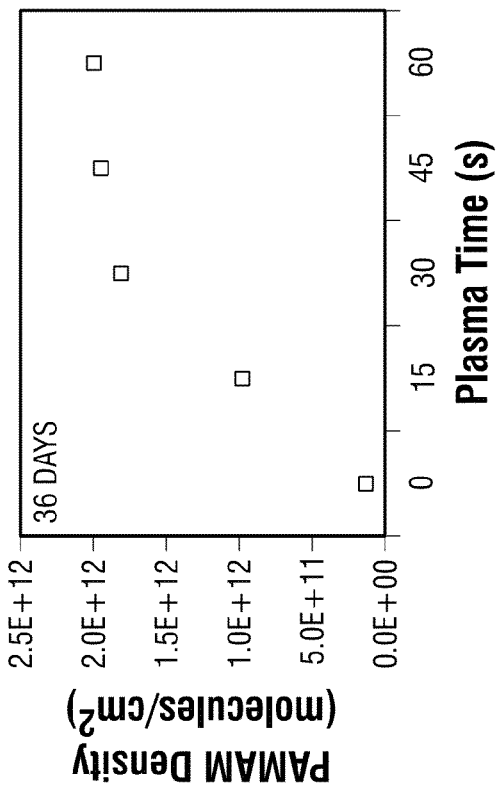
Figure 12C:
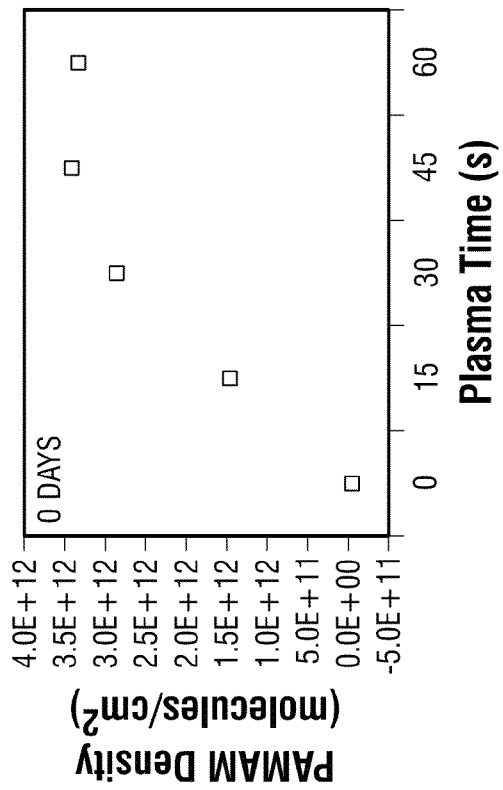
Figure 12D:
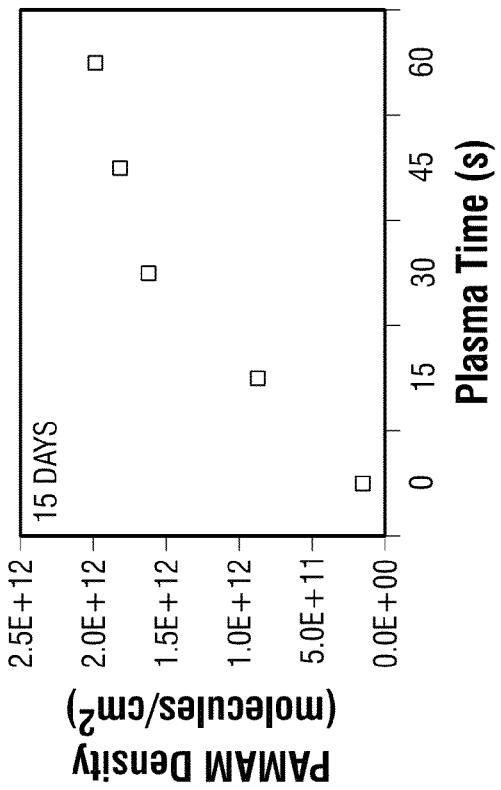
Figure 13A:
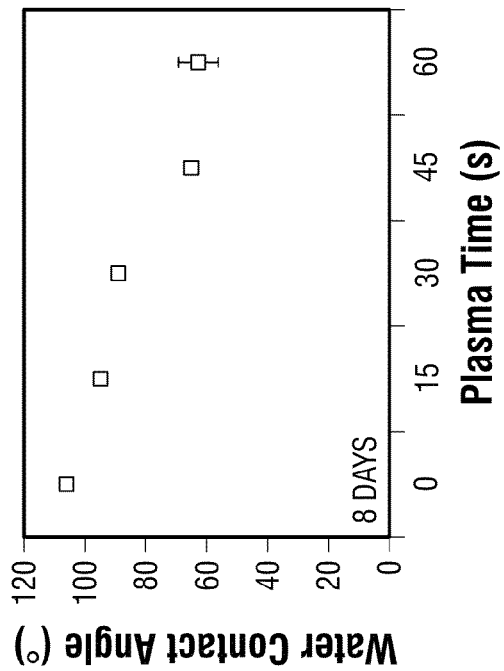
Figure 13B:
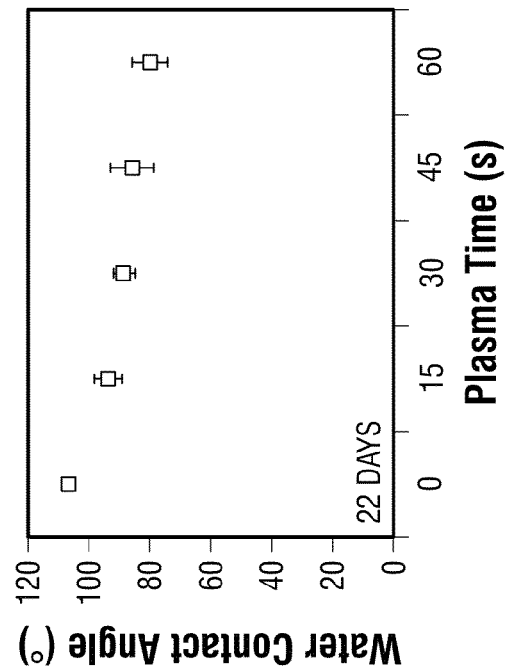
Figure 13C:
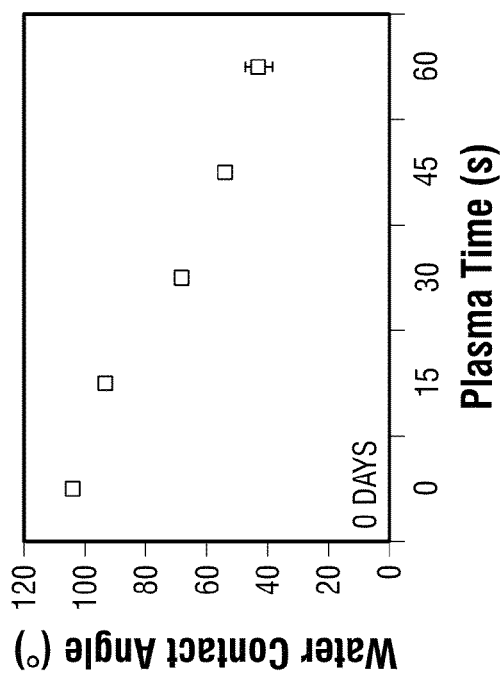
Figure 13D:
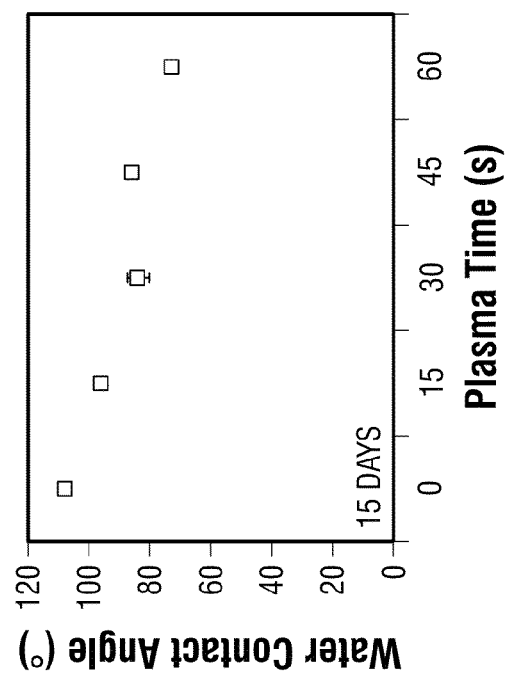
Figure 13E:
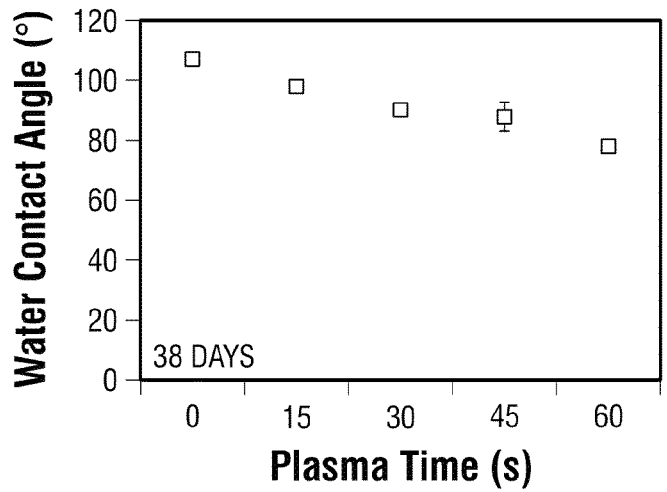
Figure 14A:
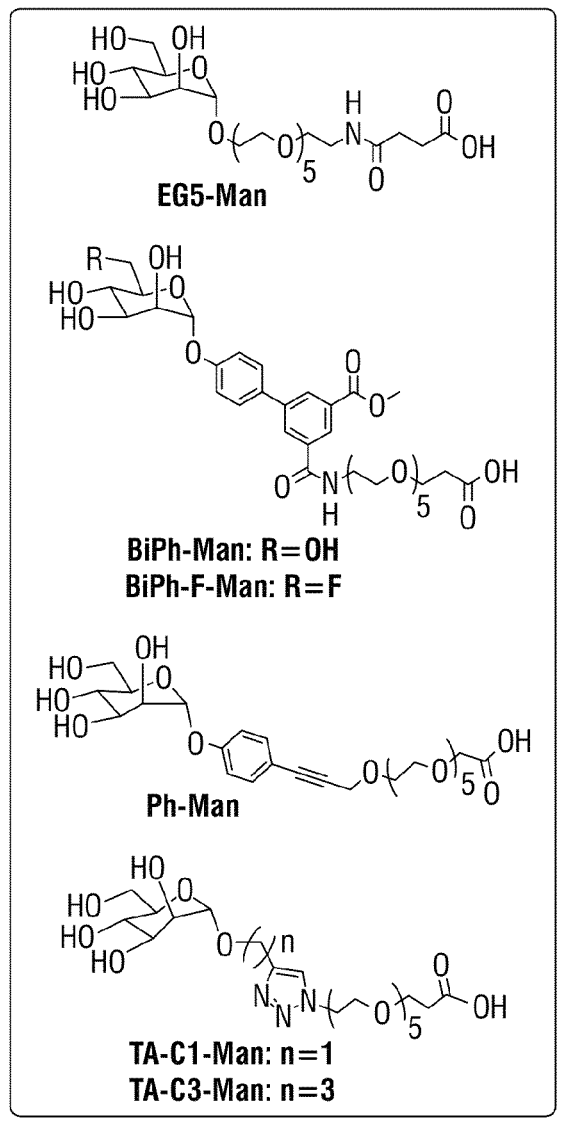
Figure 14B:
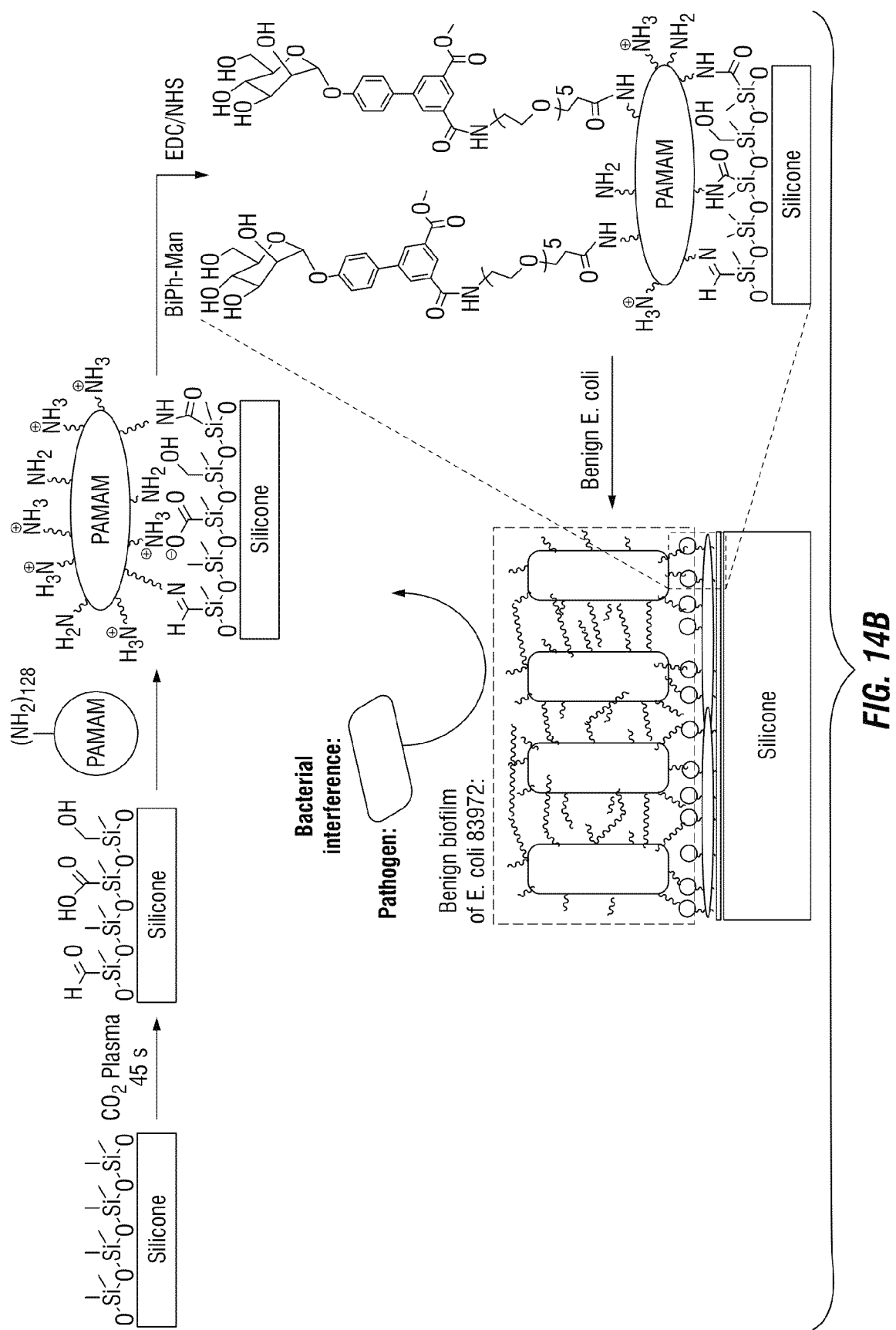
Figure 15A:
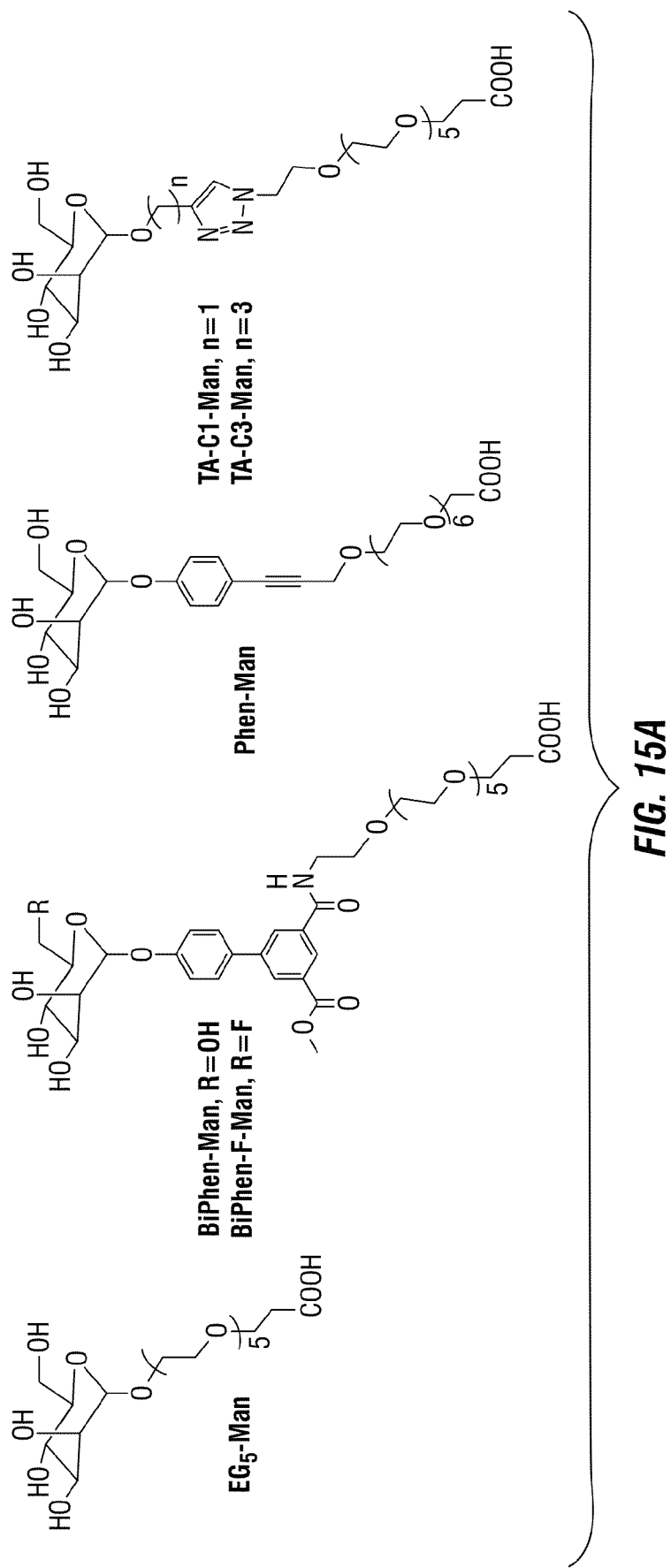
Figure 15B:
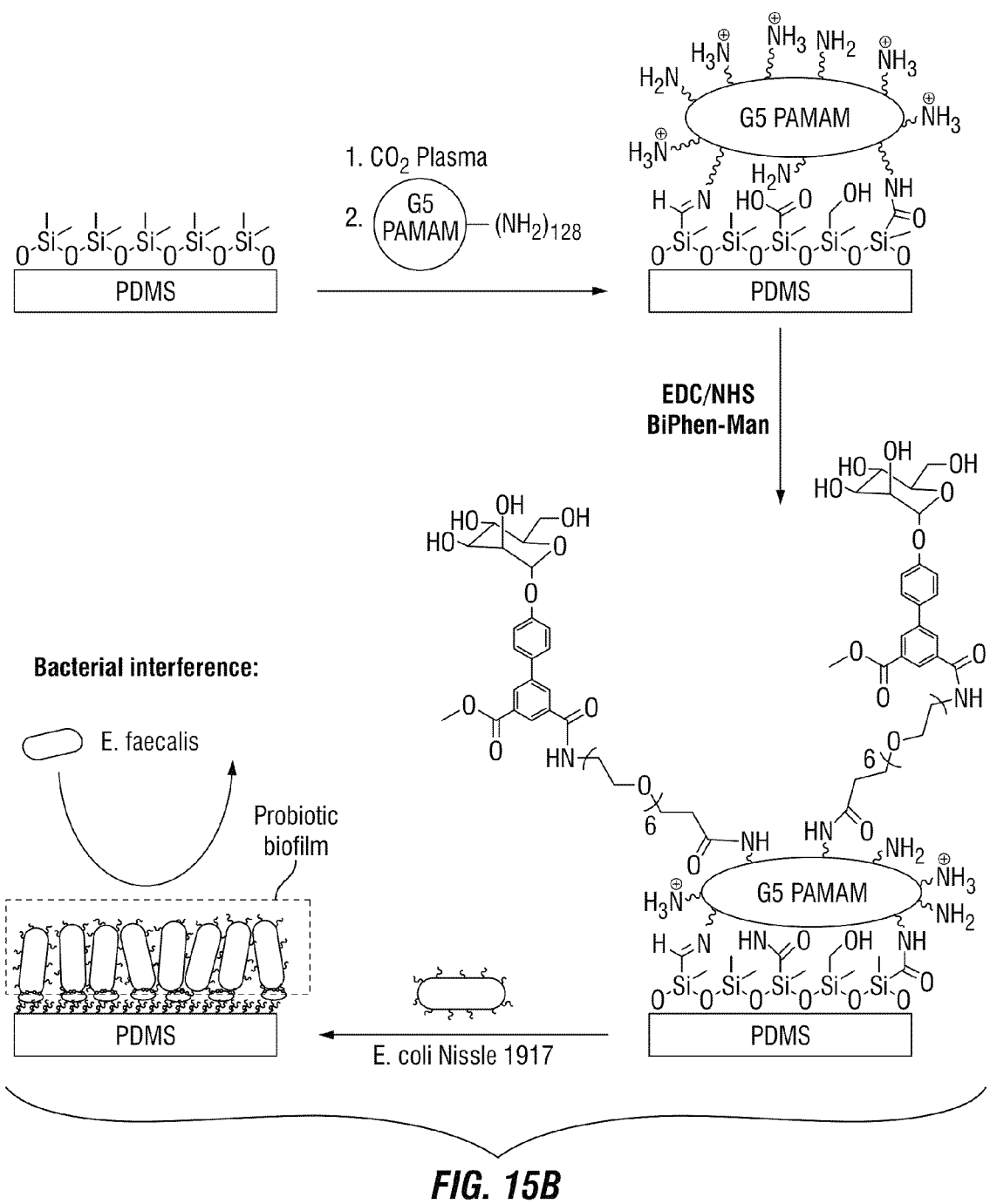
Figure 16:
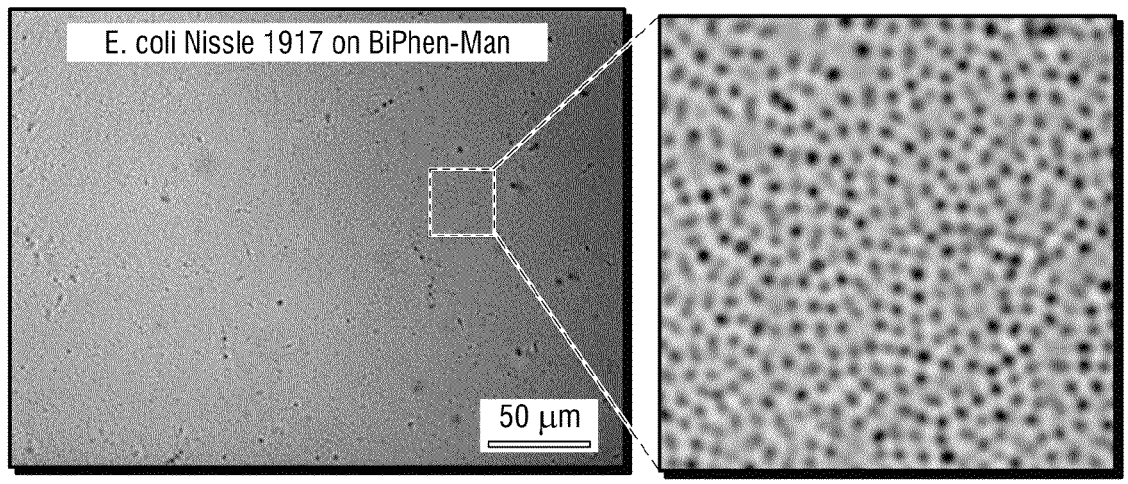
Figure 17A:
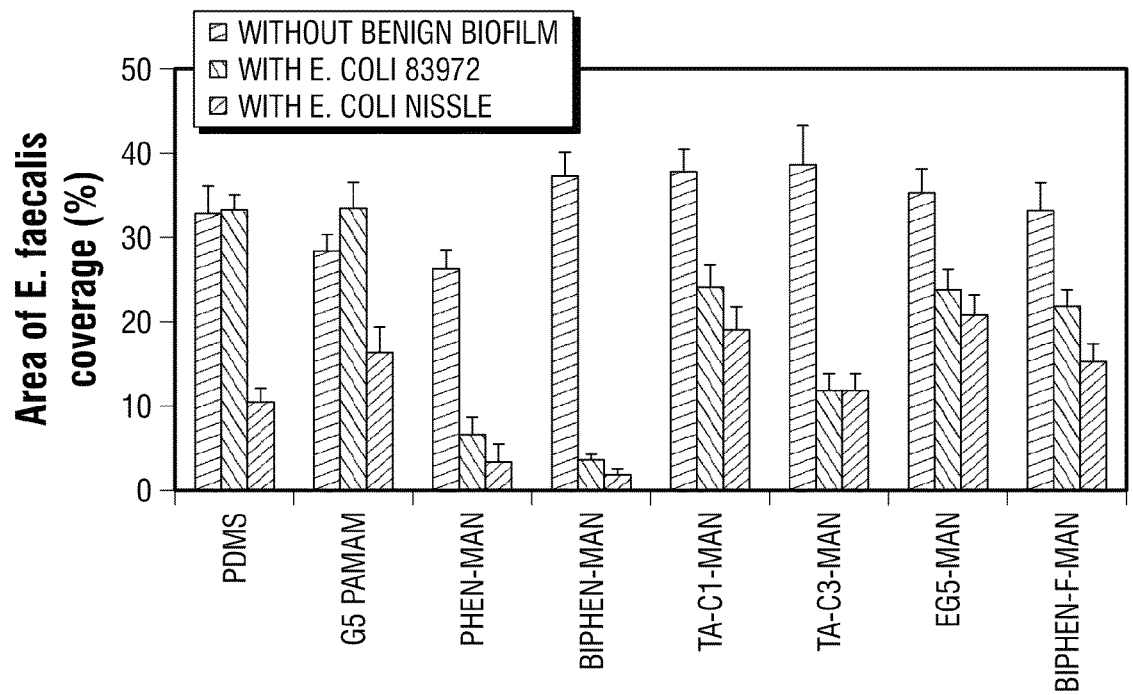
Figure 17D:
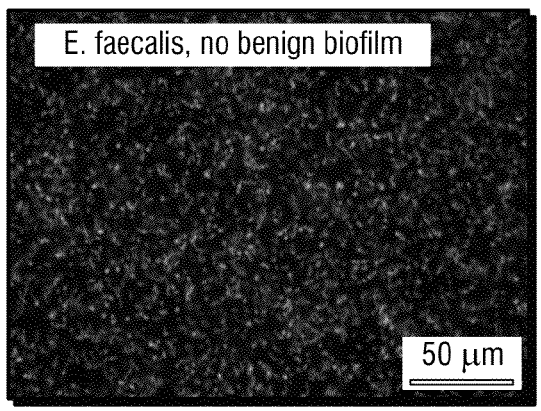
Figure 17D:
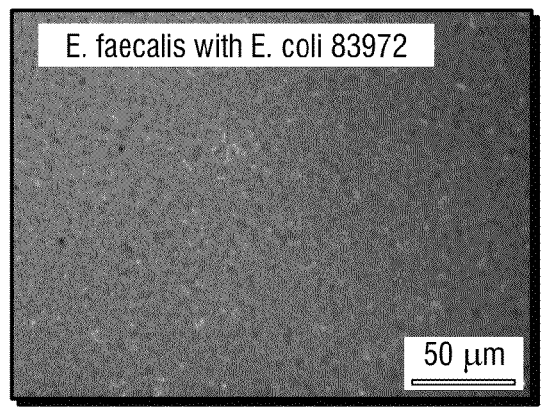
Figure 17D:
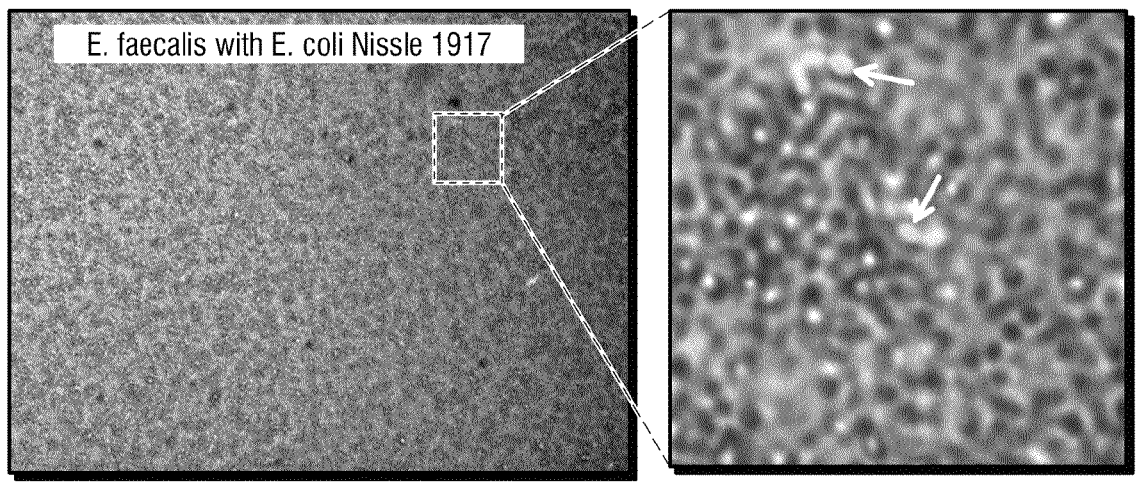
Figure 18A:
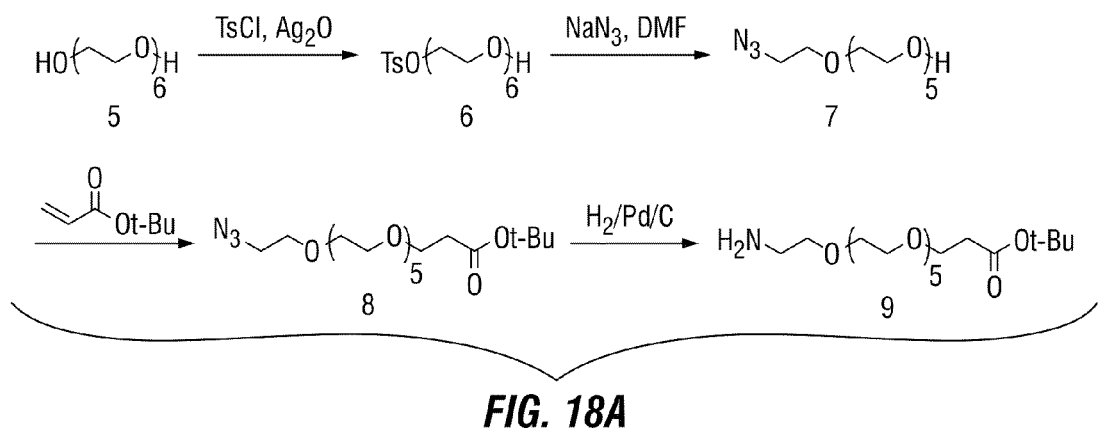
Figure 18B:
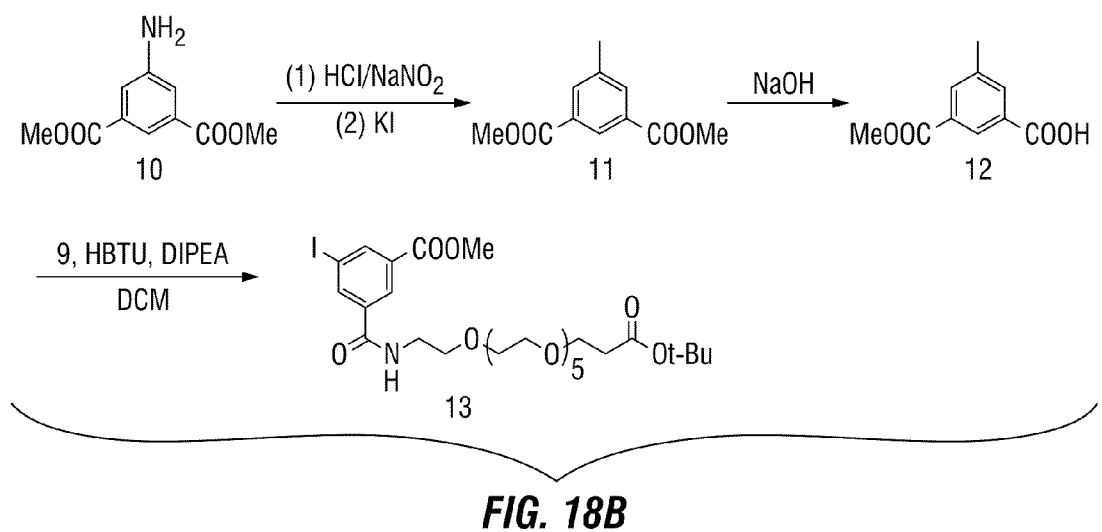
Figure 18C:
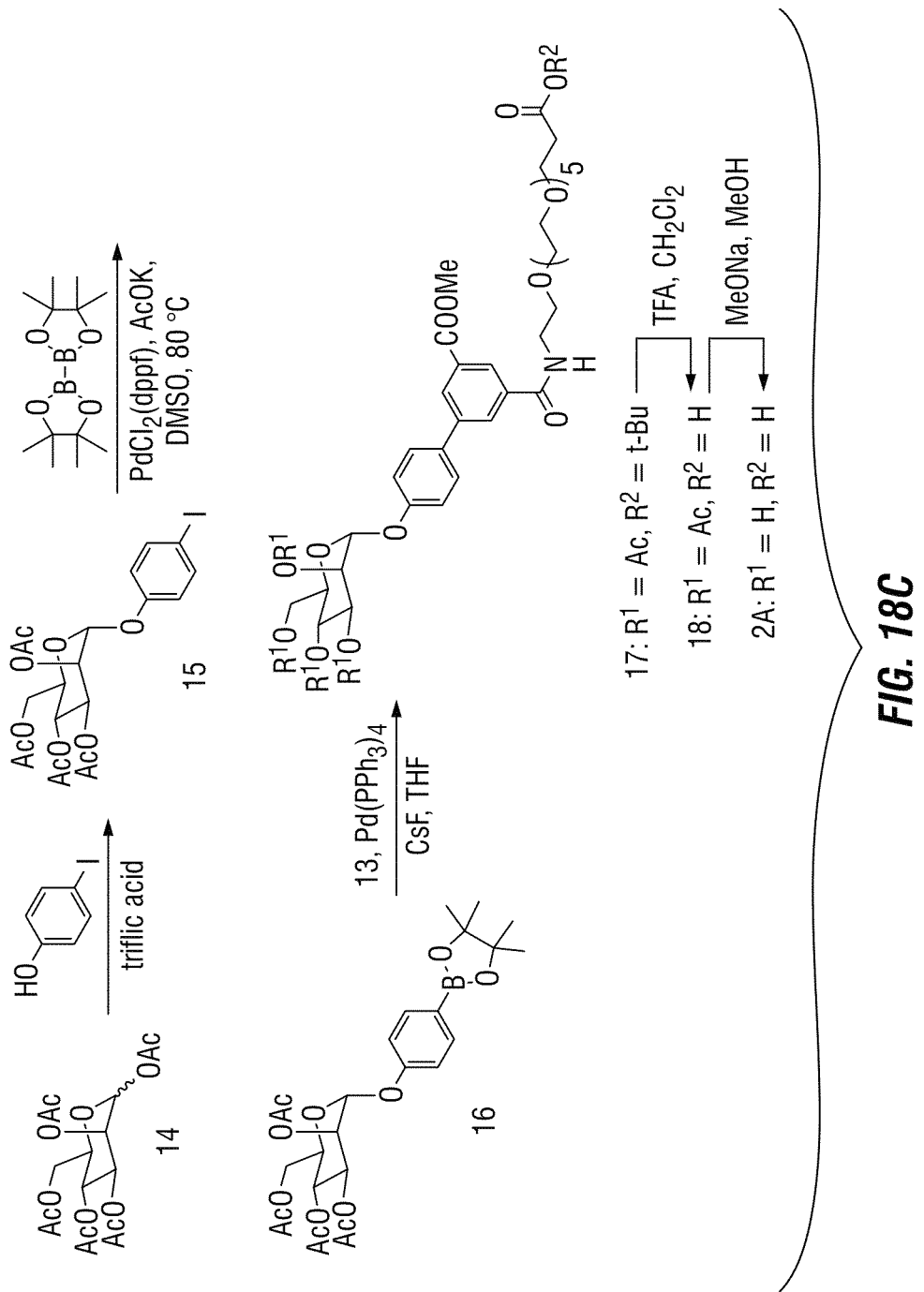
Figure 19:
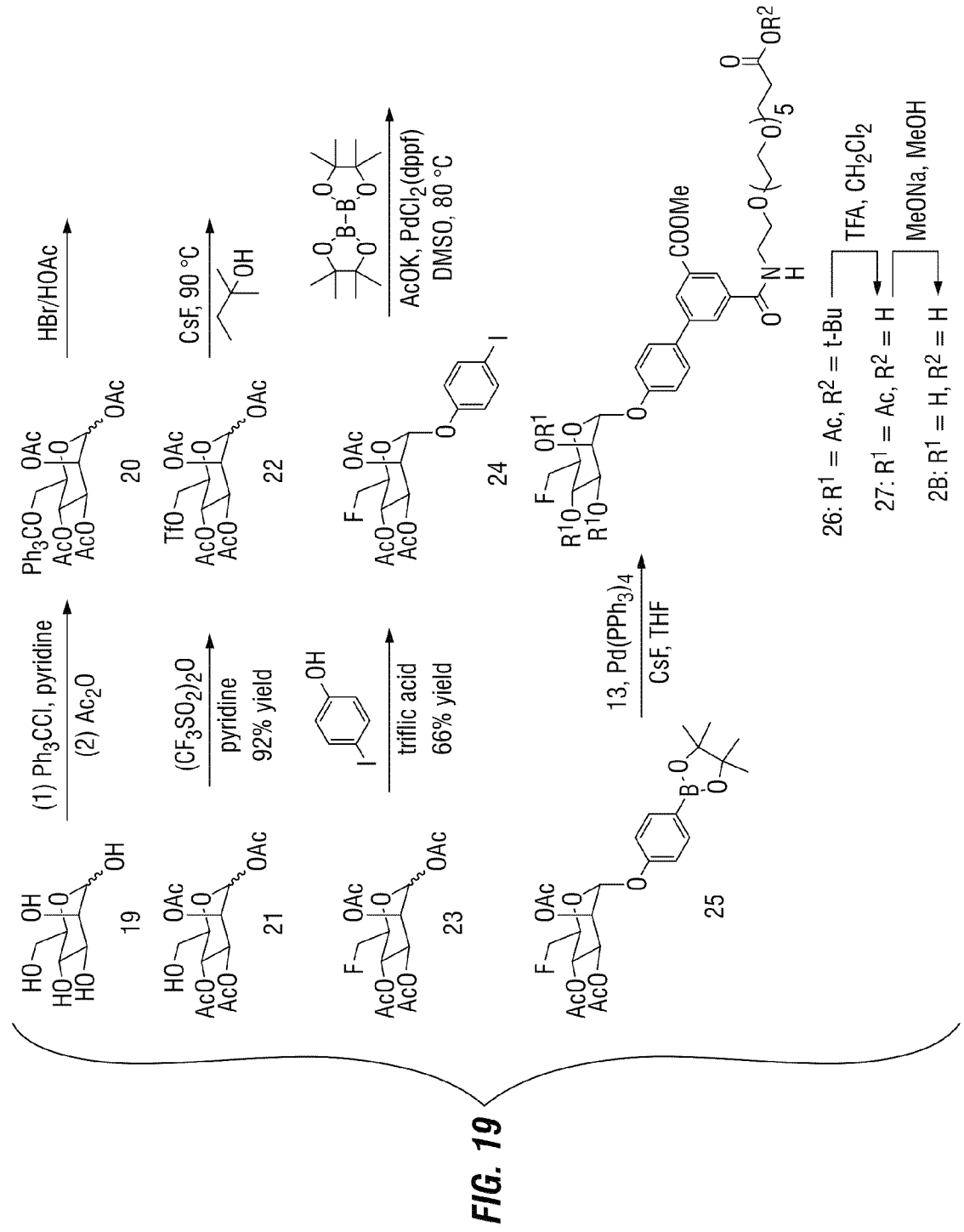

with or (A, D) without pre-formed *E. coli* 83972 on (A-C) PDMS and (D-F) $M_{E45}$ surfaces, where the benign bacteria were grown for (B, E) 18 h or (C, F) 48 h on the PDMS and mannose surfaces, and (G) results representing the mean of at least 3 experiments where 10 fields were imaged for each sample surface;

FIG. 8 depicts monitoring of PAMAM density by (A) XPS and (B) advancing water contact angles of the PDMS and PAMAM (PP) surfaces measured over a period of 36 or 38 days storage in PBS, where the PAMAM dendrimers were attached via amidiation chemistry;

FIG. 9 depicts representative reflected brightfield images of fim+*E. coli* 83972 after 18 h incubation on (A-D) covalently-linked dendrimer surfaces ($PP_{15}$-$PP_{60}$, from left to right) and the corresponding (F-I) mannose ($MPP_{15}$-$MPP_{60}$, from left to right) surfaces;

FIG. 10 depicts bacterial interfence results for PDMS and $MPP_{45}$ surfaces pre-coated with benign *E. coli* 83972 for 1 or 2 weeks, where almost no *E. faecalis* adhered to all *E. coli* 83972 surfaces after 30 min exposure with challenge pathogen and grown for 24 h in fresh LB media, and representative results represent the mean of 2 experiments where 10 fields were imaged for each sample surface;

FIG. 11 depicts Scheme 1, preparation of a mannoside, shown as Mann-COOH in FIG. 1, and shown as EG5-Man in FIGS. 14 and 15, from Mann-$N_3$;

FIG. 12 depicts PAMAM Density versus Plasma time, where after the CO2 plasma, samples were immediately immersed in 1 mg/mL G5 PAMAM solution in PBS buffer for 1 h, washed with Millipore water and dried with a flow of argon. Measurement was taken after immersion in PBS for 0, 8, 15 and 36 days;

FIG. 13 depicts Water Contact Angle versus Plasma time, where after the CO2 plasma, samples were immediately immersed in 1 mg/mL G5 PAMAM solution in PBS buffer for 1 h, washed with Millipore water and dried with a flow of argon. Measurement was taken after immersion in PBS for 0, 8, 15, 22 and 36 days;

FIG. 14 depicts a scheme for the immobilization of various mannosides on the PAMAM-modified PDMS to promote the formation of densely packed and stable biofilms of *E. coli* 83972 for the effective prevention of adherence and colonization of pathogens, such as *E. Faecalis*;

FIG. 15 depicts a scheme for the immobilization of various mannosides on the PAMAM-modified PDMS to promote the formation of densely packed and stable biofilms of *E. coli* Nissle 1917 for the effective prevention of adherence and colonization of pathogens, such as *E. Faecalis*;

FIG. 16 depicts a representative reflected brightfield image of *E. coli* Nissle 1917 on BiPhen-Man surface showing almost a complete bacterial coverage of the surface after incubation for 5 days, where the relatively flat surface consists of dot-like features measured ~1 μm as shown by the red lines on the magnified image, indicating a vertical orientation of the bacteria in the biofilms on this surface;

FIG. 17 depicts (a) Summary of bacterial interference results after 11 days using *E. faecalis* as challenge pathogen. The data represent the mean of at least 2 experiments where 10 fields were imaged for each surface, (b) representative green fluorescence image of bacterial adherence by *E. faecalis* on BiPhen-Man surfaces after 11 days, with representative overlay of reflected brightfield and green fluorescence images after prolonged bacterial interference against *E. faecalis* (white arrows) for 11 days using pre-formed biofilms of (c) *E. coli* 83972 or (d) *E. coli* Nissle 1917 on BiPhen-Man surfaces;

FIGS. 18A, 18B, and 18C depict a scheme for preparation of a biphenyl mannoside, compound 2a, also denoted as BiPhen-Man, where R=OH, in FIGS. 14 and 15;

FIG. 19 depicts preparation of another biphenyl mannoside, compound 2b, also denoted as BiPhen-Man, where R=F, in FIG. 14, and BiPhen-F-Man in FIG. 15.

Figure 20:
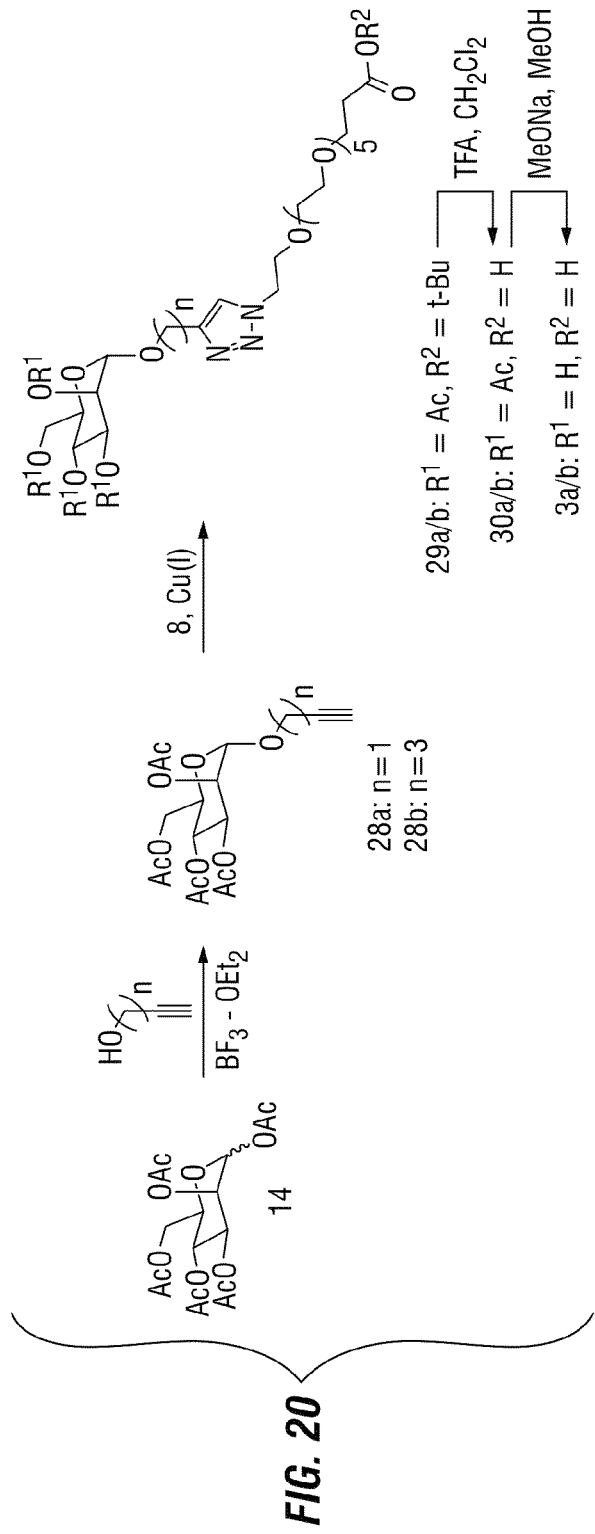
Figure 21:
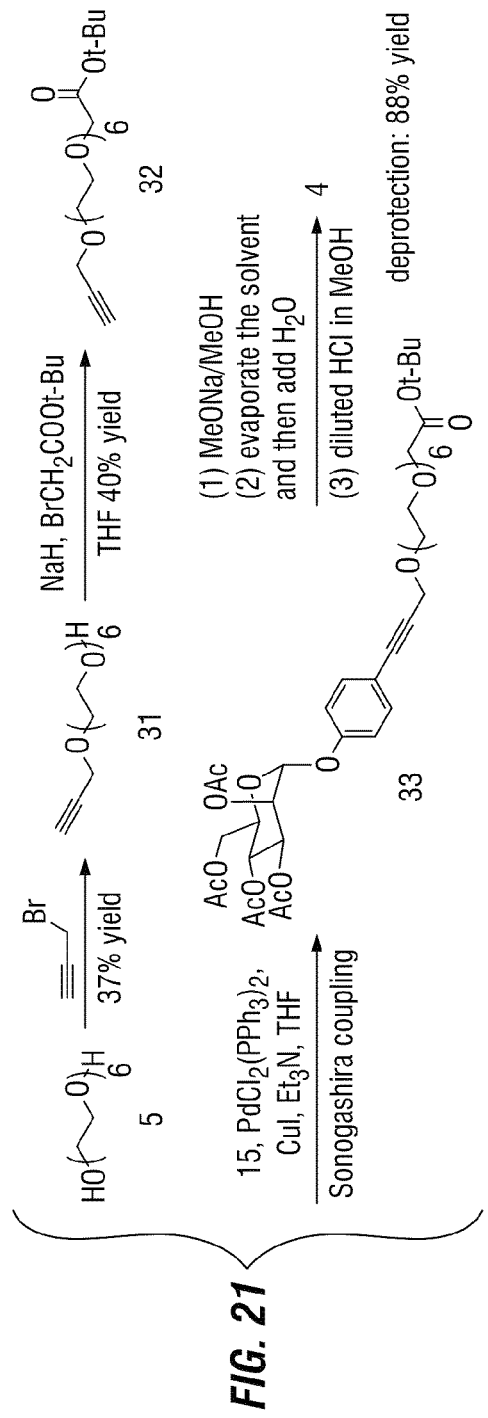

FIG. 20 depicts preparation of a triazolylalkyl mannoside, compound 3a, also denoted as TA-C1-Man in FIGS. 14 And 15, and another triazolylalkyl mannoside, compound, 3b, also denoted as TA-C3-Man in FIGS. 14 and 15; and FIG. 21 depicts preparation of an phenyl mannoside, compound 4, also denoted as Ph-Man in FIG. 14 and Phen-Man in FIG. 15.

DETAILED DESCRIPTION

According to some embodiments, the present invention discloses a novel, first-of-its-kind, method for the modification of inert silicone-based polymers (such as PDMS) with biologically active molecules, such as mannose derivatives. The disclosed method also used includes the biofunctionalization of the modified PDMS surface for use in silicone-based biomedical devices. Silicones are among the most widely used polymeric materials in medical devices, including orthopedic, ophthalmic and aesthetic devices, catheters, drains and shunts [50-52]. However, silicone surfaces are composed of inert alkylsiloxane moieties, thus need to be activated prior to the covalent attachment of biomolecules. The current invention also discloses an efficient method for incorporating a high density of amino groups on PDMS surfaces, allowing for attachment of a wide variety of biomolecules. As an example demonstrated in the examples, a mannose derivative was covalently attached to the surface. This method provided a mannose-presenting thin film platform on PDMS that greatly increased the coverage and stability of the benign biofilms of fim+*E. coli* 83972, or *Escherichia coli* Nissle 1917. We also demonstrated that the high coverage of the benign biofilms are necessary to nearly completely inhibit the colonization of the uropathogen *E. faecalis*. The present invention finds broad applications in biomedical devices, including implantable devices.

According to some embodiments, the present invention relates to a versatile and practical method for the biofunctionalization of poly(dimethylsiloxane) (or PDMS) under mild $CO_2$ plasma treatment followed by the attachment of generation 5 poly(amido amine) (or G5 PAMAM) dendrimer to create an amino-terminated platform with remarkable long-term stability against pathogen colonization. The present invention is also well adapted for the attachment of other structures, such as carboxy-terminated mannose derivatives, to the platform. The resulting mannose-presenting PDMS surfaces are shown to significantly enhance the adherence and biofilm formation of the benign fim+*Escherichia coli* 83972, or *Escherichia coli* Nissle 1917, which limits the colonization of pathogens. Such approach, also referred to bacterial interference is a promising strategy that uses pre-established biofilms of benign bacteria to serve as live, protective coating against pathogen colonization.

According to some embodiments, the present invention shows a novel versatile and practical method for biofunctionalization of PDMS based on mild $CO_2$ plasma treatment followed by simple attachment of PAMAM dendrimer to create an amino-terminated platform with remarkable long-term stability. We then attached a carboxy-terminated mannose derivative to the platform. The resulting mannose-presenting PDMS surfaces enhanced the adherence and biofilm formation of the benign fim+*Escherichia coli* 83972.

The mild $CO_2$ plasma treatment has advantages in comparison to oxygen plasma. Conventional methods for surface activation of polymers are mostly based on oxygen ($O_2$) plasma. However, we have found that oxygen plasma treatment of silicone polymers leads to substantial degradation/fragmentation of the polymers, even using a low power (<7 W) and short duration (1-5 seconds) which are difficult to control. There is no report on the use of $CO_2$ plasma to activate silicone surfaces, which is reactive to amines.

Another innovation in this application is the use of polyamines, such as PAMAM dendrimers and polylysine, to cross-link the activated and partially degraded silicone polymers. Adsorption of the dendrimer after $CO_2$ plasma activation is desirably immediately. According to some embodiments, immediately is as soon as practicable, more particularly within a few minutes. According to some embodiments, immediately is within a minute, more particularly within 30 seconds, still more particularly within 10 seconds, yet more particularly within 5 seconds. Without immediate treatment of the surface after the $CO_2$ plasma activation, we found that the hydrophilicity of the surface rapidly decrease, indicated the rapid rearrangement of the polar groups (carboxylic acid, aldehydes and alcohols) into the bulk or dissolution into the aqueous solution. In sharp comparison, the rapid treatment of the activated surfaces with PAMAM dendrimers led to surfaces presenting amine that were stable for weeks in aqueous solution, indicating the activated polymers are cross-linking by the polyamine, forming a stable network presenting the amino groups on the surface.

It will be understood that PDMS is illustrative of silicones. Further, G5 PAMAM) dendrimer is illustrative of an amino-terminated cross-linking dendrimer. Still further, mannose is illustrative of a ligand.

These pre-established biofilms of the benign bacteria were remarkably stable even under challenging by a high initial concentration ($10^5$ CFU/mL) of the uropathogenic $E.$ $faecalis$. Furthermore, the benign biofilms reduced the adherence of $E$ $faecalis$ on the mannose surface by 104-fold after 72 h, while the benign bacteria on the unmodified substrate by only 5.5-fold. More specifically, this invention clearly demonstrated the great importance of the establishment of a dense, stable biofilm of the benign bacteria prior to bacterial interference. The strategy presented in this work may be extended to modify silicone-based medical devices for preventing pathogenic biofilm formation leading to infection. The bacterial interference approach offers great potential in solving bacterial infection problems, particularly those associated with prolonged use of medical devices where conventional attachment of antimicrobials has been restricted by the development of microbial resistance.

While this disclosure focuses on the use of one type of mannose derivative for the modification of silicone surfaces in order to enhance the coverage and stability of benign biofilms, other carbohydrate derivatives with suitable linkers, including but not limited to those containing alkyl, and/or one or multiple arylene units with various substitutents, and/or oligo(ethylene glycol) are also well suited.

While the invention described herein specifically focuses on a versatile method for biofunctionalization of PDMS-based films under mild $CO_2$ plasma treatment followed by the simple attachment of PAMAM dendrimer to create an amino-terminated platform with remarkable long-term stability, one of ordinary skills in the art, with the benefit of this disclosure, would recognize the extension of the approach to other broad variety of systems.

The following examples are included to demonstrate particular embodiments of the present invention. It should be appreciated by those of skill in the art that the methods disclosed in the examples that follow merely represent exemplary embodiments of the present invention. However, those of skill in the art should, in light of the present disclosure, appreciate that many changes can be made in the specific embodiments described and still obtain a like or similar result without departing from the spirit and scope of the present invention.

EXAMPLES

A preferred embodiment of the present invention describes the general approach of this invention as illustrated in FIG. 1. Step (A) relates to the preparation of mannose-presenting silicone (PDMS) surfaces by $CO_2$ plasma treatment for 15, 30, 45, 60 seconds respectively to provide the activated surfaces $P_n$ (n=plasma treatment time), followed by immersion in a solution of G5 PAMAM dendrimers containing about 128 $NH_2$ groups, leading to the corresponding amino-terminated PAMAM surfaces $PP_n$, which is then followed by the attachment of Mann-COOH to afford the corresponding mannose-modified silicone surfaces $MPP_n$. Step (B) relates to the preparation of benign biofilms of $E.$ $coli$ 83972 and the demonstration of bacterial interference, i.e., the exclusion of pathogens from the benign biofilm, using $E.$ $faecalis$ as a model.

Oxygen ($O_2$) plasma has been commonly used on inert silicone to generate hydrophilic functional groups, primarily silanols on the surface [58-61]. However, $O_2$ plasma is often accompanied by an undesirable, fast recovery to full hydrophobic surface. The loss of hydrophilicity over time, known as hydrophobic recovery, is a common phenomenon after plasma treatment of silicone [62, 63]. It is a major problem for surface functionalization of silicone polymers.[53-56] Several mechanisms to explain hydrophobic recovery had been proposed [62, 64], including the migration of the native polymer from the bulk to the surface to replace the fragmented, oxidized polymers on the surface [54, 58]. This phenomenon significantly diminishes the stability of the surface functionalization of silicone. In search for a milder method, we found that the seldom used of carbon dioxide plasma might be a potential alternative to activate organic/polymer surfaces [65-69]. Not only does it greatly reduce the degradation of silicone polymer [70], it also tends to generate more carboxylic acids on both alkylsiloxane monolayers [65] and polyethylene surfaces [68, 69]. Moreover, successive $CO_2$ plasma treatments afforded fully wettable surfaces [68, 70], which is not achievable with $O_2$ plasma. The current invention systematically optimizes the $CO_2$ plasma exposure times (FIG. 1) prior to attaching the PAMAM dendrimers, and the resulting plasma-treated surfaces are systematically characterized by XPS and water contact angle measurements.

Figure 2A:
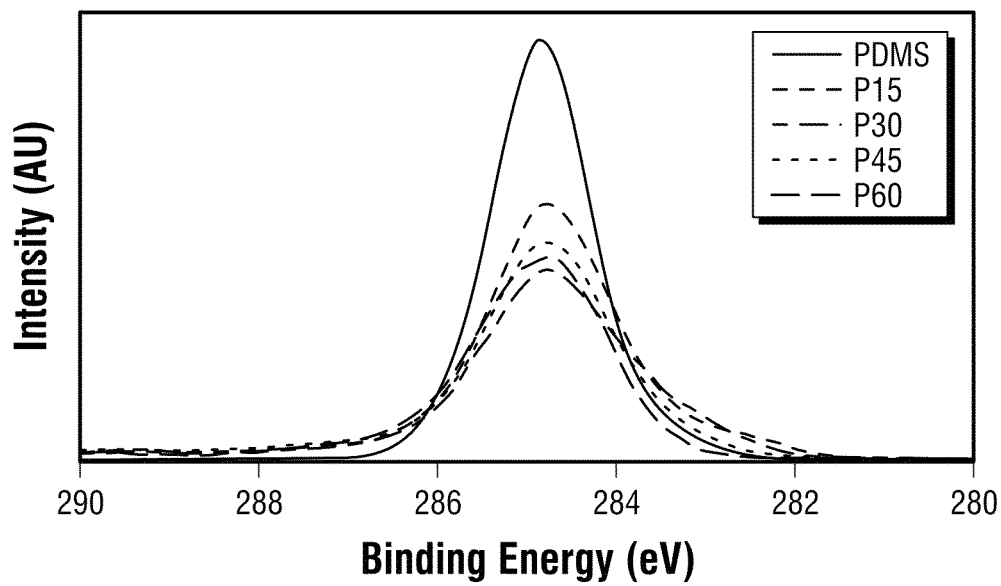
FIG. 2 depicts (A) C1s and (B) Si2p narrow scan XPS spectra of PDMS and oxidized PDMS ($P_{15}$-$P_{60}$) surfaces.
Figure 2B:
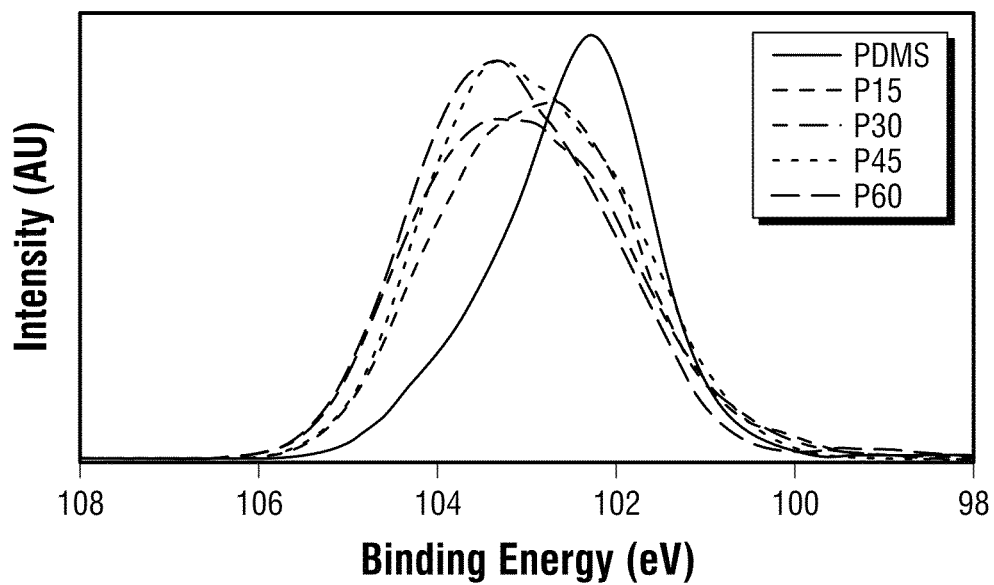

A preferred embodiment of the present invention reveals the oxidation of PDMS layers using $CO_2$ plasma. The C1s and Si2p narrow scan spectra of the oxidized PDMS are illustrated in FIGS. 2a and 2b, respectively. Evidence of oxidation was observed with the appearance of small peaks at binding energies higher than 284.8 eV in the C1s narrow scan spectra compared to untreated PDMS (FIG. 2a), corresponding to C—O (286.2 eV), C=O (288.0 eV) and O—C=O (289.2 eV). On the other hand, silicone was also oxidized as shown by the increase in the peak area (FIG. 2b) towards a higher binding energy (~104 eV). Partial degradation of carbon can also be observed as given by the decrease in atomic concentration of carbon. This can be explained by the possible removal of the methyl groups during the oxidation of the silicone and replacement by hydroxyl groups. Similar to the report in the literature [62], a fully wettable surface was obtained after 45 s of $CO_2$ plasma treatment ($P_{45}$) as given by the measured advancing water contact angle (<10°) shown in Table 1. However, relatively shorter $CO_2$ plasma exposure times ($P_{15}$ and $P_{30}$) led to only partially wettable surfaces (Table 1).]

TABLE 1 characterization of PDMS, plasma-treated PDMS (P) and PAMAM-modified surfaces (PP) using XPS and water contact angle.

| Surface | [a]PAMAM density (E+12 molecules/cm$^2$) | | Advancing water contact angles, ° | |
|---|---|---|---|---|
| | 0 days | 36 days | 0 days | 38 days |
| PDMS | | | 104 ± 1 | 107 ± 1 |
| $P_{15}$ | | | <10 | |
| $P_{30}$ | | | <10 | |
| $P_{45}$ | | | 11 ± 1 | |
| $P_{60}$ | | | 28 ± 4 | |
| $PP_{15}$ | 1.5 ± 0.1 | 1.0 ± 0.3 | 93 ± 3 | 98 ± 1 |
| $PP_{30}$ | 2.9 ± 0.1 | 1.8 ± 0.2 | 68 ± 1 | 90 ± 4 |
| $PP_{45}$ | 3.4 ± 0.1 | 1.9 ± 0.1 | 54 ± 3 | 88 ± 3 |
| $PP_{60}$ | 3.3 ± 0.1 | 2.0 ± 0.5 | 43 ± 1 | 78 ± 1 |

[a]See Supplementary information for the equation used to estimate the density, assuming that the adsorbed PAMAM molecules were be flat with a uniform thickness and that the nitrogen atoms are evenly distributed along the surface.

Another novelty of this invention is the use of the generation 5 amino-terminated poly(amidoamine) (G5 PAMAM) dendrimers to cross-link the activated silicone polymers on the surface, thereby reducing their diffusion away from the surface. In addition, G5 PAMAM dendrimers possess about 128 amino groups on its periphery [71-73], which are used to immobilize them onto the oxidized PDMS surface and for bioconjugation (FIG. 1). Immobilization of the dendrimers was achieved by immersing the activated silicone substrate in a PBS solution of PAMAM for 1 h. Alternatively, we also attached PAMAM via amidation in the presence of activating agents (EDC/NHS). Although the nature of the bonding of the dendrimers on the samples prepared without EDC/NHS remains unclear, it possibly involves a combination of multiple electrostatic interactions and covalent bonding through imine formation as illustrated in FIG. 1. The surfaces before and after modification were characterized by XPS and water contact angle measurements, as illustrated in FIGS. 3, 8, 12, and 13. The results from XPS confirmed the presence of PAMAM by the appearance of N1s peak at around 400 eV in the wide scan XPS spectra corresponding to both amine and amide nitrogen in PAMAM as well as increase in the amide C=O peak at 288 eV in the deconvoluted C1s narrow scan spectra. The peak areas corresponding to the oxidized carbon species (286.5 and 288 eV, corresponding to C—O and C=O, respectively) in the C1s spectra of the PAMAM surfaces were also observed to increase with increasing plasma treatment time, signifying a greater density of attached dendrimers for longer exposure to $CO_2$ plasma. The PAMAM surface density was determined by XPS using a reference monolayer of bis(11-azidoundecyl)disulfide, which is an azide-terminated alkyl monolayer on gold, with a known density of nitrogen on the film surface (data not shown). The chemisorbed PAMAM molecules on the surface was presumed to be a compressed ellipsoidal shape similar to those in a monolayer [74]. Considering the nominal diameter of G5 PAMAM, which is 54 Å, the cross-sectional area occupied by each G5 PAMAM dendrimer is 2290 Å$^2$ [75]. Thus, the density of PAMAM to completely cover a 1 cm$^2$ area is estimated to be $4.4 \times 10^{12}$ molecules/cm$^2$, and the coverage of the PAMAM on the oxidized PDMS surfaces ranges from 34% to 77%. The advancing water contact angles were obtained right after PAMAM attachment and the results are summarized in Table 1. The values were comparable to a reported initial water contact angle (40°±2°) of a generation 4 PAMAM dendrimer with a relatively high coverage (82.2%) [76]. The hydrophilicity of the PAMAM surfaces also increased with the plasma treatment time, which supported a higher PAMAM density for the surface with longer $CO_2$ plasma exposure ($PP_{60}$).

Figure 3A:
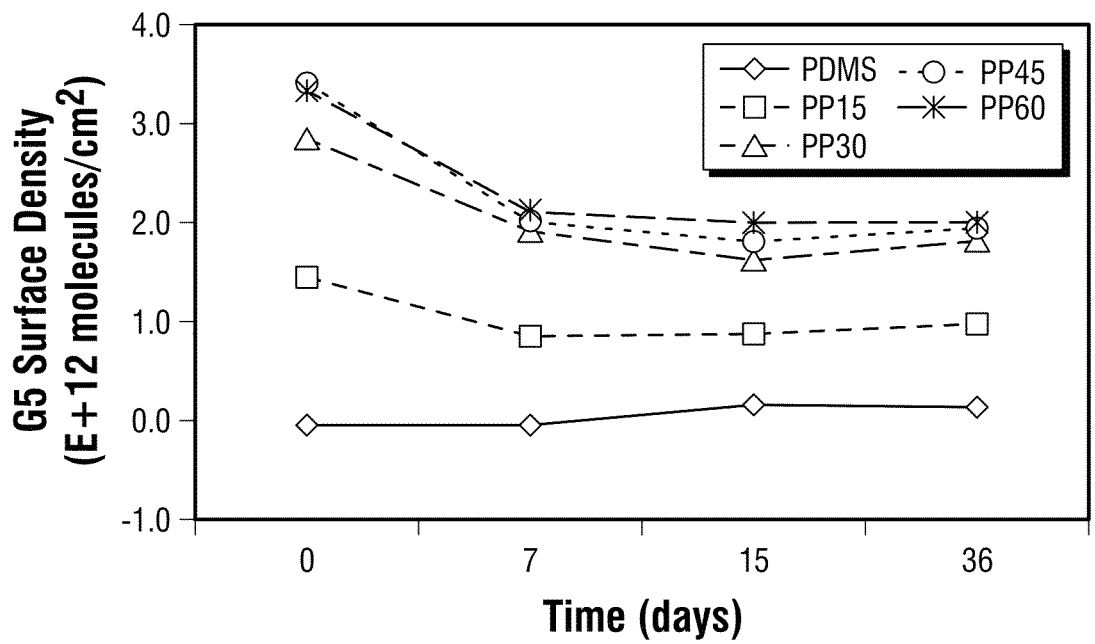
FIG. 3 depicts Monitoring of (A) PAMAM density by XPS and (B) advancing water contact angles of the PDMS and PAMAM (PP) surfaces measured over a period of 36 or 38 days storage in PBS.
Figure 3B:
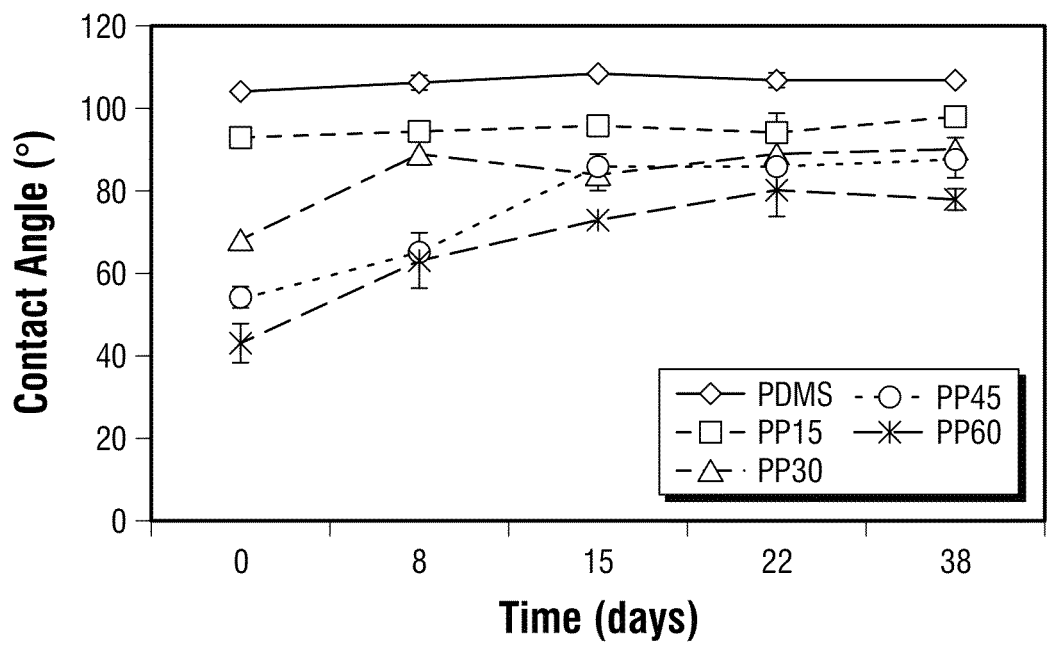
Figure 4A:
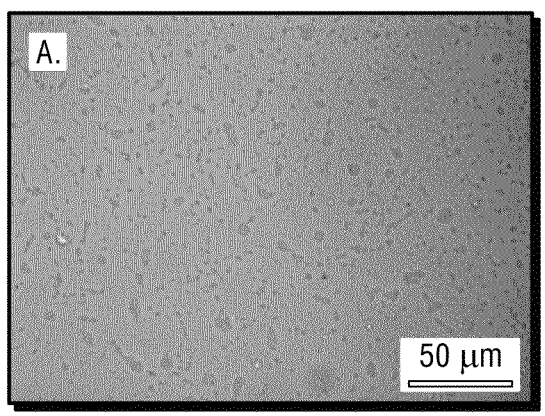
FIG. 4 depicts representative reflected brightfield images of fim+E. coli 83972 after 18 h incubation on (A, B) PDMS and (C, D) $MPP_{45}$ surfaces. PDMS were either (A) freshly prepared (0 days) or (B) stored in PBS for 40 days. $MPP_{45}$ surfaces were derived from (C) freshly prepared (0 days) or (D) stored in PBS for 40 days $PP_{45}$ surfaces, and (E) results representing the mean of at least 2 experiments where 10 fields were imaged for each sample surface.
Figure 4B:
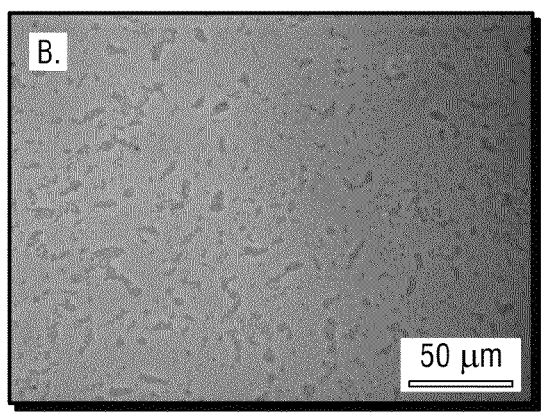
Figure 4C:
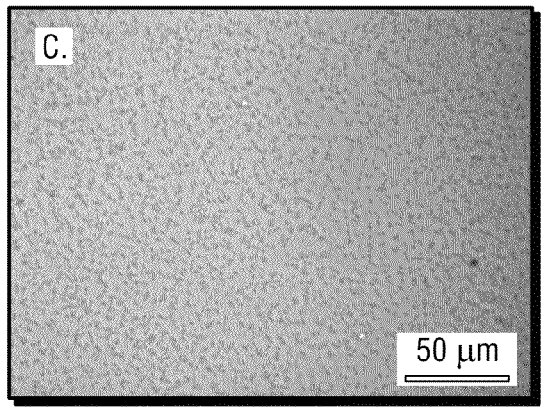
Figure 4D:
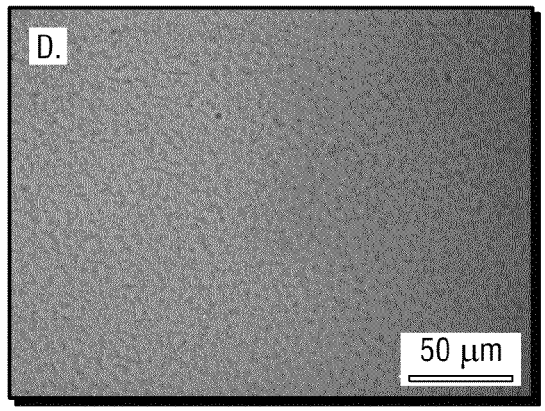
Figure 4E:
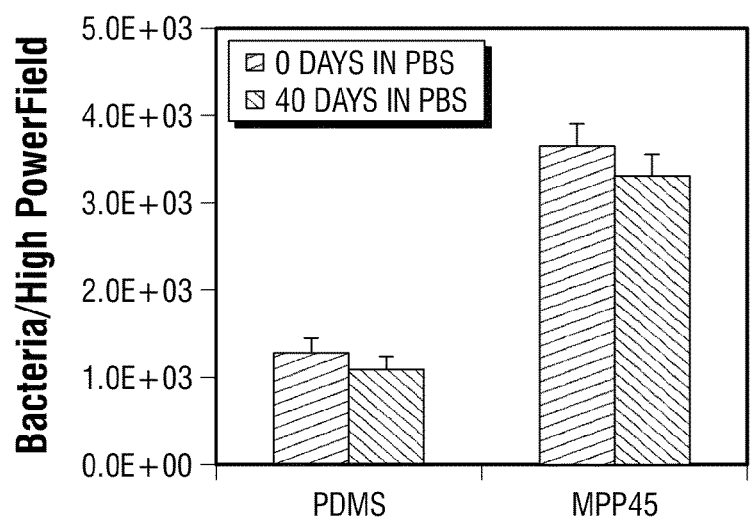
Figure 5C:
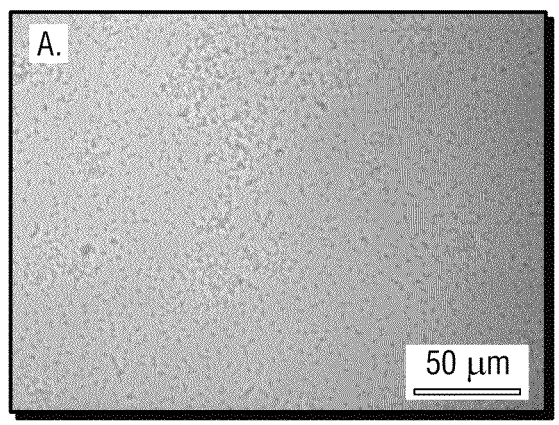
FIG. 5 depicts representative reflected brightfield images of fim+E. coli 83972 after 48 h incubation on (A) PDMS and (B) $MPP_{45}$ surfaces, where the overlay of the red fluorescence represents membrane-compromised bacteria, (C) results representing the mean of at least 3 experiments where 10 fields were imaged for each sample surface, and (D) results representing the mean of 3 experiments done in duplicates.
Figure 5C:
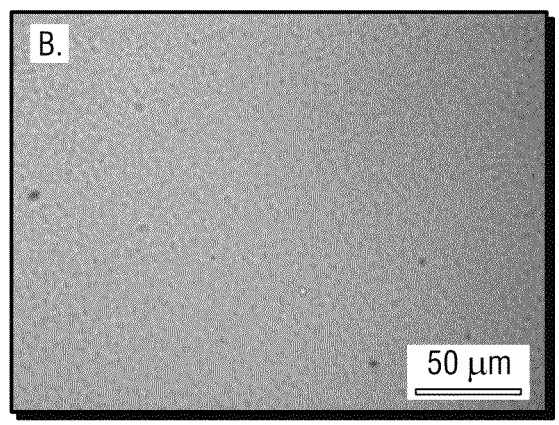
Figure 5C:
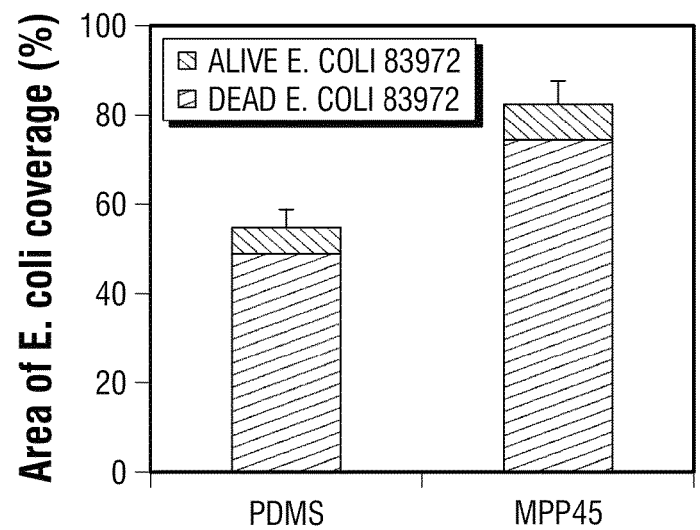
Figure 5D:
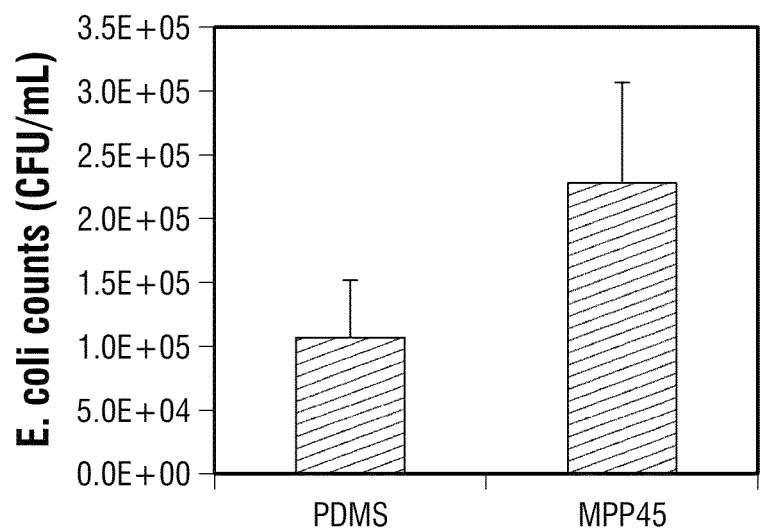

Another preferred embodiment of the present invention discloses the stability of adsorbed PAMAM on PDMS surfaces over time. The long-term stability of PAMAM films over 5 weeks in PBS solution was also monitored by XPS and contact angle measurements. FIG. 3a shows a huge drop in PAMAM density within 7 days in PBS, especially for $PP_{45}$ and $PP_{60}$, indicating desorption of some PAMAM moieties that were weakly adsorbed on the surfaces. Afterwards, the PAMAM densities were almost constant for over 5 weeks. Supporting these results were the contact angles measured for almost the same period of time. In FIG. 3b, it can be seen that the highest increase in advancing water contact angles was after the first 7 days. These results are consistent with the loss of most of the PAMAM moieties during the first week as observed from the calculated PAMAM densities using XPS. The incremental increase in the water contact angle for the PAMAM surface in the following days may be attributed to the hydrophobic recovery of PDMS. The diffusion of the untreated polymer to the surface from the bulk may have caused a slight covering of the PAMAM adsorbed on the surface rendering the hydrophobicity. Table 1 shows that even after 36 days, more than 50% of the PAMAM molecules remained on the surfaces, corresponding to a about 45% surface coverage. It should be noted, however, that the PAMAM density values did not vary with the $CO_2$ plasma exposure time except for $PP_{15}$, which had the least initial PAMAM density. These results imply that while a greater amount of carboxylic may presumably form with longer $CO_2$ plasma treatment time, it was not necessary to attach more PAMAM on the surface. Due to the multiple amino groups in the PAMAM, it could be potentially adsorbed even with a lower concentration of the carboxylic acid on the surface. Surprisingly, the final PAMAM densities were also comparable to the ones covalently-linked with EDC/NHS (Table 2). Thus, substantial amount of PAMAM coated on oxidized PDMS surface were remarkably stable over a long period of time (36 days) when stored in PBS.

TABLE 2

Characterization of PDMS, plasma-treated PDMS (P) and PAMAM-modified surfaces (obtained via amidation using EDC/NHS) (PP) using XPS and water contact angle.

| Surface | PAMAM density (E+12 molecules/cm$^2$) | | Advancing water contact angles, ° | |
|---|---|---|---|---|
| | 0 days | 36 days | 0 days | 38 days |
| $PP_{15}$ | 2.9 ± 0.1 | 1.5 ± 0.7 | 72 ± 2 | 93 ± 1 |
| $PP_{30}$ | 3.4 ± 0.3 | 1.8 ± 0.3 | 53 ± 4 | 92 ± 2 |
| $PP_{45}$ | 5.2 ± 0.1 | 1.7 ± 0.4 | 45 ± 4 | 85 ± 2 |
| $PP_{60}$ | 5.7 ± 0.7 | 1.7 ± 0.1 | 37 ± 4 | 92 ± 4 |

Another preferred embodiment of the present invention discloses the adherence of fim+*E. coli* 83972 to mannose units (MPP45), as illustrated by the representative reflected brightfield images of fim+*E. coli* 83972 after 18 h incubation on (A, B) PDMS and (C, D) MPP$_{45}$ surfaces (FIG. 4). PDMS were either (A) freshly prepared or (B) stored in PBS for 40 days. MPP$_{45}$ surfaces were derived from (C) freshly prepared or (D) stored in PBS for 40 days PP$_{45}$ surfaces. (E) Results represent the mean of at least 2 experiments where 10 fields were imaged for each sample surface.

In order to demonstrate the utility of the PAMAM-coated surfaces as a universal platform for attachment of biomolecules, we have prepared a mannose derivative (Mann-COOH) consisting of an oligo(ethylene)glycol (OEG) linker and a carboxylic acid terminal group, to serve as the ligand for the type 1 fimbriae that mediates the attachment of the benign fim+$E.$ $coli$ 83972 to the surface. OEG was used as a linker to minimize nonspecific adsorption of bacteria to the surfaces while the carboxyl group was for covalent attachment to the amino groups of the PAMAM via amidation. The resulting mannose-coated surfaces (MPP) were subjected to bacterial adherence assay using both the benign bacteria (fim+$E.$ $coli$ 83972) and the challenge pathogen ($E.$ $faecalis$). After a preliminary screening of the mannose-coated (MPP) surfaces derived from different PAMAM surfaces (PP), we selected MPP$_{45}$ as the mannose-presenting model surface to perform the succeeding bacterial adherence and interference experiments. In the first set of bacterial adherence experiments, we observed the attachment of the fim+$E.$ $coli$ 83972 to MPP$_{45}$ surfaces derived from PP$_{45}$ surfaces (FIG. 1), which have been freshly prepared or stored in PBS for 40 days and compare the results to the corresponding PDMS control. All the sample surfaces were incubated with a $10^5$ CFU/mL concentration of the benign bacteria for 18 h at 37° C. The results (at 18 h) were evaluated using a microscopy-based method and the selected brightfield images are shown in FIG. 4$a$-4$d$. Using the Nikon Elements software, the results of bacterial counting showed that the adherence of fim+$E.$ $coli$ 83972 to MPP$_{45}$ surfaces ($3.7 \times 10^3$ $E.$ $coli$/field) was increased by 2.2 fold compared to adherence to unmodified PDMS substrates ($1.3 \times 10^3$ $E.$ $coli$/field, *P<0.001, T-test). Surprisingly, the results for the MPP$_{45}$ surfaces derived from the PP$_{45}$ surfaces stored in PBS for 40 days showed no substantial difference from the freshly prepared surfaces for both PDMS and mannose surfaces (*P>0.1, T-test). Similarly, the MPP$_{45}$ surfaces ($3.3 \times 10^3$ $E.$ $coli$/field) resulted in better adherence than the PDMS surfaces ($1.1 \times 10^3$ $E.$ $coli$/field, *P<0.001, T-test). From the earlier results, we have shown that PAMAM densities decrease after storage in PBS for 36 days. However, since the results showed almost comparable attachment of the benign bacteria on the MPP$_{45}$ surfaces derived from the freshly prepared and PBS stored PP$_{45}$, it can be presumed that either a threshold mannose density was reached for bacterial attachment or comparable mannose densities were achieved regardless of the difference in PAMAM coverage. We had also compared the freshly MPP surfaces derived from PP surfaces stored in PBS for 40 days to their corresponding PP surfaces derived from amidation. Enhanced adherence was observed for the MPP surfaces than the PP surfaces while comparable attachment were seen among the MPP surfaces (FIG. 9).

FIG. 5 shows the representative reflected brightfield images of fim+$E.$ $coli$ 83972 after 48 h incubation (instead of 18 h) on (A) PDMS and (B) MPP$_{45}$ surfaces. The overlay of the red fluorescence represents membrane-compromised bacteria. (C) Results represent the mean of at least 3 experiments where 10 fields were imaged for each sample surface. (D) Results represent the mean of 3 experiments done in duplicates. The relatively short duration of the bacterial adherence (18 h) did not allow the benign bacteria to completely cover the mannose surface. Thus, we extend the incubation time to 48 h to permit further growth of the benign bacteria and to see whether it is capable to form biofilms on the mannose surface during this time. We hypothesize that in order for these benign bacteria to serve as a durable protective coating against the pathogens; they must form a dense (high coverage), stable biofilm on the surface. The results for the 48 h adherence assay are summarized in FIG. 5. Since counting individual bacterium as done in the previous set of experiments was impossible due to the formation of more bacterial aggregates that overlap each other in this case, the percent area covered by the bacterial aggregates per field was taken as the quantitative measure to compare the surfaces. The results showed enhanced adherence of the benign bacteria on the MPP$_{45}$ surface (FIG. 5$b$) compared with the PDMS surface (FIG. 5$a$) (1.5-fold increase in area, *P<0.00, T-test). However, compared to the results from the 18 h incubation with the benign bacteria, the enhancement of adherence was lower (1.5-fold versus 2.2-fold) during the 48 h adherence assay. We attribute this discrepancy to the limitation of the quantitative measure of the adherence in this case. During the 48 h incubation, while we have seen that the benign bacteria had increased adherence on the PDMS surface, a dense biofilm of benign bacteria was also found in the mannose surface. Most bacteria in the crowded biofilm on the mannose surface was observed to have changed their orientation to the vertical standing up position (circular) from the horizontal lying position (elongated) as mostly seen in the PDMS to maintain contact with mannose. This observation of the vertical orientation of the bacteria is remarkable. It was reported that the vertical orientation enhances motility of the bacteria which facilitates biofilm formation [77]. The difference on bacterial orientation caused an underestimation for bacterial adherence on the mannose surface by a factor of 2-3 as compared to the PDMS surface. In our attempt to have a more accurate quantification of the bacteria on the surface, we performed a plate-based adherence assay on both PDMS and MPP$_{45}$ surfaces. A detergent solution (0.01% SDS) and sonication (10 min) were used to detach the benign bacteria from the surfaces. The results are plotted in FIG. 5D. The benign bacteria showed better adherence to MPP$_{45}$ surfaces ($2.3 \times 10^5$ CFU/mL) by 2.3-fold compared with PDMS ($1.0 \times 10^5$ CFU/mL). This data still represent an underestimate of the adherence on the mannose surface due to strong binding of the bacteria to this surface resulting in incomplete detachment of the bacteria as revealed by microscopic images.

Another important concern for an effective bacterial interference is the viability of the benign bacteria on the surfaces. In order to address this concern, we have conducted a simple viability test via live/dead imaging using propidium iodide to detect the presence of bacteria with compromised cell membranes. While we have already shown earlier through the plate-based counting method the viable counts of the benign fim+$E.$ $coli$ on both MPP$_{45}$ and PDMS surfaces, this live/dead imaging procedure was performed due to the ease of screening all the PP and MPP surfaces rather than doing the more tedious plating. Using this simple test, the bacteria having compromised cell membranes (dead bacteria) show red fluorescence at 562-588 nm. The overlay of the red fluorescence with the brightfield images reflects the ratio of the dead to the live bacteria on the surfaces. Results showed that in both PDMS and MPP$_{45}$ surfaces, only few bacteria (<10%) were found to have compromised cell membranes (FIG. 5$a$-5$c$), signifying low toxicity to the benign bacteria. PAMAM dendrimers, on the other hand, have been reported to inhibit the growth of Gram negative bacteria [78, 79]. A modified minimum inhibitory concentration (MIC) assay [78] was used to test various concentrations (3.1-400 µg/mL) of the PAMAM dendrimer for antibacterial activity against the benign fim+*E. coli* 83972. The MIC value obtained is 200μ/mL, suggesting a very low toxicity for the unmodified PAMAM dendrimer to the benign bacteria. Even these PAMAM dendrimers might increase their local concentration on the surface, similar to $MPP_{45}$ and PDMS surfaces, the $PP_{45}$ surfaces gave similar results wherein ~10% of the adherent bacteria were found to have compromised cell membranes.

Figure 6C:
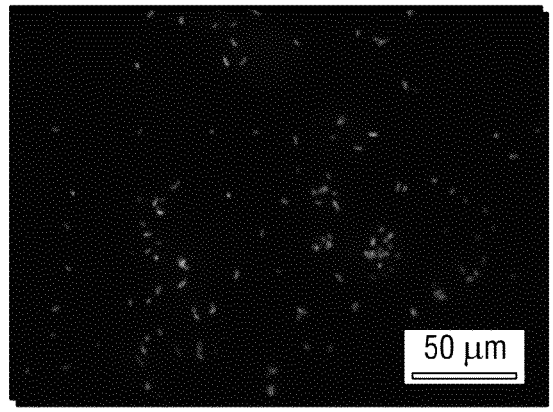
FIG. 6 depicts Representative fluorescence images of E. faecalis after 18 h incubation on (A) PDMS and (B) $MPP_{45}$ surfaces, and (C) results representing the mean of at least 3 experiments where 10 fields were imaged for each sample surface.
Figure 6C:
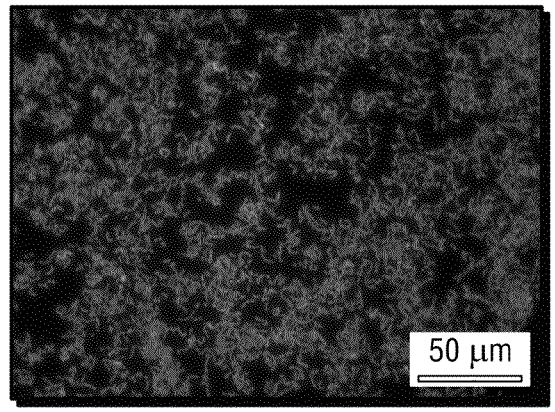
Figure 6C:
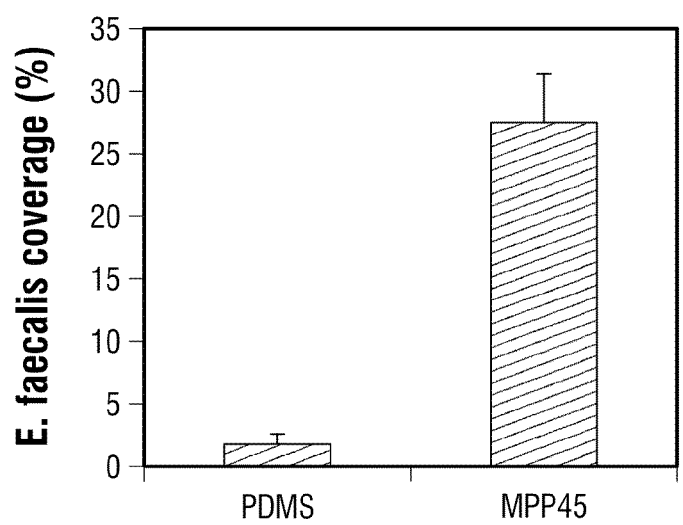
Figure 7A:
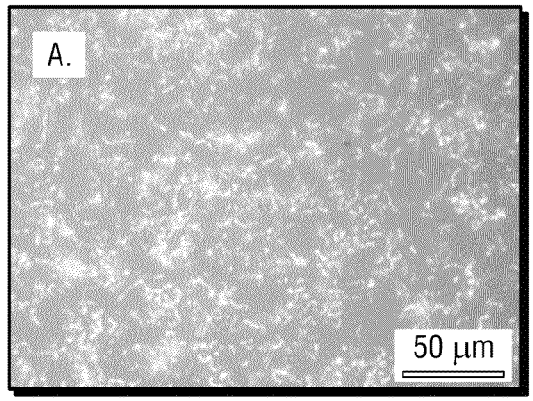
FIG. 7 depicts representative overlay images of FITC and brightfield after 72 h incubation of E. faecalis (B, C, E, F)
Figure 7B:
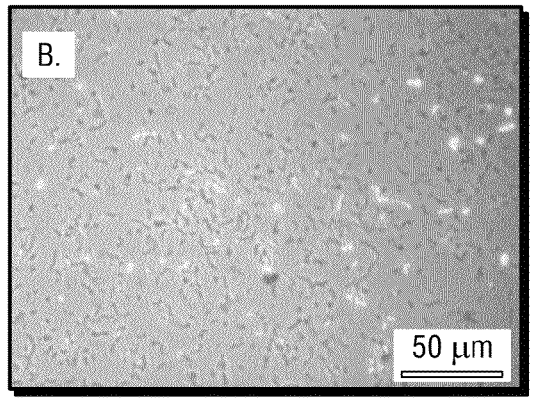
Figure 7C:
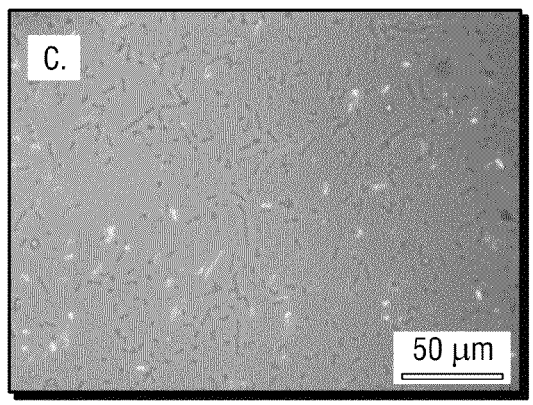
Figure 7D:
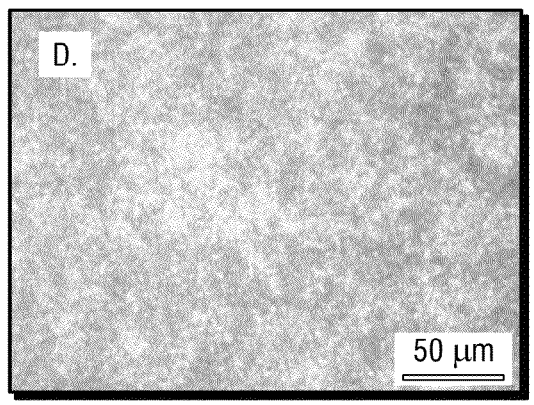
Figure 7G:
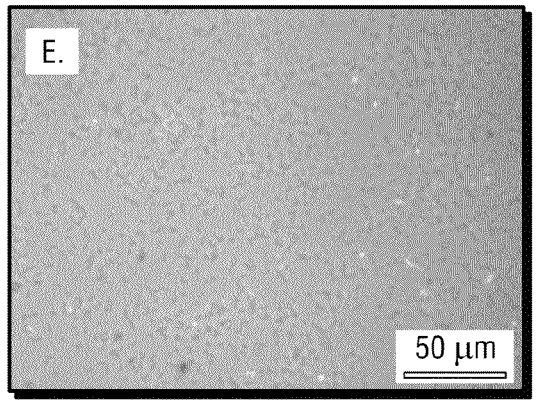
Figure 7G:
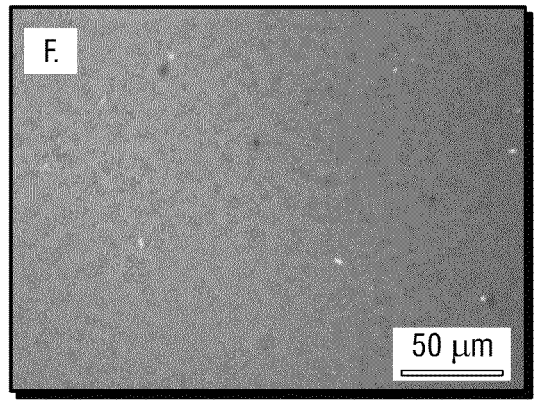
Figure 7G:
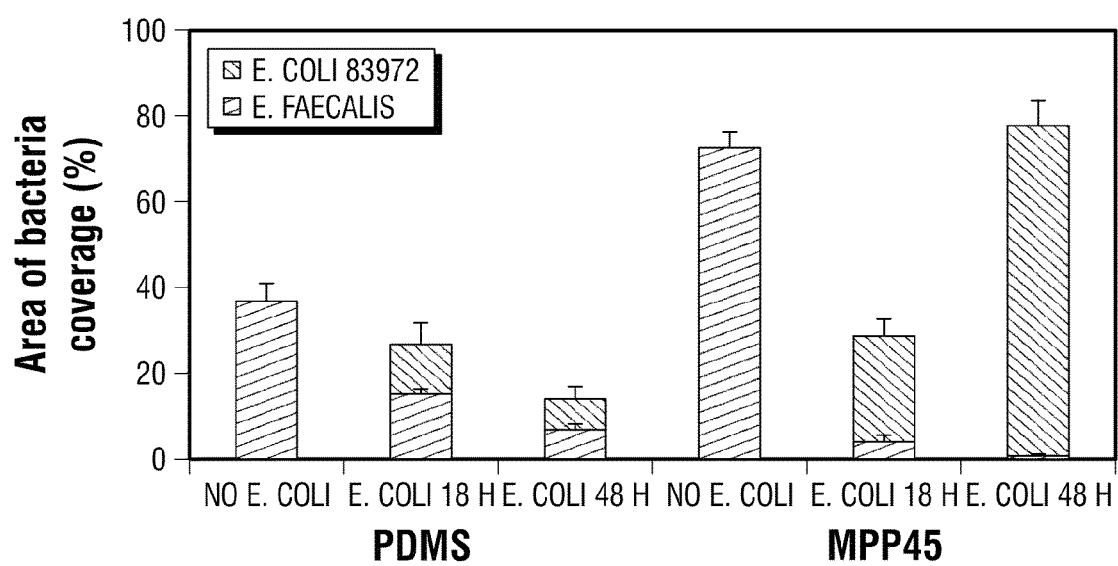

Another preferred embodiment of the present invention shows the representative fluorescence images of *E. faecalis* after 18 h incubation on (A) PDMS and (B) $MPP_{45}$ surfaces. (C) Results represent the mean of at least 3 experiments where 10 fields were imaged for each sample surface (FIG. 6). Bacterial adherence assay was also performed on uropathogenic *E. faecalis*. These bacteria were found to be commonly associated with implantable device-related infections and thus used in our bacterial interference assay as a challenge organism [38]. The results of the fluorescence-based microscopy assay showed greater adherence of *E. faecalis* to $MPP_{45}$ surface compared to PDMS (15.7-fold increase in area, *P<0.001, T-test) (FIG. 6). However, the probable mechanism for the observed preferential attachment of *E. faecalis* to mannose surfaces has yet to be explored.

Another preferred embodiment of the present invention shows the bacterial interference results for PDMS and $MPP_{45}$ surfaces pre-coated with benign *E. coli* 83972 for 1 or 2 weeks. Almost no *E. faecalis* adhered to all *E. coli* 83972 surfaces after 30 min exposure with challenge pathogen and grown for 24 h in fresh LB media. Representative results represent the mean of 2 experiments where 10 fields were imaged for each sample surface. Bacterial interference were initially performed on surfaces that were pre-coated with the benign fim+*E. coli* for a period of one week and two weeks. However, the interference assays were performed at relatively short exposure time with the challenge pathogen (30 min or 24 h incubation). Successful results showed almost no *E. faecalis* attachment on both PDMS and $MPP_{45}$ surfaces (FIG. 10).

Another preferred embodiment of the present invention shows the representative overlay images of FITC and brightfield after 72 h incubation of *E. faecalis* (B, C, E, F) with or (A, D) without pre-formed *E. coli* 83972 on (A-C) PDMS and (D-F) $M_{E45}$ surfaces. The benign bacteria were grown for (B, E) 18 h or (C, F) 48 h on the PDMS and mannose surfaces. (G) Results represent the mean of at least 3 experiments where 10 fields were imaged for each sample surface (FIG. 7). In an attempt to stretch the capabilities of the benign biofilms to prevent the attachment and subsequent colonization of *E. faecalis*, we have subjected the surfaces to a longer 72 h incubation with the challenge pathogen. To ensure that there were no depletion of the nutrients from the media and that enough viable challenge pathogen is present during the length of the assay, the surfaces were transferred to new LB media inoculated with freshly prepared suspension of *E. faecalis* ($10^5$ CFU/mL) every 24 h. Prior to the 72 h challenge with *E. faecalis*, both $MPP_{45}$ and PDMS surfaces were incubated with the benign fim+*E. coli* for 18 or 48 h. This comparison (18 versus 48 h) was made to establish the importance of creating a high coverage, stable biofilms of benign bacteria prior to bacterial interference. Representative images from the microscopy-based assay and quantification of results are shown in FIG. 7. As a control, the *E. faecalis* was also grown for 72 h on both surfaces but without a pre-established biofilm of the benign bacteria. Upon treatment of the unmodified PDMS and the mannose-modified PDMS surface $MPP_{45}$ with *E. coli* 83972 for 18 h, *E. faecalis* adherence was reduced by 2.4-fold (in area of *E. faecalis*, *P<0.001, T-test) and 16.9-fold (in area of *E. faecalis*, *P<0.001, T-test), respectively. Hence, even the coverage was low, the existence of *E. coli* 83972 successfully impeded the growth of *E. faecalis* on both PDMS and mannose surfaces. On the other hand, the bacterial interference was greatly improved when higher coverages of benign fim+*E. coli* (~50% to almost full area coverage for PDMS and $MPP_{45}$, respectively) were pre-formed on the surfaces after 48 h of adherence. Significantly, such coating of *E. coli* 83972 biofilms resulted in a 5.4-fold (in area, *P<0.001, T-test) decrease of *E. faecalis* adherence on PDMS surface while a 104-fold (in area, *P<0.001, T-test) decrease on the mannose-modified surface $MPP_{45}$. The durability of the benign biofilms during bacterial interference for 72 h reflect their remarkable stability on the mannose-modified surfaces. As a general observation, the surface area coverages of the benign bacteria decreased in the presence of the challenge pathogen. The decrease, however, was much more evident for the PDMS surfaces which did not form stable benign *E. coli* biofilms. For instance, the coverage of the adherent benign bacteria on PDMS was greatly decreased from (55.1±3.7) % to (7.2±2.8) % during bacterial interference for 72 h. On the other hand, there is only a slight decrease from (82.5±1.34) % to (77.1±5.9) % coverage of the benign biofilms even after continuously challenging with a high concentration ($10^5$ CFU/mL) of *E. faecalis* for 72 h. These remarkable results were attributed to the greatly enhanced stability of the benign biofilms on the $MPP_{45}$ surfaces compared to PDMS.

Another preferred embodiment of the present invention teaches use of the probiotic *E. coli* strain Nissle 1917 that has been marketed for more than 90 years under the trade name "Mutaflor" as a probiotic remedy against intestinal disorder. The native *E. coli* Nissle 1917 is the most studied and extensively tested *E. coli* strain for use in humans, and it possesses an intact type 1 fimbriae for binding to mannose-presenting surfaces [80]. Another novelty of the present invention is the first use of this probiotic strain to establish a densely packed biofilm on mannose-presenting silicone surfaces for prolonged bacterial interference against the attachment and colonization of uropathogenic *E. faecalis* bacteria.

Another preferred embodiment of the present invention teaches a method to modify the surface of silicone with generation 5 poly(amidoamine) (G5 PAMAM) dendrimers, followed by attachment of a variety of mannosides varying the glycosidic linkage, including oligo(ethylene glycol) ($EG_5$-Man), biphenyl (BiPhen-Man), alkynylphenyl (Phen-Man) and triazolylalkyl (TA-C1-Man, TA-C3-Man, FIG. 14), where TA-C1 indicates triazolylmethyl and TA-C3 indicates triazoylypropyl. These glycosidic linkages have been reported to enhance the binding of mannosides with FimH receptor in solution [81-84]. We evaluated the adherence and biofilm formation of *E. coli* Nissle 1917 on these mannoside-presenting surfaces. To the best of our knowledge, the attachment of *E. coli* Nissle 1917 to surfaces presenting mannose has not been explored prior to this study. We further challenged the Nissle 1917-coated surfaces with uropathogenic *E. faecalis* for 11 days at a high concentration ($10^8$ CFU/mL), that is, three orders of magnitude higher than the diagnostic threshold concentration for urinary tract infection. We finally compared the performance of *E. coli* Nissle 1917 with that of fim+*E. coli* 83972 on these mannoside surfaces.

The biofilm formation of *E. coli* Nissle 1917 on the above mannose surfaces was performed in static conditions to promote type 1 fimbriae expression in the bacteria [85]. As compared to fim+*E. coli* 83972 that formed biofilms on all mannoside surfaces after 2 days incubation, *E. coli* Nissle 1917 took longer time (5 days) to form biofilms on selected mannose surfaces. Although the biofilms of *E. coli* Nissle 1917 grew more slowly than those of fim+*E. coli* 83972 on the mannoside surfaces, they had a comparable density and better stability (see below). As shown by the reflected brightfield image (FIG. 15), *E. coli* Nissle 1917 almost completely covered the BiPhen-Man surface. A close examination of the magnified image reveals a relatively flat morphology consisting of closely packed dots measured ~1 μm in diameter, similar to the diameter of the bacteria. This observation suggests a vertical (standing up) orientation for most bacteria in the biofilms. Similar vertical orientation of the bacteria was observed in the biofilms of fim+*E. coli* 83972 on the BiPhen-Man surfaces.

The above biofilms of *E. coli* Nissle 1917 were then challenged by a common uropathogen *Enterococcus faecalis*. The surfaces were incubated with the challenge bacterial suspension ($10^8$ CFU mL$^{-1}$) in LB media for 11 days (FIG. 16*b*-3*d*), with the samples transferred to a fresh suspension of *E. faecalis* ($10^8$ CFU mL$^{-1}$) every 24 h. To differentiate the two bacteria by microscopy, a GFP-transformed *E. faecalis* strain was used in the experiments together with the non-fluorescent *E. coli* Nissle 1917. The corresponding surfaces without the pre-established benign biofilms were used as the control (FIG. 16*b*). The bacterial interference performance of *E. coli* Nissle 1917 was compared with fim+*E. coli* 83972. The results are presented in FIG. 16*a*, plotting the coverage of *E. faecalis* on all surfaces. Adherence of *E. faecalis* to all the surfaces without pre-formed benign biofilms did not show any significant difference (*P=0.641). On the other hand, the presence of both *E. coli* Nissle 1917 and fim+*E. coli* 83972 biofilms decreased the adherence of the pathogenic bacteria in all surfaces after the long-term (11 days) bacterial interference. The performance of the *E. coli* Nissle 1917 biofilm on the mannoside surfaces follows the order of Biphen-Man>Phen-Man>TA-C3-Man>EG$_5$-Man>TA-C1-Man>>Biphen-F-Man. The order for fim+*E. coli* 83972 is similar. Significantly, FIG. 16*a* shows that the benign biofilms of *E. coli* Nissle 1917 performed better than fim+*E. coli* 83972, with all surfaces having fewer *E. faecalis* adherence (*P=0.016, T-test). For example, the pre-established biofilms of *E. coli* Nissle 1917 (FIG. 16*d*) on the BiPhen-Man surface performed substantially better than *E. coli* 83972 (FIG. 16*c*), resulting in a 19-fold vs 10-fold decrease in *E. faecalis* coverage relative to the control surface without any benign biofilm (FIG. 16*b*) (*P<0.05, T-test). A closer look at the magnified overlay of the reflected brightfield and fluorescence image in FIG. 3*d* revealed that a dense, stable benign biofilm of *E. coli* Nissle was maintained on the BiPhen-Man surface even after 11 days of continuous challenge with the aggressive biofilm-forming pathogen *E. faecalis* ($10^8$ CFU mL$^{-1}$).

Another preferred embodiment of the present invention teaches the preparation of PAMAM-modified PDMS surfaces.

Preparation of the PDMS Substrates:

A 10:1 ratio of PDMS base and curing agent (SYLGARD 184 Silicone Elastomer Kit, Dow Corning, Midland, Mich.) were mixed thoroughly and allowed to stand for at least 30 min or until no bubbles were detected in the mixture. To prepare a thin layer of PDMS, the mixture was gently poured on top of a clean silicon wafer, and then pressed against a film of octadecyltrichlorosilane (OTS) (Sigma Aldrich, St. Louis, Mo.) pre-formed on another silicon wafer. The OTS monolayer was assembled by immersing a clean silicon wafer in a solution of 0.1 M OTS in toluene for 30 min, followed by rinsing with toluene and drying with argon. The purpose of using an OTS film was to aid in the peeling of the top silicon layer to expose a relatively flat PDMS surface. The mixture was cured at 110° C. for 1 h. After 1 h, the OTS-modified silicon wafer was peeled and the PDMS surface was put in a vial and heated to 110° C. under vacuum to remove contamination from low boiling point components.

Oxidation by $CO_2$ Plasma and Attachment of PAMAM Dendrimers:

$CO_2$ plasma oxidation was carried out on the PDMS surface using Harrick plasma cleaner (Model PDC-32G, 100 W) with low power setting (6.8 W). The PDMS surfaces were exposed to $CO_2$ plasma at different exposure times, 15 s, 30 s, 45 s, 60 s, to provide the plasma-treated PDMS substrates, $P_{15}$, $P_{30}$, $P_{45}$ and $P_{60}$ (FIG. 1), respectively. The resulting oxidized PDMS were immediately immersed in a solution of 1 mg/mL Generation 5 poly(amidoamine) (G5 PAMAM) dendrimer (Dendritech, Inc., Midland, Mich.) in phosphate buffered saline (PBS) for 1 h to provide the PAMAM-coated surfaces PP$_{15}$, PP$_{30}$, PP$_{45}$ and PP$_{60}$ (FIG. 1). All the PAMAM-coated surfaces were washed copiously with Millipore water and dried with argon.

Another preferred embodiment of the present invention teaches the characterization of PDMS and PAMAM surfaces.

Preparation of the Standard for PAMAM Density Calculations:

Silicon substrates evaporated with gold films were cut into 1×2 cm$^2$ area, and treated with oxygen plasma for 1 min. The gold surfaces were directly immersed in a solution of bis(11-azidoundecyl)disulfide (Sigma Aldrich, St. Louis, Mo.) in absolute ethanol. After 24 h, the films were washed with absolute ethanol, and dried with a flow of argon. An ellipsometer (Rudolph Research, Auto EL III), operated with a 632.8 nm He—Ne laser at an incident angle of 70°, was used for thickness measurement of the azide-terminated self-assembled monolayer (SAM) on gold assuming a refractive index of 1.45 for the organic layers. At least three measurements were taken for each sample. The ellipsometric thickness of the samples was measured to a constant value (13.0±0.5 Å) prior to XPS measurements.

X-Ray Photoelectron Spectroscopy (XPS):

A PHI 5700 X-ray photoelectron spectrometer was equipped with a monochromatic Al Kα X-ray source (hv=1486.7 eV) incident at 90° relative to the axis of a hemispherical energy analyzer. The spectrometer was operated both at high and low resolutions with pass energies of 23.5 eV and 187.85 eV, respectively, a photoelectron take off angle of 45° from the surface, and an analyzer spot diameter of 1.1 mm. High resolution spectra were obtained for photoelectrons emitted from C1s, O1s, Si2p and N1s for PDMS and PAMAM surfaces, and Au4f and S2p for the azide-terminated SAM standard. All spectra were collected at room temperature with a base pressure of 1×10$^{-8}$. Electron binding energies were calibrated with respect to the C1s line at 284.8 eV (C—C). A PHI Multipak software (version 5.0A) was used for all data processing. The high resolution data were analyzed first by background subtraction using the Shirley routine and a subsequent non-linear fitting to mixed Gaussian-Lorentzian functions. Atomic compositions were derived from the high-resolution scans. Peak areas were obtained after subtraction of the integrated baseline and corrected for sensitivity factors.

Contact-Angle Goniometry:

Advancing contact angles were measured at room temperature and ambient relative humidity using a contact angle goniometer (Ramé -Hart model 100) while the pipet tip is still in contact with the water droplet. Millipore water (pH=7.0) was dispensed and withdrawn using a Matrix Technologies micro-Electrapette 25. At least three measurements were collected for each sample. Initial contact angle measurements were performed immediately after plasma treatment for the oxidized PDMS surfaces (P), while the freshly prepared PAMAM surfaces (PP) were first washed with Millipore water and dried with argon to remove weakly bound PAMAM from the surface before taking the measurements.

Long-Term Stability of PAMAM Surfaces:

In order to determine the stability of the PAMAM coatings on PDMS, both PAMAM and untreated PDMS surfaces were stored in a 24-well plate containing 0.5 mL of PBS buffer and monitored with XPS and contact angle measurements during time periods of 7, 15, 22 and 36 days. Prior to all measurements, the samples were thoroughly washed with Millipore water and dried with argon to remove any physisorbed contaminants.

Another preferred embodiment of the present invention teaches the preparation of mannose-presenting PDMS surfaces.

Synthesis of Carboxy-Terminated Mannose with OEG Linker (Mann-COOH):

Triphenylphosphene (36.0 mg, 0.077 mmol) was added to a solution of azide-terminated mannose (Mann-$N_3$) [47] (18 mg, 0.038 mmol) in 1 mL of tetrahydrofuran. The mixture was stirred overnight. Subsequent removal of the solvent followed by purification by column chromatography using 20% methanol in dichloromethane gave the amino-terminated mannose (Mann-$NH_2$) (14.3 mg, 85%). $^1$H NMR (300 MHz, $D_2O$) δ 4.01-3.41 (m, 30H), 3.17 (s, 1H); $^{13}$C NMR (75 MHz, $D_2O$) δ 99.9, 72.7, 70.5, 69.9, 69.5, 69.4, 69.3, 66.7, 66.4, 60.9, 39.1; MS (ESI) m/z calculated for $C_{18}H_{37}NO_{11}$: 443.5. found: 444.5 ([M+H]$^+$). Maleic anhydride (327 mg, 3.26 mmol) was then added to the resulting Mann-$NH_2$ (725 mg, 1.63 mmol) dissolved in 1 mL of tetrahydrofuran and the mixture was stirred overnight. The solvent was removed and purification by column chromatography using 20% methanol in dichloromethane gave the carboxy-terminated mannose (502.4 mg, 57%). $^1$H NMR (300 MHz, $D_2O$) δ 3.95-3.77 (m, 5H), 3.75-3.61 (m, 26H), 2.5 (m, 4H); $^{13}$C NMR (75 MHz, $D_2O$) δ 179.7, 175.6, 99.9, 72.7, 70.5, 69.9, 69.5, 69.4, 68.8, 66.7, 66.3, 60.9, 38.9, 31.9, 31.7; MS (ESI) m/z calcd for $C_{22}H_{41}NO_{14}$: 543.6. found: 566.4 ([M+Na]$^+$). Preparation of Mann-COOH is illustrated in FIG. 11.

Coupling of Carboxy-Terminated Mannose to PAMAM-Modified PDMS Surfaces.

PAMAM-coated surfaces ($PP_{15}$, $PP_{30}$, $PP_{45}$ and $PP_{60}$, FIG. 1) were placed on separate wells in a 24-well plate. A solution containing 3 mM Mann-COOH, 60 mM of 1-ethyl-3-(3-dimethylaminopropyl)carbodiimide hydrochloride (EDC) and 30 mM N-hydroxysuccinimide (NHS) in Millipore water was prepared. A 0.5 mL of this solution was used to immerse each of the PAMAM surfaces for 2 h. After 2 h, the substrates were washed with Millipore water and dried with argon to provide the mannose-coated surfaces ($MPP_{15}$, $MPP_{30}$, $MPP_{45}$ and $MPP_{60}$, FIG. 1).

Another preferred embodiment of the present invention shows the preparation of bacterial strains. Derivative strains of *Escherichia coli* 83972 expressing type 1 fimbriae (fim+*E. coli* 83972) [47] and the challenge pathogenic bacteria, a human bloodstream isolate of *Enterococcus faecalis*, which was transformed with pMB158GFP to express GFP [57], were provided by Dr. Barbara W. Trautner at Baylor College of Medicine. For all bacterial assays, a single colony from each bacterial plate was grown in 50 mL of Luria Bertani (LB) (BD, Franklin Lakes, N.J.) media containing appropriate antibiotics (20 μg/mL chloramphenicol (Sigma Aldrich, St. Louis, Mo.) and 4 μg/mL tetracycline (Sigma Aldrich, St. Louis, Mo.) for benign fim+*E. coli* 83972 and *E. faecalis*, respectively). After overnight incubation, the optical density at 600 nm ($OD_{600}$) was adjusted to 0.25 for each bacterial culture, corresponding to a bacterial concentration of $10^8$ CFU/mL.

Another preferred embodiment of the present invention teaches how to measure the adherence assay of *E. coli* 83972 and *E. faecalis*. The ability of fim+*E. coli* 83972 and *E. faecalis* to adhere to mannose-coated (MPP) and PDMS surfaces was assessed by the following adherence assay. Each surface was placed in a 15 mL centrifuge tube containing 10 mL of LB media with appropriate antibiotics, and inoculated with of either fim+*E. coli* 83972 or *E. faecalis* to obtain a bacterial concentration of $10^5$ CFU/mL (10 μL of the bacterial suspension with an $OD_{600}$ of 0.25 were added to 10 mL of LB in each tube). The surfaces were incubated with the respective bacteria for 18 or 48 h with shaking at 37° C. After incubation, the surfaces were rinsed three times in PBS prior to mounting on a glass slide for microscope imaging. In addition to the microscopy-based assay, a standard plate-based counting was performed to obtain the viable bacterial counts of fim+*E. coli* 83972 that adhered on the surfaces. Thus, the surfaces following the final rinse with PBS were transferred to a 1 mL solution of 0.01% sodium dodecyl sulfate (SDS), and sonicated for 10 min. Serial dilutions from the sonicated bacterial suspension ($10^{-1}$, $10^{-2}$ and $10^{-3}$) were prepared and 10 microliters of each dilution was plated in duplicates on LB agar with chloramphenicol antibiotic. The plates were incubated at 37° C., and the bacterial colonies formed were counted after 24 h.

Another preferred embodiment of the present invention teaches how to conduct the bacterial interference assay. Bacterial interference assays were performed with some modifications to an established protocol for in vitro bacterial interference [38, 39]. The surfaces were first placed in 10 mL of LB broth containing 20 μg/mL of chloramphenicol antibiotic and $10^5$ CFU/mL bacterial suspension of fim+*E. coli* 83972. The benign bacteria were allowed to adhere to the surfaces for a period of 18 or 48 h with shaking at 37° C. The surfaces with pre-formed fim+*E. coli* biofilms were transferred to 10 mL sterile LB (no antibiotics) in separate 15-mL tubes containing $10^5$ CFU/mL bacterial suspension of the challenge *E. faecalis* pathogen. The tubes were continuously shaken at 37° C. for 24 h. After the first 24 h, the surfaces were transferred to new 15 mL centrifuge tubes containing 10 mL of freshly prepared challenge pathogen suspension ($10^5$ CFU/mL), and then re-incubated with shaking at 37° C. This procedure was done three times such that the total time for bacterial interference is 72 h. At the end of the bacterial interference, the surfaces were rinsed three times in PBS, and then imaged using a fluorescence microscope.

Another preferred embodiment of the present invention teaches how to obtain microscopy imaging of the surfaces. The images from the bacterial adherence and interference assays were obtained using the 40× objective and the reflected brightfield and FITC filters of a Nikon 80i Microscope (Nikon Instruments, Melville, N.Y.). NIS Elements software (Version 3.0, Nikon Instruments, Melville, N.Y.) and a CoolSnap HQ2 camera (Photometrics, Tuscon, Ariz.) were used for image acquisition and analysis. Differentiation of the two strains used in the bacterial interference experiment was possible since the *E. faecalis* expresses GFP ($\lambda_{em}$=535 nm) while the fim+*E. coli* 83972 is non-fluorescent. Live/dead imaging was performed by adding 1.5 μL of 15 μM propidium iodide, a dye which show red fluorescence for membrane-compromised cell death, on the surfaces having the pre-formed fim+ *E. coli* 83972 prior to viewing under the microscope.

*E. coli* Nissle 1917 was prepared by dissolving one capsule of the commercially available "Mutaflor" (Mutaflor, Medical Futures Inc., Ontario, Canada) in Luria Bertani (LB, 50 mL) (BD, Franklin Lakes, N.J.) broth overnight at 37° C. without shaking. The resulting bacterial suspension was diluted (1:100, bacterial suspension:fresh LB) and re-incubated overnight under static conditions at 37° C. The resulting bacterial suspension was diluted ($10^{-1}$, $10^{-2}$ and $10^{-3}$) and plated on LB agar. The plates were incubated overnight at 37.degree. C. Fresh LB broth (50 mL) was then inoculated with a single colony of *E. coli* Nissle 1917 from the plates that were grown overnight. The optical density of the resulting bacterial suspension was adjusted ([$OD_{600}$]=0.25, $10^8$ CFU $mL^{-1}$). The wild-type *E. coli* 83972 was obtained from BEI Resources (http://www.beiresources.org). Genetically modified *E. coli* 83972 expressing type 1 fimbriae (strain HU2545) and *E. faecalis* were prepared similar to our previous report [13]. Briefly, a single colony from each bacterial plate containing fim+*E. coli* 83972 and *E. faecalis* was incubated in LB broth (50 mL) containing appropriate antibiotics (20 g/mL chloramphenicol (Sigma Aldrich, St. Louis, Mo.) and 4 g/mL tetracycline (Sigma Aldrich, St. Louis, Mo.) for benign fim+ *E. coli* 83972 and *E. faecalis*, respectively). After overnight static incubation at 37° C. the optical density was adjusted for each bacterial culture ([$OD_{600}$]=0.25, $10^8$ CFU $mL^{-1}$).

Adherence of *E. coli* Nissle 1917

A modified bacterial adherence assay was performed to evaluate the ability of *E. coli* Nissle 1917 to attach to various mannose-presenting and control surfaces. Each surface was placed on a separate well of a 24-well plate and inoculated with *E. coli* Nissle 1917 bacterial suspension (1 mL, $10^8$ CFU $mL^{-1}$). The surfaces were incubated with the probiotic bacteria for 5-6 days without shaking at 37° C. After incubation, the surfaces were rinsed by immersing the surfaces three times in PBS solution to remove loosely attached bacteria prior to microscope imaging.

Bacterial Interference Assay Against *E. faecalis*.

The surfaces with pre-established biofilms of *E. coli* Nissle 1917 were placed in separate wells of a 24-well plate LB media (50 mL) inoculated with a bacterial suspension of *E. faecalis* ($10^8$ CFU $mL^{-1}$). The surfaces were incubated for 11 days at 37° C. under static conditions, with replacement of fresh bacterial suspension of *E. faecalis* ($10^8$ CFU $mL^{-1}$) every 24 h. For comparison, a set of experiment was performed on surfaces pre-coated with fim+*E. coli* 83972 (by incubation with fim+*E. coli* 83972 ($10^8$ CFU $mL^{-1}$) for 2 days) [31]. At the end of the bacterial interference (11 days), the surfaces were immersed in PBS solution three times prior to viewing under the microscope.

Synthesis of Carboxy-Terminated Mannose with OEG Linker. Alternative Mannosides.

Procedures for Synthesis of Compound 2a (FIGS. 18A, 18B, 18C).

Compound 7 was prepared in two steps according to methods known in the art [86].

Synthesis of Compound 8:

Under nitrogen atmosphere, to a solution of compound 7 (2.8 g, 9.11 mmol) in anhydrous THF (15 mL) was added 60% sodium hydride suspended in mineral (10.6 mg, 0.05 equiv) at room temperature. After stirring for 10 minutes, tert-butyl acrylate (6.6 mL, 5 equiv) was added, and the mixture was allowed to stir for 12 h at room temperature. Followed the evaporation of the volatile components under reduced pressure, water (10 mL) and dichloromethane (15 mL) was added. The organic layer was separated, and the aqueous layer was extracted by dichloromethane (15 mL×3). The combined organic layers were washed by brine (10 mL) and dried over anhydrous $MgSO_4$. After filtration and concentration, the residue was purified by silica gel column chromatography to afford the desired product 8 (2.57 g, 65% yield). $^1$H NMR (400 MHz, $CDCl_3$): δ 3.70-3.6 (m, 24H), 3.38 (t, J=5.5 Hz, 2H), 2.49 (t, J=6.4 Hz, 2H), 1.44 (s, 9H). $^{13}$C NMR (100 MHz, $CDCl_3$): δ 170.95, 80.52, 70.72, 70.70, 70.6, 70.61, 70.52, 70.40, 70.08, 66.92, 50.69, 36.28, 28.13. MS (ESI): [M+$Na^+$] calcd for $C_{19}H_{37}N_3NaO_8$=458.2. Found 458.2.

Synthesis of Compound 9:

To a 50 mL round bottom flask was charged with compound 8 (1.06 g, 2.43 mmol), Pd/C (259 mg, 10 mol %), and ethyl acetate (20 mL). The mixture was stirred and mildly bubbled by hydrogen for 4 hours at room temperature. Filtration and evaporation afforded the desired product 9 that was directly used for the next step without purification. $^1$H NMR (500 MHz, $CDCl_3$): δ 3.55 (t, J=6.3 Hz, 2H), 3.50-3.40 (m, 20H), 3.36 (t, J=5.2 Hz, 2H), 2.71 (t, J=5.2 Hz, 2H), 2.35 (t, J=6.3 Hz, 2H), 1.29 (s, 9H). $^{13}$C NMR (125 MHz, $CDCl_3$): δ 170.83, 80.39, 73.43, 70.53, 70.44, 70.32, 70.23, 66.83, 41.77, 36.19, 28.06. MS (ESI): [M+$H^+$] calcd for $C_{19}H_{40}NO_8$=410.3. Found 410.3.

Compound 11 was prepared according to the methods known in the art [87].

Synthesis of Compound 12:

To a solution of compound 11 (6.4 g, 20 mmol), methanol (40 mL), and dichloromethane (20 mL) was added sodium hydroxide (840 mg, 21 mmol). The mixture was allowed to stir at room temperature for 20 h. The solvents were removed under reduced pressure. Lots of white precipitate formed when water (9 mL), dichloromethane (10 mL), and ethyl acetate (10 mL) were added while stirring, which was collected by filtration, well washed with a mixture of dichloromethane (10 mL) and ethyl acetate (10 mL), and then with water (10 mL). After transferring the solid (mono sodium salt) to a separatory funnel, ethyl acetate (80 mL) and conc. HCl (3 mL) diluted with water (20 mL) were successively added. The mixture was vigorously shaken until the solid was disappeared. Then the organic layer was separated and the aqueous layer was extracted by ethyl acetate (25 mL). The organic layers were combined and washed by brine (20 mL), dried over $MgSO_4$, filtered, and concentrated. The solid obtained was washed with n-hexane/ethyl acetate (4/1, 10 mL), providing the desired product 12 as a white powder (4.28 g, 70% yield). $^1$H NMR (400 MHz, $CD_3COCD_3$): δ 8.54 (m, 1H), 8.51 (m, 1H), 8.47 (m, 1H), 3.91 (s, 3H). $^{13}$C NMR (100 MHz, $CD_3COCD_3$): δ 164.58, 164.33, 142.32, 141.91, 133.07, 132.52, 129.55, 93.32, 52.21.

Synthesis of Compound 13:

To a solution of compound 12 (306 mg, 1 mmol), HBTU (455 mg, 1.2 equiv), and dichloromethane (15 mL) was added diisopropylethylamine (524 uL, 3.0 equiv). After stirring for 30 min, amine 9 (451 mg, 1.1 equiv) was added and the resulting mixture was allowed to stir for 15 h. The reaction course could be followed by TLC (4% MeOH in ethyl acetate). When the reaction completed, the reaction mixture was washed by sat. $NH_4Cl$ (10 mL), dried over $MgSO_4$, filtered, concentrated, purified by silica gel column chromatography (eluent: ethyl acetate) to afford the desired product 13 as a yellow viscous oil (540 mg, 78% yield). $^1$H NMR (400 MHz, $CDCl_3$): δ 8.38 (m, 1H), 8.35 (m, 1H), 8.33 (m, 1H), 7.34 (t, J=5.5 Hz, 1H), 3.86 (s, 3H), 3.7-3.5 (m, 26H), 2.43 (t, J=6.4 Hz, 2H), 1.37 (s, 9H). $^{13}$C NMR (100 MHz, $CDCl_3$): δ 171.17, 165.39, 165.01, 140.93, 140.68, 136.58, 132.06, 127.46, 93.83, 80.77, 70.28, 70.19, 70.14, 70.10, 70.00, 69.83, 66.73, 52.68, 40.01, 36.05, 28.13. MS (ESI): [M+$Na^+$] calcd for $C_{28}H_{44}INNaO_{11}$=720.2. Found 720.1.

Compound 15 was prepared according to methods known in the art [88].

Synthesis of Compound 16:

Under $N_2$ atmosphere, a mixture of compound 15 (2.75 g, 5 mmol), bis(pinacolato)diboron (1.524 g, 1.2 equiv), AcOK (1.472 g, 3 equiv), $PdCl_2$(dppf) (122.5 mg, 0.03 equiv), and DMSO (12 mL) was stirred at 80° C. for 10 h. After cooling, water (50 mL) was added, and the resulting mixture was extracted with dichloromethane (30 mL×3). The combined organic layers were washed with brine (20 mL×2), dried over $MgSO_4$, filtered, and concentrated. The residue obtained was subjected to the silica gel column chromatography for purification to afford the desired product 16 as a white foam powder (2.34 g, 85% yield). $^1$H NMR (400 MHz, $CDCl_3$): δ 7.75 (d, J=8.7 Hz, 2H), 7.06 (d, J=8.7 Hz, 2H), 5.56-5.53 (m, 2H), 5.43 (m, 1H), 5.35 (t, J=10.1 Hz, 1H), 4.27 (dd, J=5.0, 12.4 Hz, 1H), 4.11-3.99 (m, 2H), 2.18 (s, 3H), 2.03 (s, 3H), 2.02 (s, 3H), 2.02 (s, 3H), 1.31 (s, 12H). $^{13}$C NMR (100 MHz, $CDCl_3$): δ 170.66, 170.06, 170.02, 169.84, 158.03, 136.66, 115.72, 95.46, 83.85, 69.41, 69.25, 68.92, 65.93, 62.10, 24.92, 20.97, 20.79. MS (ESI): [M+Na$^+$] calcd for $C_{26}H_{35}BNaO_{12}$=573.2. Found 573.3.

Synthesis of Compound 17:

Under $N_2$ atmosphere, a mixture of 13 (261 mg, 0.374 mmol), 16 (281 mg, 1.365 equiv), CsF (171 mg, 3 equiv), Pd(PPh$_3$)$_4$ (30.3 mg, 0.07 equiv), and THF (4 mL) was stirred at 80° C. for 12 h. The mixture was allowed to cool down to room temperature and the solvent was removed under reduced pressure. Dichloromethane (10 mL) was added, which was followed by filtration. The filter cake was thoroughly washed with dichloromethane. Concentrating the filtrate gave the crude product which was purified by silica gel column chromatography (gradient elution: from ethyl acetate to 2% MeOH in ethyl acetate). The desired product 17 was obtained as light yellow syrup (300 mg, 81% yield). $^1$H NMR (400 MHz, $CDCl_3$): δ 8.30 (m, 1H), 8.26 (m, 1H), 8.22 (m, 1H), 7.55 (d, J=8.7 Hz, 2H), 7.13 (d, J=8.7 Hz, 2H), 5.53 (d, J=2.3 Hz, 1H), 5.51 (d, J=3.7 Hz, 1H), 5.42 (m, 1H), 5.33 (t, J=10.1 Hz, 1H), 4.24 (dd, J=5.0, 11.9 Hz, 1H), 4.08-4.00 (m, 2H), 3.89 (s, 3H), 3.64-3.50 (m, 26H), 2.41 (t, J=6.4 Hz, 2H), 2.15 (s, 3H), 2.00 (s, 3H), 1.99 (s, 3H), 1.98 (s, 3H), 1.36 (s, 9H). $^{13}$C NMR (100 MHz, $CDCl_3$): δ 170.93, 170.56, 170.02, 170.00, 169.77, 166.56, 166.38, 155.71, 141.08, 135.68, 134.09, 130.96, 130.35, 128.50, 126.28, 116.98, 95.81, 80.52, 70.54, 70.48, 70.34, 70.31, 69.80, 69.35, 69.31, 68.88, 66.89, 65.89, 62.11, 52.47, 40.11, 36.26, 28.12, 20.95, 20.76. MS (ESI): [M+Na$^+$] calcd for $C_{48}H_{67}NNaO_{21}$=1016.4. Found 1016.3.

Synthesis of Compound 18:

To a solution of compound 17 (410 mg, 0.42 mmol) in dichloromethane (1 mL) was added trifluoroacetic acid (1 mL). The mixture was stirred for 15 h. The reaction was completed as detected by TLC (4% MeOH in ethyl acetate). After removing the volatile components under reduced pressure, the residue was purified by silica gel column chromatography (eluent: 0 to 50% MeOH in ethyl acetate), giving the product 18 as white foam powder (387 mg, 99% yield). $^1$H NMR (400 MHz, $CDCl_3$): δ 8.34 (m, 1H), 8.27 (m, 1H), 8.25 (m, 1H), 7.57 (d, J=8.7 Hz, 2H), 7.13 (d, J=8.7 Hz, 2H), 5.54-5.50 (m, 2H), 5.42 (m, 1H), 5.33 (t, J=10.1 Hz, 1H), 4.24 (dd, J=5.0, 11.9 Hz, 1H), 4.06-4.00 (m, 2H), 3.89 (s, 3H), 3.70-3.50 (m, 26H), 2.51 (t, J=6.4 Hz, 2H), 2.16 (s, 3H), 2.01 (s, 3H), 1.99 (s, 3H), 1.98 (s, 3H). $^{13}$C NMR (100 MHz, $CDCl_3$): δ 174.69, 170.64, 170.09, 170.05, 169.81, 166.90, 166.47, 155.70, 141.04, 135.52, 134.05, 130.96, 130.34, 128.51, 126.51, 116.99, 95.79, 70.22, 70.18, 70.11, 70.04, 69.91, 69.36, 69.30, 68.90, 66.56, 65.90, 62.13, 52.50, 40.04, 34.90, 20.95, 20.76. MS (ESI): [M+Na$^+$] calcd for $C_{44}H_{59}NNaO_{21}$=960.3. Found 960.6.

Synthesis of Compound 2a

Under $N_2$, sodium methoxide (68 mg, 3 equiv) was added to the solution of compound 18 (396 mg, 0.42 mmol) in anhydrous methanol (4 mL). After stirring for 12 h, the reaction was quenched and neutralized by acidic ion-exchange resin DOWEX-50W, filtered, washed with methanol, and concentrated to give the crude product. Further purification was performed by silica gel column chromatography (gradient elution from 5% to 50% MeOH in ethyl acetate) to give the pure product 2a as white foam powder (160 mg, 50% yield). $^1$H NMR (400 MHz, $CD_3OD$): δ 8.35 (m, 1H), 8.25 (m, 1H), 8.22 (m, 1H), 7.58 (d, J=8.7 Hz, 2H), 7.20 (d, J=9.2 Hz, 2H), 5.54 (d, J=1.4 Hz, 1H), 4.92 (s, 5H), 4.04 (m, 1H), 3.95-3.92 (m, 4H), 3.80-3.50 (m, 30H), 2.49 (t, J=6.4 Hz, 2H). $^{13}$C NMR (100 MHz, $CD_3OD$): δ 175.08, 167.65, 166.34, 156.84, 141.27, 135.33, 132.93, 130.97, 129.77, 129.55, 128.03, 126.39, 117.01, 98.75, 74.20, 71.09, 70.60, 70.09 70.04, 69.96, 69.90, 69.82, 69.32, 66.98, 66.80, 61.34, 51.75, 39.77, 35.12. MS (ESI): [M+Na$^+$] calcd for $C_{36}H_{51}NNaO_{17}$=792.3. Found 792.4.

Procedures for the Synthesis of Compound 2b (FIG. 19).

Compound 21 was synthesized according to the literatures, which was obtained as a mixture of anomers (α/β=1.2:1), according to methods known in the art [89].

Compound 23 was synthesized via two steps with compound 22 as the intermediate according to the method used for the analogous transformations of methyl 1,3,4-tri-O-acetyl-α/β-D-fructofuranoside to methyl 1,3,4-tri-O-acetyl-6-deoxy-6-fluoro-α/β-D-fructofuranoside, according to methods known in the art [90].

Synthesis of Compound 22:

At −10° C., to a mixture of compound 21 (α/β=1.2:1) (7.6 g, 21.8 mmol), pyridine (2.5 mL, 1.5 equiv), and dichloromethane (200 mL) was added triflic anhydride (4.0 mL, 1.1 equiv). After stirring for 45 min, water (100 mL) was added. The organic layer was separated and the aqueous layer was extracted with dichloromethane (30 mL×3). The organic layers were combined, washed successively with 10% $H_2SO_4$ (80 mL), sat. $NaHCO_3$ (100 mL), and brine (100 mL), dried over $MgSO_4$, filtered, concentrated to give the crude product. Further purification by silica gel column chromatography (eluent: n-hexane/ethyl acetate: 2:1) provided the product 22 as light yellow viscous oil (9.5 g, 92% yield), which was a mixture of anomers (α/β=1.4:1). $^1$H NMR (500 MHz, $CDCl_3$): for the α-anomer: δ 6.07 (d, J=1.7 Hz, 1H), 5.33 (m, 1H), 5.28 (m, 1H), 5.21 (m, 1H), 4.51 (m, 2H), 4.10 (m, 1H), 2.14 (s, 6H), 2.05 (s, 3H), 1.98 (s, 3H). For the β-anomer: δ 5.87 (d, 1.2 Hz, 1H), 5.45 (dd, J=1.2, 2.9 Hz, 1H), 5.21 (m, 1H), 5.14 (dd, J=3.4, 9.8 Hz, 1H), 4.53 (m, 2H), 3.91 (m, 1H), 2.17 (s, 3H), 2.07 (s, 3H), 2.05 (s, 3H), 1.97 (s, 3H). $^{13}$C NMR (125 MHz, $CDCl_3$): δ 170.21, 169.99, 169.78, 169.70, 169.65, 168.33, 167.91, 118.54 (q, $^1J_{C,F}$=319.4 Hz), 90.25, 90.09, 73.43, 73.28, 72.48, 70.33, 70.24, 68.38, 68.10, 67.92, 65.33, 65.26, 20.81, 20.72, 20.64, 20.59, 20.55. $^{19}$F NMR (470 MHz, $CDCl_3$): β-anomer: −74.30 (s); α-anomer: −74.41 (s).

Synthesis of Compound 23:

To a solution of compound 22 (9.5 g, 20 mmol) in tert-amyl alcohol (60 mL) was added CsF (9.12 g, 3.0 equiv) in one portion. The mixture was refluxed while stirring for 40 min, and then allowed to cool down to room temperature. After evaporating the tert-amyl alcohol under reduced pressure, ethyl acetate (30 mL) was added. The dark brown undissolved solid was removed by filtration. The filtrate was concentrated and the residue was purified by silica gel column chromatography (eluent: n-hexane/ethyl acetate: 3:1 to 2:1), providing the pure product 23 as light yellow solid (4.0 g, 57% yield), which was a mixture of anomers (α/β=4.7:1). $^1$H NMR (500 MHz, CDCl$_3$): for the α-anomer: δ 6.08 (d, J=1.7 Hz, 1H), 5.35 (m, 2H), 5.25 (s, 1H), 4.48 (m, 2H), 4.00 (m, 1H), 2.14 (s, 6H), 2.05 (s, 3H), 2.00 (s, 3H); For the β-anomer: δ 5.87 (s, 1H), 5.47 (d, J=2.3 Hz, 1H), 5.34 (m, 1H), 5.14 (dd, J=3.5, 10.3 Hz, 1H), 4.60 (m, 2H), 3.90 (m, 1H), 2.20 (s, 3H), 2.09 (s, 3H), 2.06 (s, 3H), 2.00 (s, 3H). $^{13}$C NMR (125 MHz, CDCl$_3$): for the α-anomer: δ 170.13, 169.89, 169.58, 169.17, 90.57, 81.00 (d, $^1J_{C,F}$=176.1 Hz), 71.4 (d, $^2J_{C,F}$=19.2 Hz), 68.73, 68.30, 65.16 (d, $^3J_{C,F}$=6.4 Hz), 20.93, 20.84, 20.74; For the β-anomer: 170.32, 169.93, 169.61, 168.49, 90.31, 80.99 (d, $^1J_{C,F}$=175.2 Hz), 73.80 (d, $^2J_{C,F}$=19.2 Hz), 70.71, 68.18, 65.03 (d, $^3J_{C,F}$=6.4 Hz), 20.76, 20.63. $^{19}$F NMR (470 MHz, CDCl$_3$): β-anomer: −231.94 (dt, $^2J_{H,F}$=47.7 Hz, $^3J_{H,F}$=21.6 Hz); α-anomer: −232.39 (dt, $^2J_{H,F}$=46.8 Hz, $^3J_{H,F}$=22.5 Hz).

Synthesis of Compound 24:

(The method used to synthesize compound 15 was applied.) At 0° C., triflic acid (60 uL, 0.15 equiv) was added to a solution of compound 23 (1.3 g, 3.7 mmol), 4-iodophenol (1.633 g, 2 equiv) in dry dichloromethane (60 mL). The mixture was stirred for 12 h at 0° C. Trifilic acid was neutralized by addition of Et$_3$N (65 uL). After removing the solvent under reduced pressure, the residue was purified by silica gel column chromatography (eluent: n-hexane/ethyl acetate: 10:1 to 5:1) to provide the pure product 24 as light yellow solid (1.25 g, 66% yield). $^1$H NMR (500 MHz, CDCl$_3$): δ 7.55 (d, 9.2 Hz, 2H), 6.83 (d, J=9.2 Hz, 2H), 5.54 (dd, J=3.4, 10.3 Hz, 1H), 5.47 (d, J=1.2 Hz, 1H), 5.38-5.34 (m, 2H), 4.49 (m, 1H), 4.39 (m, 1H), 4.02, (m, 1H), 2.15 (s, 3H), 2.03 (s, 3H), 2.00 (s, 3H). $^{13}$C NMR (125 MHz, CDCl$_3$): δ 170.05, 169.66, 155.53, 138.65, 118.73, 95.78, 85.96, 81.16 (d, $^1J_{C,F}$=175.2 Hz), 70.03 (d, $^2J_{C,F}$=19.2 Hz), 69.18, 68.76, 65.30 (d, $^3J_{C,F}$=7.3 Hz), 20.93, 20.79, 20.76. $^{19}$F NMR (470 MHz, CDCl$_3$): −232.56 (dt, $^2J_{H,F}$=47.7 Hz, $^3J_{H,F}$=23.4 Hz).

Synthesis of Compound 25:

Under N$_2$ atmosphere, a mixture of compound 24 (1.2 g, 2 mmol), bis(pinacolato)diboron (610 mg, 1.2 equiv), AcOK (589 mg, 3 equiv), PdCl$_2$(dppf) (49 mg, 0.03 equiv), and DMSO (12 mL) was stirred at 80° C. for 12 h. After cooling, water (20 mL) was added, and the resulting mixture was extracted with dichloromethane (10 mL×3). The combined organic layers were washed with brine (10 mL×2), dried over MgSO$_4$, filtered, and concentrated. The residue obtained was subjected to the silica gel column chromatography for purification to afford the desired product 25 as a white foam powder (820 mg, 80% yield). $^1$H NMR (500 MHz, CDCl$_3$): δ 7.73 (d, 8.1 Hz, 2H), 7.05 (d, J=8.6 Hz, 2H), 5.57 (d, J=1.2 Hz, 1H), 5.54 (dd, J=3.4, 10.3 Hz, 1H), 5.40-5.34 (m, 2H), 4.43 (d, J=2.9 Hz, 1H), 4.34 (d, J=2.9 Hz, 1H), 3.95, (m, 1H), 2.15 (s, 3H), 2.02 (s, 3H), 2.00 (s, 3H), 1.28 (s, 12H). $^{13}$C NMR (125 MHz, CDCl$_3$): δ 170.05, 170.02, 169.64, 157.98, 136.70, 115.56, 95.33, 83.80, 81.09 (d, $^1J_{C,F}$=176.1 Hz), 69.90 (d, $^2J_{C,F}$=18.3 Hz), 69.27, 68.88, 65.34 (d, $^3J_{C,F}$=6.4 Hz), 24.94, 24.90, 20.88, 20.76, 20.74. $^{19}$F NMR (470 MHz, CDCl$_3$): −233.10 (dt, $^2J_{H,F}$=47.7 Hz, $^3J_{H,F}$=25.2 Hz).

Synthesis of Compound 26:

Under N$_2$ atmosphere, a mixture of 13 (540 mg, 0.774 mmol), 25 (592 mg, 1.5 equiv), CsF (365 mg, 3 equiv), Pd(PPh$_3$)$_4$ (65 mg, 0.07 equiv), and THF (15 mL) was stirred at 80° C. for 12 h. The mixture was allowed to cool down to room temperature and the solvent was removed under reduced pressure. Dichloromethane (10 mL) was added, which was followed by filtration. The filter cake was thoroughly washed with dichloromethane. Concentrating the filtrate gave the crude product which was purified by silica gel column chromatography (gradient elution: from ethyl acetate to 2% MeOH in ethyl acetate). The desired product 26 was obtained as light yellow syrup (620 mg, 84% yield). $^1$H NMR (500 MHz, CDCl$_3$): δ 8.34 (m, 1H), 8.29 (m, 1H), 8.24 (m, 1H), 7.58 (m, 2H), 7.27 (t, J=5.2 Hz, 1H), 7.15 (m, 2H), 5.57 (m, 2H), 5.40 (m, 2H), 4.49 (d, J=2.9 Hz, 1H), 4.40 (d, J=3.5 Hz, 1H), 4.06 (m, 1H), 3.92 (s, 3H), 3.70-3.50 (m, 26H), 2.44 (t, J=6.3 Hz, 2H), 2.17 (s, 3H), 2.04 (s, 3H), 2.02 (s, 3H), 1.39 (s, 9H). $^{13}$C NMR (125 MHz, CDCl$_3$): δ 171.00, 170.13, 170.09, 169.71, 166.65, 166.42, 155.75, 141.14, 135.66, 134.11, 130.99, 130.42, 130.30, 128.61, 126.39, 116.88, 95.78, 81.21 (d, $^1J_{C,F}$=175.2 Hz), 80.60, 70.55, 70.47, 70.41, 70.27, 70.07, 69.91, 69.30, 68.87, 66.88, 65.38 (d, $^3J_{C,F}$=6.4 Hz), 52.49, 40.10, 36.23, 28.14, 20.96, 20.81, 20.78. $^{19}$F NMR (470 MHz, CDCl$_3$): −232.70 (dt, $^2J_{H,F}$=47.7 Hz, $^3J_{H,F}$=24.3 Hz). MS (ESI): [M+Na$^+$] calcd for C$_{46}$H$_{64}$FNNaO$_{19}$=976.4. Found 976.3.

Synthesis of Compound 27:

To a solution of compound 26 (620 mg, 0.65 mmol) in dichloromethane (2 mL) was added trifluoroacetic acid (2 mL). The mixture was stirred for 20 h. The reaction was completed as detected by TLC (4% MeOH in ethyl acetate). After removing the volatile components under reduced pressure, the residue was purified by silica gel column chromatography (eluent: 0 to 50% MeOH in ethyl acetate), giving the product 27 as white foam powder (540 mg, 92% yield). $^1$H NMR (500 MHz, CDCl$_3$): δ 8.27 (s, 1H), 8.16 (m, 2H), 8.24 (m, 1H), 7.86 (br s, 1H), 7.48 (d, J=8.6 Hz, 2H), 7.04 (d, J=8.6 Hz, 2H), 5.48 (d, J=1.8 Hz, 1H), 5.45 (dd, J=3.4, 10.3 Hz, 1H), 5.34 (m, 1H), 5.30 (t, J=10.3 Hz, 1H), 4.39 (d, J=2.9 Hz, 1H), 4.29 (d, J=2.9 Hz, 1H), 3.94 (m, 1H), 3.79 (s, 3H), 3.60-3.40 (m, 26H), 2.44 (t, J=6.3 Hz, 2H), 2.07 (s, 3H), 1.95 (s, 3H), 1.91 (s, 3H). $^{13}$C NMR (125 MHz, CDCl$_3$): δ 174.39, 170.06, 170.02, 169.67, 166.98, 166.34, 155.63, 140.82, 135.39, 133.90, 130.85, 130.17, 130.11, 128.46, 126.69, 116.84, 95.67, 81.12 (d, $^1J_{C,F}$=175.2 Hz), 70.05, 69.94, 69.90, 69.81, 69.17, 68.84, 66.42, 65.19 (d, $^3J_{C,F}$=6.4 Hz), 52.38, 39.92, 34.69, 20.80, 20.66, 20.64. $^{19}$F NMR (470 MHz, CDCl$_3$): −232.70 (dt, $^2J_{H,F}$=47.7 Hz, $^3J_{H,F}$=24.3 Hz). MS (ESI): [M+Na$^+$] calcd for C$_{42}$H$_{56}$FNNaO$_{19}$=920.3. Found 920.5.

Synthesis of Compound 2b:

Under N$_2$, sodium methoxide (97 mg, 3 equiv) was added to the solution of compound 27 (540 mg, 0.6 mmol) in anhydrous methanol (5 mL). After stirring for 19 h, the reaction was quenched and neutralized by acidic ion-exchange resin DOWEX-50W, filtered, washed with methanol, and concentrated to give the crude product. Further purification was performed by silica gel column chromatography (gradient elution from 0% to 20% MeOH in ethyl acetate) to give the pure product 2b as white foam powder (264 mg, 57% yield). $^1$H NMR (500 MHz, CD$_3$OD): δ 8.39 (s, 1H), 8.31 (s, 1H), 8.26 (s, 1H), 7.64 (d, J=8.6 Hz, 2H), 7.20 (d, J=8.6 Hz, 2H), 5.55 (s, 1H), 4.90 (br, 5H), 4.70-4.48 (m, 2H), 4.04 (t, J=1.8 Hz, 1H), 3.92 (m, 4H), 3.78 (m, 2H), 3.74-3.54 (m, 26H), 2.51 (t, J=6.3 Hz, 2H). $^{13}$C NMR (125 MHz, CD$_3$OD): δ 174.39, 167.75, 166.35, 156.72, 141.33, 135.38, 133.14, 131.05, 129.82, 129.58, 128.07, 126.43, 116.92, 98.73, 82.09 (d, $^1J_{C,F}$=172.5 Hz), 72.90 (d, $^2J_{C,F}$=18.3 Hz), 71.04, 70.43, 70.02, 69.94, 69.86, 69.79, 69.42, 66.42, 65.88 (d, $^3J_{C,F}$=6.4 Hz), 51.69, 39.70, 34.39. $^{19}$F NMR (470 MHz, CD$_3$OD): −234.45 (dt, $^2J_{H,F}$=47.7, $^3J_{H,F}$=23.4 Hz). MS (ESI): [M+Na$^+$] calcd for C$_{36}$H$_{50}$FNNaO$_{16}$=794.3. Found 794.5.

Procedures for the Synthesis of Compound 3a/b (FIG. 20).

Compound 28a was prepared from 14 according to the methods known in the art [87].

Compound 28b was prepared from 14 according to the similar procedure for the preparation of 28a. Colorless thick oil; 32% yield; $^1$H NMR (400 MHz, CDCl$_3$): δ 5.3-5.2 (m, 3H), 4.78 (d, J=1.4 Hz, 1H), 4.25 (dd, J=5.0, 12.4 Hz, 1H), 4.06 (dd, J=2.3, 12.4 Hz, 1H), 3.98 (m, 1H), 3.81 (m, 1H), 3.51 (m, 1H), 2.29 (m, 2H), 2.12 (s, 3H), 2.07 (s, 3H), 2.01 (s, 3H), 1.95-1.94 (m, 4H), 1.79 (m, 2H). $^{13}$C NMR (100 MHz, CDCl$_3$): δ 170.77, 170.18, 170.00, 169.84, 97.66, 83.27, 69.62, 69.22, 69.16, 68.49, 66.50, 66.12, 62.46, 27.93, 21.01, 20.86, 20.81, 15.27. MS (ESI): [M+Na$^+$] calcd for C$_{19}$H$_{26}$NaO$_{10}$=437.1. Found 437.5.

Synthesis of Compound 29a and 29b:

To a solution of alkyne 28a (206 mg, 0.533 mmol) and azide 8 (279 mg, 1.2 equiv) in THF/H$_2$O (1:1, 3 mL) was added CuSO$_4$ (8.5 mg, 0.1 equiv) and sodium ascorbate (23 mg, 0.2 equiv). The mixture was stirred at room temperature for 20 h. Then, water (5 mL) and dichloromethane (5 mL) was added, transferred to a separatory funnel. The organic layer was separated and the aqueous layer was extracted with dichloromethane (5 mL×3). The organic layers were combined, washed by brine (5 mL), dried over MgSO$_4$, filtered, and concentrated. The residue was purified by silica gel column chromatography (5% methanol in ethyl acetate) to give the desired product 29a as colorless viscous oil (450 mg, 99% yield). $^1$H NMR (400 MHz, CDCl$_3$): δ 7.78 (s, 1H), 5.29-5.27 (m, 2H), 5.21 (m, 1H), 4.95 (d, J=1.4 Hz, 1H), 4.82 (d, J=12.4 Hz, 1H), 4.66 (d, J=12.4 Hz, 1H), 4.54 (t, J=5.0 Hz, 2H), 4.28 (dd, J=5.0, 12.4 Hz, 1H), 4.08 (m, 2H), 3.87 (t, J=5.5 Hz, 2H), 3.68 (t, J=6.4 Hz, 2H), 3.62-3.55 (m, 20H), 2.47 (t, J=6.4 Hz, 2H), 2.13 (s, 3H), 2.10 (s, 3H), 2.01 (s, 3H), 1.95 (s, 3H), 1.42 (s, 9H). $^{13}$C NMR (100 MHz, CDCl$_3$): δ 170.87, 170.67, 169.96, 169.81, 169.70, 143.15, 124.43, 96.74, 80.44, 70.52, 70.44, 70.32, 69.37, 69.03, 68.60, 66.84, 65.98, 62.32, 60.84, 50.29, 36.21, 28.07, 20.89, 20.79, 20.71, 20.68. MS (ESI): [M+Na$^+$] calcd for C$_{36}$H$_{59}$N$_3$NaO$_{18}$=844.4. Found 844.3.

Compound 29b was prepared from 28b following the similar procedure for the preparation of 29a; colorless viscous oil; 71% yield. $^1$H NMR (500 MHz, CDCl$_3$): δ 7.46 (s, 1H), 5.28-5.19 (m, 2H), 5.17 (m, 1H), 4.75 (d, J=1.8 Hz, 1H), 4.46 (t, J=5.2 Hz, 2H), 4.23 (dd, J=5.7, 12.6 Hz, 1H), 4.03 (dd, J=2.3, 12.1 Hz, 1H), 3.94 (m, 1H), 3.80 (t, J=5.2 Hz, 2H), 3.72 (m, 1H), 3.64 (t, J=6.3 Hz, 2H), 3.6-3.5 (m, 22H), 3.46 (m, 1H), 2.75 (t, J=7.5 Hz, 2H), 2.43 (t, J=6.9 Hz, 2H), 2.10 (s, 3H), 2.03 (s, 3H), 1.99 (s, 3H), 1.94 (s, 3H), 1.38 (s, 9H). $^{13}$C NMR (125 MHz, CDCl$_3$): δ 170.95, 170.73, 170.16, 169.97, 169.82, 146.96, 122.11, 97.62, 80.55, 70.60, 70.52, 70.39, 69.64, 69.19, 68.47, 67.59, 66.92, 66.15, 62.48, 50.15, 36.27, 29.00, 28.14, 22.37, 21.00, 20.83, 20.81. MS (ESI): [M+Na$^+$] calcd for C38H63N3NaO18=872.4. Found 872.4.

Synthesis of Compound 30a and 30b:

To a solution of compound 29a (450 mg, 0.548 mmol) in dichloromethane (2 mL) was added trifluoroacetic acid (2 mL). The mixture was stirred for 15 h. After removing the volatile components under reduced pressure, the residue was purified by silica gel column chromatography (eluent: 3% to 5% methanol in dichloromethane), giving the product 30a as colorless viscous oil (326 mg, 79% yield). $^1$H NMR (400 MHz, CDCl$_3$): δ 8.46 (br s, 1H), 7.76 (s, 1H), 5.23-5.20 (m, 2H), 5.14 (m, 1H), 4.88 (s, 1H), 4.76 (d, J=12.4 Hz, 1H), 4.59 (d, J=12.4 Hz, 1H), 4.49 (t, J=5.0 Hz, 2H), 4.22 (dd, J=5.0, 12.4 Hz, 1H), 4.03-3.98 (m, 2H), 3.81 (t, J=5.0 Hz, 2H), 3.66 (t, J=6.0 Hz, 2H), 3.60-3.50 (m, 20H), 2.52 (t, J=6.4 Hz, 2H), 2.06 (s, 3H), 2.03 (s, 3H), 1.95 (s, 3H), 1.88 (s, 3H). $^{13}$C NMR (100 MHz, CDCl$_3$): δ 174.71, 170.85, 170.12, 169.96, 169.82, 143.13, 124.61, 96.83, 70.53, 70.45, 70.39, 70.31, 69.41, 69.35, 69.08, 68.62, 66.54, 65.99, 62.35, 60.77, 50.42, 34.90, 20.95, 20.84, 20.76, 20.73. MS (ESI): [M+Na$^+$] calcd for C$_{32}$H$_{51}$N$_3$NaO$_{18}$=788.3. Found 788.4.

Compound 30b was prepared from 29b following the similar procedure for the preparation of 30a; colorless viscous oil; 91% yield; $^1$H NMR (500 MHz, CDCl$_3$): δ 8.85 (br s, 1H), 7.50 (s, 1H), 5.28-5.12 (m, 3H), 4.74 (s, 1H), 4.47 (t, J=5.2 Hz, 2H), 4.22 (dd, J=5.2, 12.6 Hz, 1H), 4.03 (dd, J=1.8, 12.6 Hz, 1H), 3.93 (m, 1H), 3.81 (t, J=5.2 Hz, 2H), 3.71 (m, 3H), 3.60-3.50 (m, 20H), 3.44 (m, 1H), 2.76 (t, J=7.5 Hz, 2H), 2.55 (t, J=6.3 Hz, 2H), 2.09 (s, 3H), 2.03 (s, 3H), 1.98 (s, 3H), 1.93 (s, 3H). $^{13}$C NMR (125 MHz, CDCl$_3$): δ 174.58, 170.79, 170.20, 170.02, 169.85, 146.79, 122.44, 97.60, 70.57, 70.55, 70.51, 70.47, 70.43, 70.33, 69.61, 69.51, 69.20, 68.48, 67.56, 66.61, 66.15, 62.50, 50.33, 34.97, 28.93, 22.17, 20.97, 20.80, 20.77. MS (ESI): [M+H$^+$] calcd for C$_{34}$H$_{56}$N$_3$O$_{18}$=794.4. Found 794.5.

Synthesis of Compound 3a and 3b:

To a solution of compound 30a (229 mg, 0.3 mmol) in anhydrous methanol (2 mL) was added sodium methoxide (25-30% w/w soln. in MeOH, 200 uL, 3.3 equiv). After the resulting solution was allowed to stir at room temperature for 5 hours, conc. HCl (83 uL, 3.3 equiv) dissolved in methanol (2 mL) was added while vigorously stirring. The solution was passed through a thin pad of silica gel, and washed thoroughly with methanol. After concentration, the product was obtained as colorless viscous oil (179 mg, 99% yield). $^1$H NMR (400 MHz, CD$_3$OD): δ 8.13 (s, 1H), 4.99 (br s, 5H), 4.88 (d, J=1.8 Hz, 1H), 4.78 (d, J=12.4 Hz, 1H), 4.62 (m, 3H), 3.91 (t, J=5.0 Hz, 2H), 3.85-3.80 (m, 2H), 3.75-3.54 (m, 26H), 2.57 (t, J=6.0 Hz, 2H). $^{13}$C NMR (100 MHz, CD$_3$OD): δ 174.51, 143.73, 125.05, 99.49, 73.56, 71.11, 70.62, 69.85, 69.75, 69.71, 69.66, 69.62, 69.52, 69.02, 67.17, 66.25, 61.40, 59.42, 50.10, 34.10. MS (ESI): [M+Na$^+$] calcd for C$_{24}$H$_{43}$N$_3$NaO$_{14}$=620.3. Found 620.5.

Compound 3b was prepared from 30b following the similar procedure for the preparation of 3a; colorless viscous oil; 95% yield; $^1$H NMR (500 MHz, CD$_3$OD): δ 7.85 (s, 1H), 4.91 (br s, 5H), 4.75 (s, 1H), 4.56 (t, J=5.2 Hz, 2H), 3.89 (t, J=5.2 Hz, 2H), 3.80-3.74 (m, 3H), 3.73-3.67 (m, 4H), 3.63-3.61 (m, 21H), 3.51-3.43 (m, 2H), 2.78 (t, J=7.5 Hz, 2H), 2.57 (t, J=5.8 Hz, 2H), 1.95 (m, 2H). $^{13}$C NMR (125 MHz, CD$_3$OD): δ 174.60, 147.13, 122.84, 100.25, 73.29, 71.30, 70.81, 69.86, 69.73, 69.67, 69.64, 69.58, 69.52, 69.12, 67.22, 66.31, 61.37, 49.84, 34.20, 29.10, 21.84. MS (ESI): [M+Na$^+$] calcd for C$_{26}$H$_{47}$N$_3$NaO$_{14}$=648.3. Found 648.4.

Procedures for the Synthesis of Compound 4 (FIG. 21)

Compound 31 was prepared according to methods known in the art [91].

Synthesis of Compound 32:

Under N$_2$, compound 31 (747 mg, 2.33 mmol) in anhydrous THF (5 mL) was slowly added to a dry round bottom flask charged with 60% NaH (131 mg, 1.4 equiv) at 0° C. When no gas (H$_2$) was released, the mixture was allowed to stir at room temperature for 30 min. After re-cooling the mixture to 0° C., tert-butyl bromoacetate (688 uL, 2 equiv) was added. The reaction mixture was stirred at 0° C. for 1 h and at 25° C. for 24 h. The mixture was poured into water (10 mL), extracted with dichloromethane (15 mL×3) and dried over MgSO$_4$. Filtration and concentration gave the crude product which was further purified by silica gel chromatography (n-hexane/ethyl acetate=1:2), giving the pure product 32 as a light yellow oil (400 mg, 40% yield). $^1$H NMR (500 MHz, CDCl$_3$): δ 4.14 (d, J=2.3 Hz, 2H), 3.97 (s, 2H), 3.70-3.60 (m, 24H), 2.41 (t, J=2.3 Hz, 1H), 1.42 (s, 9H). $^{13}$C NMR (125 MHz, CDCl$_3$): δ 169.73, 81.58, 79.70, 74.69, 70.75, 70.62, 70.45, 69.14, 69.06, 58.46, 28.17. MS (ESI): [M+Na$^+$] calcd for C$_{21}$H$_{38}$NaO$_9$=457.2. Found 457.2. Synthesis of Compound 33: To a mixture of 32 (400 mg, 0.92 mmol), 15 (550 mg, 1.1 equiv), Et$_3$N (3 mL), and THF (12 mL) was added PdCl$_2$(PPh$_3$)$_2$ (70 mg, 0.1 equiv) and CuI (38 mg, 0.2 equiv). The oxygen was excluded from the reaction system by bubbling the solution with nitrogen stream for 5 min. After stirred at room temperature for 4 h, the resulting dark red solution was concentrated, and the residue was purified by silica gel column chromatography (n-hexane/ethyl acetate: 1/2 to pure EA) to give the desired product 33 as orange thick oil (410 mg, 52% yield). $^1$H NMR (500 MHz, CDCl$_3$): δ 7.33 (d, J=8.0 Hz, 2H), 6.97 (d, J=8.6 Hz, 2H), 5.49 (m, 2H), 5.38 (d, J=1.2 Hz, 1H), 5.30 (t, J=9.8 Hz, 1H), 4.35 (s, 2H), 4.21 (m, 1H), 4.00 (m, 2H), 3.96 (s, 2H), 3.70-3.60 (m, 24H), 2.15 (s, 3H), 2.00 (s, 3H), 1.98 (s, 3H), 1.97 (s, 3H), 1.42 (s, 9H). $^{13}$C NMR (125 MHz, CDCl$_3$): δ 170.56, 169.99, 169.78, 169.73, 155.53, 133.34, 117.35, 116.43, 95.65, 85.67, 84.58, 81.57, 70.75, 70.68, 70.62, 70.52, 69.33, 69.27, 69.20, 69.06, 68.81, 65.86, 62.08, 59.24, 28.17, 20.94, 20.76. MS (ESI): [M+Na$^+$] calcd for C$_{41}$H$_{60}$NaO$_{19}$=879.4. Found 879.2.

Synthesis of Compound 4:

To a solution of compound 33 (223 mg, 0.26 mmol) in anhydrous methanol (5 mL) was added sodium methoxide (25-30% w/w soln. in MeOH, 250 uL, 5 equiv). After the resulting solution was allowed to stir at room temperature for 5 hours, the volatile components including methanol, methyl acetate and tert-butanol was removed under reduced pressure. Then, water (50 uL) and methanol (3 mL) was added. After stirring for another 5 hours, conc. HCl (100 uL) dissolved in methanol (5 mL) was added while vigorously stirring. The residue obtained after evaporation of the solvent under reduced pressure was purified by silica gel column chromatography (ethyl acetate/methanol: 1:1 to 1:2) to give the pure product 4 as colorless thick oil (145 mg, 88% yield). $^1$H NMR (500 MHz, CD$_3$OD): δ 7.35 (d, J=8.6 Hz, 2H), 7.08 (d, J=8.6 Hz, 2H), 5.49 (d, J=1.2 Hz, 1H), 4.89 (s, 5H), 4.39 (s, 2H), 3.99 (m, 1.07), 3.95 (s, 2H), 3.87 (dd, J=3.4, 9.7 Hz), 3.76-3.62 (m, 27H), 3.54 (m, 1H). $^{13}$C NMR (125 MHz, CD$_3$OD): δ 175.25, 156.76, 132.89, 116.51, 116.30, 98.68, 85.62, 83.80, 74.25, 71.00, 70.49, 69.80, 69.69, 69.55, 69.48, 69.44, 69.36, 69.30, 69.22, 69.17, 68.63, 66.91, 61.27, 58.46. MS (ESI): [M+Na$^+$] calcd for C$_{29}$H$_{44}$NaO$_{15}$=655.3. Found 655.4.

BIBLIOGRAPHY

[1] Peleg A Y, Hooper D C. Current concepts hospital-acquired infections due to gram-negative bacteria. N Engl J Med 2010; 362:1804-13.

[2] Jacobsen S M, Stickler D J, Mobley H L T, Shirtliff M E. Complicated catheter-associated urinary tract infections due to *Escherichia coli* and *Proteus mirabilis*. Clin Microbiol Rev 2008; 21:26-59.

[3] Desai D G, Liao K S, Cevallos M E, Trautner B W. Silver or nitrofurazone impregnation of urinary catheters has a minimal effect on uropathogen adherence. J Urol 2010; 184:2565-71.

[4] Ha U S, Cho Y H. Catheter-associated urinary tract infections: new aspects of novel urinary catheters. Int J Antimicrob Ag 2006; 28:485-90.

[5] Kolter R, Greenberg E P. Microbial sciences—the superficial life of microbes. Nature 2006; 441:300-2.

[6] Fey P D. Modality of bacterial growth presents unique targets: how do we treat biofilm-mediated infections? Curr Opin Microbiol 2010; 13:610-5.

[7] Cos P, Tote K, Horemans T, Maes L. Biofilms: an extra hurdle for effective antimicrobial therapy. Curr Pharm Des 2010; 16:2279-95.

[8] Ramage G, Culshaw S, Jones B, Williams C. Are we any closer to beating the biofilm: novel methods of biofilm control. Curr Opin Infect Dis 2010; 23:560-6.

[9] McBride M C, Malcolm R K, Woolfson A D, Gorman S P. Persistence of antimicrobial activity through sustained release of triclosan from pegylated silicone elastomers. Biomaterials. 2009; 30:6739-47.

[10] Fernandez I C S, van der Mei H C, Metzger S, Grainger D W, Engelsman A F, Nejadnik M R, et al. In vitro and in vivo comparisons of staphylococcal biofilm formation on a cross-linked poly(ethylene glycol)-based polymer coating. Acta Biomater 2010; 6:1119-24.

[11] Price C L, Williams D W, Waters M G J, Coulthwaite L, Verran J, Taylor R L, et al. Reduced adherence of *Candida* to silane-treated silicone rubber. J Biomed Mater Res Part B 2005; 74B:481-7.

[12] Darouiche R O, Berger D H, Khardori N, Robertson C S, Wall M J, Metzler M H, et al. Comparison of antimicrobial impregnation with tunneling of long-term central venous catheters—a randomized controlled trial. Ann Surg 2005; 242:193-200.

[13] Trautner B W, Darouiche R O. Catheter-associated infections—pathogenesis affects prevention. Arch Intern Med 2004; 164:842-50.

[14] Noimark S, Dunnill C W, Wilson M, Parkin I P. The role of surfaces in catheter-associated infections. Chem Soc Rev 2009; 38:3435-48.

[15] Rojas I A, Slunt J B, Grainger D W. Polyurethane coatings release bioactive antibodies to reduce bacterial adhesion. J Control Release. 2000; 63:175-89.

[16] Burton E A, Simon K A, Hou S Y, Ren D C, Luk Y Y. Molecular gradients of bioinertness reveal a mechanistic difference between mammalian cell adhesion and bacterial biofilm formation. Langmuir 2009; 25:1547-53.

[17] Cheng G, Xue H, Li G Z, Jiang S Y. Integrated antimicrobial and nonfouling hydrogels to inhibit the growth of planktonic bacterial cells and keep the surface clean. Langmuir 2010; 26:10425-8.

[18] Saint S, Meddings J A, Calfee D, Kowalski C P, Krein S L. Catheter-associated urinary tract infection and the medicare rule changes. Ann Intern Med 2009; 150:877-84.

[19] Andersson P, Engberg I, Lidin-Janson G, Lincoln K, Hull R, Hull S, et al. Persistence of *Escherichia coli* bacteriuria is not determined by bacterial adherence. Infect Immun 1991; 59:2915-21.

[20] Darouiche R O, Donovan W H, Del Terzo M, Thornby J I, Rudy D C, Hull R A. Pilot trial of bacterial interference for preventing urinary tract infection. Urology 2001; 58:339-44.

[21] Reid G, Howard J, Gan B S. Can bacterial interference prevent infection? Trends Microbiol 2001; 9:424-8.

[22] Sunden F, Hakansson L, Ljunggren E, Wullt B. Bacterial interference—is deliberate colonization with *Escherichia coli* 83972 an alternative treatment for patients with recurrent urinary tract infection? Int J Antimicrob Agents 2006; 28:S26-S9.

[23] Trautner B W, Hull R A, Thornby J I, Darouiche R O. Coating urinary catheters with an avirulent strain of *Escherichia coli* as a means to establish asymptomatic colonization. Infect Control Hosp Epidemiol 2007; 28:92-4.

[24] Prasad A, Cevallos M E, Riosa S, Darouiche R O, Trautner B W. A bacterial interference strategy for prevention of UTI in persons practicing intermittent catheterization. Spinal Cord 2009; 47:565-9.

[25] Preidis G A, Versalovic J. Targeting the human microbiome with antibiotics, probiotics, and prebiotics: gastroenterology enters the metagenomics era. Gastroenterology 2009; 136:2015-31.

[26] Senok A C, Ismaeel A Y, Botta G A. Probiotics: facts and myths. Clin Microbiol Infect 2005; 11:958-66.

[27] Ventura M, O'Flaherty S, Claesson M J, Turroni F, Klaenhammer T R, van Sinderen D, et al. Genome-scale analyses of health-promoting bacteria: probiogenomics. Nat Rev Microbiol 2009; 7:61-U77.

[28] Ferrieres L, Hancock V, Klemm P. Biofilm exclusion of uropathogenic bacteria by selected asymptomatic bacteriuria *Escherichia coli* strains. Microbiology 2007; 153:1711-9.

[29] Roos V, Ulett G C, Schembri M A, Klemm P. The asymptomatic bacteriuria *Escherichia coli* strain 83972 outcompetes uropathogenic *E. coli* strains in human urine. Infect Immun 2006; 74:615-24.

[30] Klemm P, Hancock V, Schembri M A. Mellowing out: Adaptation to commensalism by *Escherichia coli* asymptomatic bacteriuria strain 83972. Infect Immun 2007; 75:3688-95.

[31] Marcone V, Rocca G, Lichtner M, Calzolari E. Long-term vaginal administration of *Lactobacillus rhamnosus* as a complementary approach to management of bacterial vaginosis. Int J Gynecol Obstet 2010; 110:223-6.

[32] Saxelin M, Tynkkynen S, Mattila-Sandholm T, de Vos W M. Probiotic and other functional microbes: from markets to mechanisms. Curr Opin Biotechnol 2005; 16:204-11.

[33] Falagas M E, Makris G C. Probiotic bacteria and biosurfactants for nosocomial infection control: a hypothesis. J Hosp Infect 2009; 71:301-6.

[34] Sunden F, Hakansson L, Ljunggren E, Wullt B. *Escherichia coli* 83972 bacteriuria protects against recurrent lower urinary tract infections in patients with incomplete bladder emptying. J Urol 2010; 184:179-85.

[35] Hull R, Rudy D, Donovan W, Svanborg C, Wieser I, Stewart C, et al. Urinary tract infection prophylaxis using *Escherichia coli* 83972 in spinal cord injured patients. J Urol 2000; 163:872-7.

[36] Marco M L, Pavan S, Kleerebezem M. Towards understanding molecular modes of probiotic action. Curr Opin Biotechnol 2006; 17:204-10.

[37] Ferrieres L, Hancock V, Klemm P. Specific selection for virulent urinary tract infectious *Escherichia coli* strains during catheter-associated biofilm formation. FEMS Immunol Med Microbiol 2007; 51:212-9.

[38] Trautner B W, Darouiche R O, Hull R A, Hull S, Thornby J I. Pre-inoculation of urinary catheters with *Escherichia coli* 83972 inhibits catheter colonization by *Enterococcus faecalis*. J Urol 2002; 167:375-9.

[39] Trautner B W, Hull R A, Darouiche R O. *Escherichia coli* 83972 inhibits catheter adherence by a broad spectrum of uropathogens. Urology 2003; 61:1059-62.

[40] Darouiche R O, Riosa S, Hull R A. Comparison of *Escherichia coli* strains as agents for bacterial interference. Infect Control Hosp Epidemiol 2010; 31:659-61.

[41] Mulvey M A. Adhesion and entry of uropathogenic *Escherichia coli*. Cell Microbiol. 2002; 4:257-71.

[42] Klemm P, Roos V, Ulett G C, Svanborg C, Schembri M A. Molecular characterization of the *Escherichia coli* asymptomatic bacteriuria strain 83972: the taming of a pathogen. Infect Immun 2006; 74:781-5.

[43] Trautner B W, Cevallos M E, Li H G, Riosa S, Hull R A, Hull S I, et al. Increased expression of type-1 fimbriae by nonpathogenic *Escherichia coli* 83972 results in an increased capacity for catheter adherence and bacterial interference. J Infect Dis 2008; 198:899-906.

[44] Pratt L A, Kolter R. Genetic analysis of *Escherichia coli* biofilm formation: roles of flagella, motility, chemotaxis and type I pili. Mol Microbiol 1998; 30:285-93.

[45] Liang M N, Smith S P, Metallo S J, Choi I S, Prentiss M, Whitesides G M. Measuring the forces involved in polyvalent adhesion of uropathogenic *Escherichia coli* to mannose-presenting surfaces. Proc Natl Acad Sci USA 2000; 97:13092-6.

[46] Qian X P, Metallo S J, Choi I S, Wu H K, Liang M N, Whitesides G M. Arrays of self-assembled monolayers for studying inhibition of bacterial adhesion. Anal Chem 2002; 74:1805-10.

[47] Qin G, Santos C, Zhang W, Li Y, Kumar A, Erasquin U J, et al. Biofunctionalization on alkylated silicon substrate surfaces via "click" chemistry. J Am Chem Soc 2010; 132:16432-41.

[48] Barth K A, Coullerez G, Nilsson L M, Castelli R, Seeberger P H, Vogel V, et al. An engineered mannoside presenting platform: *Escherichia coli* adhesion under static and dynamic conditions. Adv Funct Mater 2008; 18:1459-69.

[49] Zhu X Y, Holtz B, Wang Y N, Wang L X, Orndorff P E, Guo A. Quantitative glycomics from fluidic glycan microarrays. J Am Chem Soc 2009; 131:13646-50.

[50] Williams D F. On the mechanisms of biocompatibility. Biomaterials 2008; 29:2941-53.

[51] Yoda R. Elastomers for biomedical applications. J Biomater Sci Polym Ed 1998; 9:561-626.

[52] Musolf M C. Altering the physical properties of silicone elastomers for medical device applications. Med Device Technol 1990; 1:26-9.

[53] Toth A, Bertoti I, Blazso M, Banhegyi G, Bognar A, Szaplonczay P. Oxidative damage and recovery of silicone-rubber surfaces. 1. X-ray photoelectron spectroscopic study. J Appl Polym Sci 1994; 52:1293-307.

[54] Hillborg H, Gedde U W. Hydrophobicity recovery of polydimethylsiloxane after exposure to corona discharges. Polymer 1998; 39:1991-8.

[55] Hillborg H, Gedde U W. Hydrophobicity changes in silicone rubbers. IEE Trans Dielectr Electr Insul 1999; 6:703-17.

[56] Zhu Y, Haji K, Otsubo M, Honda C. Surface degradation of silicone rubber exposed to corona discharge. IEEE Trans Plasma Sci 2006; 34:1094-8.

[57] Nieto C, Espinosa M. Construction of the mobilizable plasmid pMV158GFP, a derivative of pMV158 that carries the gene encoding the green fluorescent protein. Plasmid 2003; 49:281-5.

[58] Bodas D, Khan-Malek C. Hydrophilization and hydrophobic recovery of PDMS by oxygen plasma and chemical treatment—an SEM investigation. Sens Actuators B Chem 2007; 123:368-73.

[59] Bodas D, Rauch J Y, Khan-Malek C. Surface modification and aging studies of addition-curing silicone rubbers by oxygen plasma. Eur Polym J 2008; 44:2130-9.

[60] Haines S R, Beamson G, Williams R L, Weightman P. Changes in the electronic structure of silicone rubber surfaces induced by oxygen plasma treatment. Surf Interface Anal 2007; 39:942-7.

[61] Morra M, Occhiello E, Marola R, Garbassi F, Humphrey P, Johnson D. On the aging of oxygen plasma-treated polydimethylsiloxane polymers. J Colloid Interface Sci 1990; 137:11-24.

[62] Everaert E P, Vandermei H C, Devries J, Busscher H J. Hydrophobic recovery of repeatedly plasma-treated silicone-rubber. 1. Storage in air. J Adhes Sci Technol 1995; 9:1263-78.
[63] Everaert E P, VanderMei H C, Busscher H J. Hydrophobic recovery of repeatedly plasma-treated silicone rubber. 2. A comparison of the hydrophobic recovery in air, water, or liquid nitrogen. J Adhes Sci Technol 1996; 10:351-9.
[64] Owen M J, Smith P J. Plasma treatment of polydimethylsiloxane. J Adhes Sci Technol 1994; 8:1063-75.
[65] Delorme N, Bardeau J, Bulou A, Poncin-Epaillard F. Controlled modification of octadecyltrichlorosilane self-assembled monolayer by $CO_2$ plasma. Thin Solid Films 2006:612-8.
[66] Luo H L, Sheng J, Wan Y Z. Plasma polymerization of styrene with carbon dioxide under glow discharge conditions. Appl Surf Sci 2007; 253:5203-7.
[67] Wang M J, Chang Y I, Epaillard F P. Illustration of the interface between $N_2/CO_2$ plasmas and polystyrene surface. Surf Interface Anal 2005; 37:325-31.
[68] Medard N, Soutif J C, Poncin-Epaillard F. Characterization of $CO_2$ plasma-treated polyethylene surface bearing carboxylic groups. Surf Coat Technol 2002; 160:197-205.
[69] Medard N, Soutif J C, Poncin-Epaillard F. $CO_2$, $H_2O$ and $CO_2/H_2O$ plasma chemistry for polyethylene surface modification. Langmuir 2002; 18:2246-53.
[70] Hettlich H J, Otterbach F, Mittermayer C, Kaufmann R, Klee D. Plasma-induced surface modifications on silicone intraocular lenses—chemical analysis and in vitro characterization. Biomaterials 1991; 12:521-4.
[71] Svenson S, Tomalia D A. Dendrimers in biomedical applications—reflections on the field. Adv Drug Deliv Rev 2005; 57:2106-29.
[72] Stiriba S E, Frey H, Haag R. Dendritic polymers in biomedical applications: from potential to clinical use in diagnostics and therapy. Angew Chem Int Ed 2002; 41:1329-34.
[73] Lee C C, MacKay J A, Frechet J M J, Szoka F C. Designing dendrimers for biological applications. Nat Biotechnol 2005; 23:1517-26.
[74] Bliznyuk V N, Rinderspacher F, Tsukruk V V. On the structure of polyamidoamine dendrimer monolayers. Polymer 1998; 39:5249-52.
[75] Yam C M, Deluge M, Tang D, Kumar A, Cai C Z. Preparation, characterization, resistance to protein adsorption, and specific avidin-biotin binding of poly(amidoamine) dendrimers functionalized with oligo(ethylene glycol) on gold. J Colloid Interface Sci 2006; 296:118-30.
[76] Cha B J, Kang Y S, Won J. Preparation and characterization of dendrimer layers on poly(dimethylsiloxane) films. Macromolecules 2001; 34:6631-6.
[77] Gibiansky M L, Conrad J C, Jin F, Gordon V D, Motto D A, Mathewson M A, et al. Bacteria Use Type IV Pili to Walk Upright and Detach from Surfaces. Science 2010; 330:197-U50.
[78] Lopez A I, Reins R Y, McDermott A M, Trautner B W, Cai C. Antibacterial activity and cytotoxicity of PEGylated poly(amidoamine) dendrimers. Mol Biosyst 2009; 5:1148-56.
[79] Calabretta M K, Kumar A, McDermott A M, Cai C. Antibacterial activities of poly(amidoamine) dendrimers terminated with amino and poly(ethylene glycol) groups. Biomacromolecules 2007; 8:1807-11.
[80] Lasaro M A, Salinger N, Zhang J, Wang Y T, Zhong Z T, Goulian M, et al. F1C Fimbriae Play an Important Role in Biofilm Formation and Intestinal Colonization by the *Escherichia coli* Commensal Strain Nissle 1917. Appl Environ Microbiol 2009; 75:246-51.
[81] Han Z F, Pinkner J S, Ford B, Obermann R, Nolan W, Wildman S A, et al. Structure-Based Drug Design and Optimization of Mannoside Bacterial FimH Antagonists. J Med Chem 2010; 53:4779-92.
[82] Klein T, Abgottspon D, Wittwer M, Rabbani S, Herold J, Jiang X H, et al. FimH Antagonists for the Oral Treatment of Urinary Tract Infections: From Design and Synthesis to in Vitro and in Vivo Evaluation. J Med Chem 2010; 53:8627-41.
[83] Bouckaert J, Mackenzie J, de Paz J L, Chipwaza B, Choudhury D, Zavialov A, et al. The affinity of the FimH fimbrial adhesin is receptor-driven and quasi-independent of *Escherichia coli* pathotypes. Mol Microbiol 2006; 61:1556-68.
[84] Touaibia M, Wellens A, Shiao T C, Wang Q, Sirois S, Bouckaert J, et al. Mannosylated G(0) dendrimers with nanomolar affinities to *Escherichia coli* FimH. Chem Med Chem. 2007; 2:1190-201.
[85] Stentebjerg-Olesen B, Chakraborty T, Klemm P. Type 1 fimbriation and phase switching in a natural *Escherichia coli* fimB null strain, Nissle 1917. J Bacteriol 1999; 181: 7470-8.
[86] Chokhawala, H. A.; Huang, S.; Lau, K.; Yu, H.; Cheng, J.; Thon, V.; Hurtado-Ziola, N.; Guerrero, J. A.; Varki, A.; Chen, X. ACS Chem. Biol. 2008, 3, 567.
[87] Boomgaarden, W.; Vogtle, F.; Nieger, M.; Hupfer, H. Chem. Eur. J. 1999, 5, 345.
[88] Touaibia, M.; Wellens, A.; Shiao, T. C.; Wang, Q.; Sirois, S.; Bouckaert, J.; Roy, R. Chem Med Chem 2007, 2, 1190.
[89] (a) Reynolds, D. D.; Evans, W. L. J. Am. Chem. Soc. 1940, 62, 66. (b) Yu, H.; Chen, X. Org. Lett. 2006, 8, 2393.
[90] Trayner, B. J.; Grant, T. N.; West, F. G.; Cheeseman, C. I. Bioorg. Med. Chem. 2009, 17, 5488.
[91] Gill, H. S.; Tinianow, J. N.; Ogasawara, A.; Flores, J. E.; Vanderbilt, A. N.; Raab, H.; Scheer, J. M.; Vandlen, R.; Williains, S. P.; Marik, J. J. Med. Chem. 2009, 52, 5816.

The present invention is well adapted to attain the ends and advantages mentioned as well as those that are inherent therein. The particular embodiments disclosed above are illustrative only, as the present invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered or modified and all such variations are considered within the scope and spirit of the present invention. Also, the terms in the claims have their plain, ordinary meaning unless otherwise explicitly and clearly defined by the patentee.

It is therefore, contemplated that the claims will cover any such modifications or embodiments that fall within the true scope of the invention.

What is claimed is:
1. A modified silicone surface for interference to pathogen colonization, comprising:
an activated silicone layer;
a plurality of cross-linking dendrimers adsorbed onto to the activated silicone layer;
a plurality of ligand derivatives, each bound to at least one of the plurality of cross-linking dendrimers; and
a benign biofilm adhered to the plurality of ligand derivatives.

2. The modified silicone surface according to claim 1, wherein the activated silicone layer comprises an oxidized silicone layer.

3. The modified silicone surface according to claim 2, wherein the oxidized silicone layer comprises oxidized carbon species.

4. The modified silicone surface according to claim 1, wherein the activated silicone layer comprises poly(dimethylsiloxane).

5. The modified silicone surface according to claim 1, wherein the cross-linking dendrimers each comprise an amidation product of the amino-terminus of an amino-terminated crosslinking dendrimer.

6. The modified silicone surface according to claim 5, wherein the cross-linking dendrimers each comprise a dendrimeric moiety selected from the group consisting of poly(amido amine) polylysine, poly(amino acid), polyallylamine, polyamines, poly(propylene imine), and combinations thereof.

7. The modified silicone surface according to claim 6, wherein the cross-linking dendrimers each comprise a generation 5 poly(amido amine) dendrimer.

8. The modified silicone surface according to claim 1, wherein the ligand derivatives each comprise an amidation product of a carboxylic acid terminal group.

9. The modified silicone surface according to claim 1, wherein the ligand derivatives each comprise a linker.

10. The modified silicone surface according to claim 1, wherein the ligand comprises mannose.

11. The modified silicone surface according to claim 10, wherein the ligand derivatives each comprise an oligo(ethylene) glycol linker and a glycosidic linkage to one of the oligo(ethylene) glycol linker and a moiety bonded to the oligo(ethylene) glycol linker, wherein the moiety is selected from the group consisting of phenyl, alkylphenyl, biphenyl, fluorinated biphenyl, hydroxylated biphenyl, and triazolylalkyl.

12. The modified silicone surface according to claim 1, wherein the benign biofilm is stable.

13. The modified silicone surface according to claim 1, wherein the benign biofilm comprises a plurality of bacteria.

14. The modified silicone surface according to claim 13, wherein the bacteria comprise bacteria oriented vertically.

15. The modified silicone surface according to claim 13, wherein the benign biofilm is dense.

16. The modified silicone surface according to claim 13, wherein the bacteria comprise E. coli 83972.

17. The modified silicone surface according to claim 13, wherein the bacteria comprise E. coli Nissle 1917.

18. The modified silicone surface according to claim 1;
wherein the activated silicone layer comprises poly(dimethyl siloxane) and oxidized carbon species;
wherein the cross-linking dendrimers each comprise an amidation product of generation 5 amino-terminated poly(amido amine) dendrimer;
wherein the mannose derivatives each comprise the amidation product of a carboxy terminus, an oligo(ethylene) glycol linker, and a glycosidic linkage to one of the oligo(ethylene) glycol linker and a moiety bonded to the oligo(ethylene) glycol linker,
wherein the moiety is selected from the group consisting of phenyl, alkylphenyl, biphenyl, fluorinated biphenyl, hydroxylated biphenyl, and triazolylalkyl; and
wherein the benign biofilm comprises a plurality of vertically oriented bacteria selected from the group consisting of E. coli 83972 and E. coli Nissle 1917.

19. A method for making a modified silicone surface for interference to pathogen colonization comprising:
activating a silicone surface;
adsorbing a plurality of cross-linking dendrimers to the silicone surface; binding a plurality of ligand derivatives to the plurality of cross-linking dendrimers; and
adhering a benign biofilm to the plurality of ligand derivatives.

20. The method for making a modified silicone surface according to claim 19, wherein the activating comprises oxidizing.

21. The method according to claim 20, wherein the oxidizing comprises treating with a plasma.

22. The method according to claim 21, wherein the treating occurs under optimized conditions.

23. The method according to claim 22, wherein the optimized conditions comprise low power.

24. The method according to claim 23, wherein the power is between about 1 W and about 10 W.

25. The method according to claim 22, wherein the benign biofilm comprises a plurality of bacteria and the optimized conditions further comprise a plasma exposure time large enough to generate dense coverage of the bacteria and small enough to minimize degradation of the oxidized silicone layer.

26. The method according to claim 21, wherein the optimized conditions comprise a plasma exposure time between about 30 seconds and about 60 seconds.

27. The method according to claim 19, wherein the adsorbing comprises immersing the activated silicone surface in a solution of the plurality of cross-linking dendrimers.

28. The method according to claim 19, wherein the cross-linking dendrimers are aminoterminated, the ligand derivatives are carboxy-terminated, and the binding comprises amidation.

29. The method according to claim 27, wherein the binding comprises providing the ligand derivatives.

30. The method according to claim 29, wherein the ligand comprises mannose derivative.

31. The method according to claim 29, wherein the ligand derivatives each comprise an oligo(ethylene) glycol linker.

32. The method according to claim 29, wherein the providing comprises forming a glycosidic linkage to one of the oligo(ethylene) glycol linker and a moiety bonded to the oligo(ethylene) glycol linker, wherein the moiety is selected from the group consisting of phenyl, alkylphenyl, biphenyl, fluorinated biphenyl, hydroxylated biphenyl, and triazolylalkyl.

33. The method according to claim 19, wherein the adsorbing precedes the binding.

34. The method according to claim 19, wherein the binding precedes the adsorbing.

35. The method according to claim 19, wherein the adhering comprises incubation in a bacterial culture.

36. The method according to claim 22, wherein the bacteria comprise bacteria selected from the group consisting of E. coli 83972 and E. coli Nissle 1917.

37. The method according to claim 35, wherein the bacterial culture comprises bacteria selected from the group consisting of E. coli 83972 and E. coli Nissle 1917.

* * * * *